US011965881B2

(12) United States Patent
Motamedi et al.

(10) Patent No.: US 11,965,881 B2
(45) Date of Patent: Apr. 23, 2024

(54) NANOSENSORS AND METHODS FOR DETECTION OF BIOLOGICAL MARKERS

(71) Applicants: The Board of Regents of The University of Texas System, Austin, TX (US); Kansas State University Research Foundation, Manhattan, KS (US)

(72) Inventors: Massoud Motamedi, Houston, TX (US); Allan R. Brasier, Galveston, TX (US); Stefan H. Bossmann, Manhattan, KS (US); Christopher T. Culbertson, Manhattan, KS (US); Deryl Troyer, Manhattan, KS (US)

(73) Assignees: Kansas State University Research Foundation, Manhattan, KS (US); Board of Regents of The University of Texas System, Austin, TX (US)

( * ) Notice: Subject to any disclaimer, the term of this patent is extended or adjusted under 35 U.S.C. 154(b) by 1555 days.

(21) Appl. No.: 16/088,407

(22) PCT Filed: Mar. 24, 2017

(86) PCT No.: PCT/US2017/024070
§ 371 (c)(1),
(2) Date: Sep. 25, 2018

(87) PCT Pub. No.: WO2017/165800
PCT Pub. Date: Sep. 28, 2017

(65) Prior Publication Data
US 2020/0300849 A1  Sep. 24, 2020

Related U.S. Application Data

(60) Provisional application No. 62/313,511, filed on Mar. 25, 2016.

(51) Int. Cl.
*G01N 33/543* (2006.01)
*B01L 3/00* (2006.01)
*G01N 33/574* (2006.01)

(52) U.S. Cl.
CPC .. *G01N 33/54346* (2013.01); *B01L 3/502715* (2013.01); *G01N 33/574* (2013.01); *B01L 2300/0636* (2013.01); *B01L 2300/0816* (2013.01); *G01N 2333/70596* (2013.01)

(58) Field of Classification Search
None
See application file for complete search history.

(56) References Cited

U.S. PATENT DOCUMENTS

| 8,053,199 | B2 | 11/2011 | Brasier et al. | |
|---|---|---|---|---|
| 8,877,951 | B2 | 11/2014 | Wang et al. | |
| 8,947,656 | B2 | 2/2015 | Cunningham | |
| 8,969,027 | B2 * | 3/2015 | Bossmann | B82Y 15/00 977/773 |
| 2007/0116600 | A1 * | 5/2007 | Kochar | B01L 3/5082 422/65 |
| 2009/0098540 | A1 * | 4/2009 | Baeumner | G01N 27/3277 435/6.12 |
| 2012/0263651 | A1 | 10/2012 | Widen et al. | |
| 2013/0183702 | A1 | 7/2013 | Bossmann et al. | |
| 2015/0119278 | A1 * | 4/2015 | Goetzl | G01N 33/6896 435/7.1 |

FOREIGN PATENT DOCUMENTS

| WO | WO 2008074023 | * | 6/2008 | ............ C12Q 1/68 |
|---|---|---|---|---|
| WO | 2015084800 | | 6/2015 | |
| WO | 2016149637 | | 9/2016 | |

OTHER PUBLICATIONS

Tamamura, Tsukasa "Magnetic-Particle-Sensing Based Diagnostic Protocols and Applications," Sensors, 2015, vol. 15, pp. 12983-12998.
Yang, Fang "Exosome separation using microfluidic systems: size-based, immunoaffinity-based and dynamic methodologies," Biotechnology Journal, 2017, vol. 12.
Yang, Yuanyuan, "Paper-Based Microfluidic Devices: Emerging Themes and Applications," Analytical Chemistry, Dec. 7, 2016, vol. 89, pp. 71-91.
Zhang, Diming "Biosensors and bioelectronics on smart phone for portable biochemical detection," Biosensors and Bioelectronics, Aug. 20, 2015, vol. 75, pp. 273-284.
Worner, Michael "Nanoarray-Surfaces by Reconstitution of the Porin MspA into Stabilized Long-Chain-Lipid-Monolayers at a Gold-Surface," Jun. 23, 2016, Electroanalysis, vol. 18 No. 19-20, pp. 1859-1870.
International Search Report and Written Opinion dated Dec. 15, 2017, in the PCT/US2017/024070 filed Mar. 24, 2017.
Rho, Junsung et al. "Magnetic Nanosensor for Detection and Profiling of Erythrocyte-Derived Microvesicles," ACS Nano. Dec. 23, 2013, pp. 11227-11233, vol. 7(12).
Udukala, Dinusha N. et al. "Early breast cancer screening using Iron/iron oxide-based nanoplatforms with sub-femtomolar limits of detection." Beilstein Journal of Nanotechnology, Mar. 7, 2016, pp. 364-373, vol. 7.
Zhao, Yingxin et al. "Systematic Analysis of Cell-Type Differences in the Epithelial Secretome Reveals Insights into the Pathogenesis of Respiratory Track Infections," J. Immunol, Mar. 3, 2017.

(Continued)

*Primary Examiner* — Ann Montgomery
(74) *Attorney, Agent, or Firm* — Hovey Williams LLP; Crissa A. Cook

(57) ABSTRACT

Methods and devices for microfluidic detection of a biological maker in a biospecimen collected from a subject are disclosed. The microfluidic devices include nanoparticle-based nanosensors comprising supramolecular recognition sequences, protease consensus sequences, post-translationally modifiable sequences, or sterically hindered benzylether bonds for specific interaction with a biological marker. Also disclosed are particular nanosensors for detecting cytokines, and other proteins based upon supramolecular recognition without chemical modification or enzymatic cleavage.

20 Claims, 13 Drawing Sheets

Specification includes a Sequence Listing.

(56) References Cited

OTHER PUBLICATIONS

Long, Kenneth D., "Smartphone instrument for portable enzyme-linked immunosorbent assays," Biomedical Optics Express, Oct. 1, 2014, vol. 5, No. 11.

Gallegos, Dustin "Label-free biodetection using a smartphone" Lab Chip, Apr. 3, 2013, vol. 13, pp. 2124-2132.

Yang, Ke et al. "Novel developments in mobile sensing based on the integration of microfluidic devices and smartphones," Lab Chip, Feb. 8, 2016, vol. 16, pp. 943-958.

Ahrberg, Christian D. "Polymerase chain reaction in microfluidic devices," Lab Chip, Sep. 6, 2016, vol. 16, pp. 3866-3884.

Dixon, Christopher et al. "Printed Microfluidics," Adv. Funct. Mater. 2017, wileyonlinelibrary.com.

Pinto I.F. et al. "The application of microbeads to microfluidic systems for enhanced detection and purification of biomolecules," Methods, Dec. 8, 2016.

Roda, Aldo et al. "Smartphone-based biosensors: A critical review and perspectives, " Trends in Analytical Chemistry, 2016, vol. 79, pp. 317-325.

Worner, Michael, et al. "Characterization of Nanostructured Surfaces Generated by Reconstitution of the Porin MspA from Mycobacterium smegmatis," Small, 2007, pp. 1084-1097, vol. 3, No. 6.

Yu, Hojeong, et al. "Smartphone Fluorescence Spectroscopy" Analytical Chemistry, Aug. 6, 2014, pp. 8805-8813, vol. 86.

Paper for Sonarmed AirWave Health Economics in the adult ICU, Mar. 24, 2011.

Ganesana, Mallikarjunarao et al. " Analytical Techniques in Neuroscience: Recent Advances in Imaging, Separation, and Electrochemical Methods," Anal. Chem. Nov. 10, 2016, pp. 314-341, vol. 89.

Sadeghi, Jalal "Out-of-plane integration of a multimode optical fiber for single particle/cell detection at multiple points on a microfluidic device with applications to particle/cell counting, velocimetry, size discrimination and the analysis of single cell lysate injections," Lab on a Chip, Nov. 24, 2016.

Patabadige, Damith E. "Integrating Optical Fiber Bridges in Microfluidic Devices to Create Multiple Excitation/Detection Points for Single Cell Analysis," Analytical Chemistry, Sep. 14, 2016, pp. 9920-9925, vol. 88.

Soung, Young Hwa "Exosomes in Cancer Diagnostics," Cancers, Jan. 12, 2017, vol. 9 (8).

Fujita, Yu "Extracellular vesicles in lung microenvironment and pathogenesis," Trends in Molecular Medicine Sep. 2015, vol. 21, No. 9.

\* cited by examiner

SEQUENCE LISTING

<160> NUMBER OF SEQ ID NOS: 81

<210> SEQ ID NO 1
<211> LENGTH: 7
<212> TYPE: PRT
<213> ORGANISM: Artificial Sequence
<220> FEATURE:
<223> OTHER INFORMATION: Synthetic supramolecular recognition sequence

<400> SEQUENCE: 1

Cys Gln Glu Gln Phe Trp Trp
1               5

<210> SEQ ID NO 2
<211> LENGTH: 13
<212> TYPE: PRT
<213> ORGANISM: Artificial Sequence
<220> FEATURE:
<223> OTHER INFORMATION: Synthetic supramolecular recognition sequence

<400> SEQUENCE: 2

Pro Tyr Phe Pro Arg Gly Ser Ser Tyr Gln Gly Trp Asn

```
1               5                    10
```

<210> SEQ ID NO 3
<211> LENGTH: 6
<212> TYPE: PRT
<213> ORGANISM: Artificial Sequence
<220> FEATURE:
<223> OTHER INFORMATION: Synthetic supramolecular recognition sequence

<400> SEQUENCE: 3

```
Cys Cys Ile Gln Asn Gln
1               5
```

<210> SEQ ID NO 4
<211> LENGTH: 8
<212> TYPE: PRT
<213> ORGANISM: Artificial Sequence
<220> FEATURE:
<223> OTHER INFORMATION: Synthetic supramolecular recognition sequence

<400> SEQUENCE: 4

```
Ala Trp Tyr Gln Pro Gln Phe Glu
1               5
```

<210> SEQ ID NO 5
<211> LENGTH: 6
<212> TYPE: PRT
<213> ORGANISM: Artificial Sequence
<220> FEATURE:
<223> OTHER INFORMATION: Synthetic supramolecular recognition sequence

<400> SEQUENCE: 5

```
Glu Gln Gln Lys Arg Asn
1               5
```

<210> SEQ ID NO 6
<211> LENGTH: 8
<212> TYPE: PRT
<213> ORGANISM: Artificial Sequence
<220> FEATURE:
<223> OTHER INFORMATION: Synthetic supramolecular recognition sequence

<400> SEQUENCE: 6

```
Cys Asn His Gly Lys Phe Tyr Cys
1               5
```

<210> SEQ ID NO 7
<211> LENGTH: 8
<212> TYPE: PRT
<213> ORGANISM: Artificial Sequence
<220> FEATURE:
<223> OTHER INFORMATION: Synthetic supramolecular recognition sequence

<400> SEQUENCE: 7

```
Asn Ile Tyr Cys Asn Ile Ala Tyr
1               5
```

<210> SEQ ID NO 8
<211> LENGTH: 8
<212> TYPE: PRT
<213> ORGANISM: Artificial Sequence
<220> FEATURE:
<223> OTHER INFORMATION: Synthetic supramolecular recognition sequence

<400> SEQUENCE: 8

```
Lys Ala Tyr Arg Trp Glu Phe Ile
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: Synthetic supramolecular recognition sequence

<400> SEQUENCE: 9

Ile Gln Asn Ser Gly Ala Pro Cys His
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic supramolecular recognition sequence

<400> SEQUENCE: 10

Trp Gln Glu Ala Lys Asn Ala Asn Gln Met
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Synthetic supramolecular recognition sequence

<400> SEQUENCE: 11

Arg His Gln Lys Thr Tyr Ser Phe
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic supramolecular recognition sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 12

Xaa Leu Pro Pro His Trp Ala Gly Ala Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic supramolecular recognition sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 13

Xaa Leu Pro Pro His Trp Ala Phe Ala Leu
1               5                   10

<210> SEQ ID NO 14
<211> LENGTH: 28
<212> TYPE: PRT
<213> ORGANISM: Artificial Sequence
```

```
<220> FEATURE:
<223> OTHER INFORMATION: Synthetic supramolecular recognition sequence

<400> SEQUENCE: 14

Leu Thr Glu Leu Glu Lys Ala Leu Asn Ser Ile Ile Asp Val Tyr His
1               5                   10                  15

Lys Tyr Ser Leu Ile Lys Gly Asn Phe His Ala Val
            20                  25

<210> SEQ ID NO 15
<211> LENGTH: 30
<212> TYPE: PRT
<213> ORGANISM: Artificial Sequence
<220> FEATURE:
<223> OTHER INFORMATION: Synthetic supramolecular recognition sequence

<400> SEQUENCE: 15

Gly Glu Ser Met Asn Phe Ser Asp Val Phe Asp Ser Ser Glu Asp Tyr
1               5                   10                  15

Phe Val Ser Val Asn Thr Ser Tyr Tyr Ser Val Asp Ser Glu
            20                  25                  30

<210> SEQ ID NO 16
<211> LENGTH: 12
<212> TYPE: PRT
<213> ORGANISM: Artificial Sequence
<220> FEATURE:
<223> OTHER INFORMATION: Synthetic supramolecular recognition sequence

<400> SEQUENCE: 16

Gly Thr Gln Trp Trp Val Val Cys Gln Gln Phe Gly
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic supramolecular recognition sequence

<400> SEQUENCE: 17

Pro Gly His Trp Ser Asp Trp Ser Pro Ser
1               5                   10

<210> SEQ ID NO 18
<211> LENGTH: 28
<212> TYPE: PRT
<213> ORGANISM: Artificial Sequence
<220> FEATURE:
<223> OTHER INFORMATION: Synthetic supramolecular recognition sequence

<400> SEQUENCE: 18

Tyr Phe Pro Glu Pro Val Thr Val Ser Gly Ala Gly Thr Phe Pro Ala
1               5                   10                  15

Val Leu Gly Ser Gly Gln Pro Pro Gly Lys Gly Leu
            20                  25

<210> SEQ ID NO 19
<211> LENGTH: 25
<212> TYPE: PRT
<213> ORGANISM: Artificial Sequence
<220> FEATURE:
<223> OTHER INFORMATION: Synthetic supramolecular recognition sequence

<400> SEQUENCE: 19
```

Thr Ala Val Tyr Tyr Cys Ala Asn Arg Ala Gly Trp Gly Met Gly Asp
1               5                   10                  15

Tyr Trp Gly Gln Gly Thr Gln Val Thr
            20                  25

<210> SEQ ID NO 20
<211> LENGTH: 16
<212> TYPE: PRT
<213> ORGANISM: Artificial Sequence
<220> FEATURE:
<223> OTHER INFORMATION: Synthetic supramolecular recognition sequence

<400> SEQUENCE: 20

Thr Ala Ser Asn Tyr Gly Ala Gly Tyr Ser Thr Asn Asp Arg His Ser
1               5                   10                  15

<210> SEQ ID NO 21
<211> LENGTH: 10
<212> TYPE: PRT
<213> ORGANISM: Artificial Sequence
<220> FEATURE:
<223> OTHER INFORMATION: Synthetic supramolecular recognition sequence

<400> SEQUENCE: 21

Asn Arg Pro Ala Gln Ala Trp Met Leu Gly
1               5                   10

<210> SEQ ID NO 22
<211> LENGTH: 20
<212> TYPE: PRT
<213> ORGANISM: Artificial Sequence
<220> FEATURE:
<223> OTHER INFORMATION: Synthetic supramolecular recognition sequence

<400> SEQUENCE: 22

Ala Val Tyr Tyr Cys Gln Gln Asn Asn Glu Asp Pro Arg Thr Phe Gly
1               5                   10                  15

Gly Gly Thr Lys
            20

<210> SEQ ID NO 23
<211> LENGTH: 13
<212> TYPE: PRT
<213> ORGANISM: Artificial Sequence
<220> FEATURE:
<223> OTHER INFORMATION: Synthetic supramolecular recognition sequence

<400> SEQUENCE: 23

Ala Gly Asp Gly Tyr Tyr Pro Tyr Ala Met Asp Asn Trp
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic supramolecular recognition sequence

<400> SEQUENCE: 24

Gly Trp Leu Pro Phe Gly Phe Ile Leu Ile Ser Ala Gly
1               5                   10

<210> SEQ ID NO 25
<211> LENGTH: 11
<212> TYPE: PRT
<213> ORGANISM: Artificial Sequence

```
<220> FEATURE:
<223> OTHER INFORMATION: Synthetic supramolecular recognition sequence

<400> SEQUENCE: 25

Tyr Gln Gln Lys Pro Gly Gln Pro Pro Lys Leu
1               5                   10

<210> SEQ ID NO 26
<211> LENGTH: 29
<212> TYPE: PRT
<213> ORGANISM: Artificial Sequence
<220> FEATURE:
<223> OTHER INFORMATION: Synthetic supramolecular recognition sequence

<400> SEQUENCE: 26

Ser Val Asn Trp Ile Arg Gln Pro Pro Gly Lys Ala Leu Glu Trp Leu
1               5                   10                  15

Ala Met Ile Trp Gly Asp Gly Lys Ile Val Tyr Asn Ser
            20                  25

<210> SEQ ID NO 27
<211> LENGTH: 10
<212> TYPE: PRT
<213> ORGANISM: Artificial Sequence
<220> FEATURE:
<223> OTHER INFORMATION: Synthetic supramolecular recognition sequence

<400> SEQUENCE: 27

Trp Leu Pro Phe Gly Phe Ile Leu Ile Ser
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic supramolecular recognition sequence

<400> SEQUENCE: 28

Thr Tyr Tyr Cys Gln Gln Trp Ser Gly Tyr Pro Tyr Thr Phe
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic supramolecular recognition sequence

<400> SEQUENCE: 29

Ser His Phe Pro Tyr Ser Gln Tyr Gln Phe Trp Lys Asn
1               5                   10

<210> SEQ ID NO 30
<211> LENGTH: 35
<212> TYPE: PRT
<213> ORGANISM: Artificial Sequence
<220> FEATURE:
<223> OTHER INFORMATION: Synthetic supramolecular recognition sequence

<400> SEQUENCE: 30

Asp Met Ser Asp Thr Asn Trp Trp Lys Gly Thr Ser Lys Gly Arg Thr
1               5                   10                  15

Gly Leu Ile Pro Ser Asn Tyr Val Ala Glu Gln Ala Glu Ser Ile Asp
            20                  25                  30
```

```
Asn Pro Leu
        35

<210> SEQ ID NO 31
<211> LENGTH: 17
<212> TYPE: PRT
<213> ORGANISM: Artificial Sequence
<220> FEATURE:
<223> OTHER INFORMATION: Synthetic supramolecular recognition sequence

<400> SEQUENCE: 31

Ile Ala Gly Lys Leu Gln Ser Ala Gly Ser Ala Leu Trp Thr Asp Gln
1               5                   10                  15

Leu

<210> SEQ ID NO 32
<211> LENGTH: 19
<212> TYPE: PRT
<213> ORGANISM: Artificial Sequence
<220> FEATURE:
<223> OTHER INFORMATION: Synthetic supramolecular recognition sequence

<400> SEQUENCE: 32

Ser Ser Pro Lys His Val Arg Phe Ser Trp His Gln Asp Ala Val Thr
1               5                   10                  15

Val Thr Cys

<210> SEQ ID NO 33
<211> LENGTH: 10
<212> TYPE: PRT
<213> ORGANISM: Artificial Sequence
<220> FEATURE:
<223> OTHER INFORMATION: Synthetic supramolecular recognition sequence

<400> SEQUENCE: 33

Ala Lys Cys Cys Pro Cys Gln Gln Trp Trp
1               5                   10

<210> SEQ ID NO 34
<211> LENGTH: 15
<212> TYPE: PRT
<213> ORGANISM: Artificial Sequence
<220> FEATURE:
<223> OTHER INFORMATION: Synthetic supramolecular recognition sequence

<400> SEQUENCE: 34

Val Gln Glu Phe Tyr Lys Asp Thr Tyr Asn Lys Leu Lys Thr Lys
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Synthetic supramolecular recognition sequence

<400> SEQUENCE: 35

Leu Asn Asn His Thr Ala Ser Ile Leu Asn Arg Met Gln Ala Asn Phe
1               5                   10                  15

<210> SEQ ID NO 36
<211> LENGTH: 19
<212> TYPE: PRT
<213> ORGANISM: Artificial Sequence
<220> FEATURE:
<223> OTHER INFORMATION: Synthetic supramolecular recognition sequence
```

<400> SEQUENCE: 36

Val Gly Ile Tyr Ile Leu Ile Ala Val Gly Ala Val Met Met Phe Val
1               5                   10                  15

Gly Phe Lys

<210> SEQ ID NO 37
<211> LENGTH: 18
<212> TYPE: PRT
<213> ORGANISM: Artificial Sequence
<220> FEATURE:
<223> OTHER INFORMATION: Synthetic supramolecular recognition sequence

<400> SEQUENCE: 37

Asn Glu Arg Asn Ile Asn Ile Thr Lys Asp Leu Leu Asp Leu Leu Val
1               5                   10                  15

Ala His

<210> SEQ ID NO 38
<211> LENGTH: 16
<212> TYPE: PRT
<213> ORGANISM: Artificial Sequence
<220> FEATURE:
<223> OTHER INFORMATION: Synthetic supramolecular recognition sequence

<400> SEQUENCE: 38

Asp Ile Asn Trp Val Lys Gln Arg Pro Gly Gln Gly Leu Glu Trp Ile
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Synthetic supramolecular recognition sequence

<400> SEQUENCE: 39

Val Leu Leu Gln Gly Lys Asn Pro Asp Ile Thr Lys Ala Trp Lys Leu
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Synthetic supramolecular recognition sequence

<400> SEQUENCE: 40

Asn Leu Ser Arg Ser Arg Trp Phe Asp Phe Pro Phe Thr Arg Glu Glu
1               5                   10                  15

<210> SEQ ID NO 41
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 41

Leu Ala Gln Ala Val Val Ser Ser
1               5

<210> SEQ ID NO 42
<211> LENGTH: 8
<212> TYPE: PRT

```
<213> ORGANISM: Artificial Sequence
<220> FEATURE:
<223> OTHER INFORMATION: Synthetic protease consensus sequence

<400> SEQUENCE: 42

Gly Ser Gln His Ile Arg Ala Glu
1               5

<210> SEQ ID NO 43
<211> LENGTH: 12
<212> TYPE: PRT
<213> ORGANISM: Artificial Sequence
<220> FEATURE:
<223> OTHER INFORMATION: Synthetic protease consensus sequence

<400> SEQUENCE: 43

Ser Leu Leu Lys Ser Arg Met Val Pro Asn Phe Asn
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 44

Gly Asp Ser Gly Leu Gly Arg Ala
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 45

Glu Val Ala Leu Val Ala Leu Lys
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 46

Leu Gly Leu Glu Gly Ala Asn Leu
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 47

Ala Ala Leu Gly Ser Ala Pro Gly
1               5

<210> SEQ ID NO 48
<211> LENGTH: 12
<212> TYPE: PRT
<213> ORGANISM: Artificial Sequence
```

```
<220> FEATURE:
<223> OTHER INFORMATION: Synthetic protease consensus sequence

<400> SEQUENCE: 48

Ser Leu Leu Ile Phe Arg Ser Trp Ala Asn Phe Asn
1               5                   10

<210> SEQ ID NO 49
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 49

Val Glu Pro Asn Ser Leu Glu Glu
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 50

Gly Glu Pro Leu Ser Leu Leu Pro
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 51

Ile Pro Val Ser Leu Arg Ser Gly
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 52

Arg Pro Phe Ser Met Ile Met Gly
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 53

Val Pro Leu Ser Leu Thr Met Gly
1               5

<210> SEQ ID NO 54
<211> LENGTH: 8
<212> TYPE: PRT
<213> ORGANISM: Artificial Sequence
<220> FEATURE:
```

<223> OTHER INFORMATION: Synthetic protease consensus sequence

<400> SEQUENCE: 54

Gly Pro Ser Gly Leu Arg Gly Ala
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 55

Val Pro Leu Ser Leu Tyr Ser Gly
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 56

Gly Ala Ala Asn Leu Val Arg Gly
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic protease consensus sequence

<400> SEQUENCE: 57

Gly Val Pro Leu Ser Leu Thr Met Gly
1               5

<210> SEQ ID NO 58
<211> LENGTH: 11
<212> TYPE: PRT
<213> ORGANISM: Artificial Sequence
<220> FEATURE:
<223> OTHER INFORMATION: Synthetic protease consensus sequence

<400> SEQUENCE: 58

Pro Gln Gly Leu Ala Gly Gln Arg Gly Ile Val
1               5                   10

<210> SEQ ID NO 59
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 59

Gly Pro Ala Gly Leu Arg Leu Ala
1               5

<210> SEQ ID NO 60
<211> LENGTH: 11
<212> TYPE: PRT
<213> ORGANISM: Artificial Sequence
<220> FEATURE:
<223> OTHER INFORMATION: Synthetic enzyme consensus sequence

<400> SEQUENCE: 60

Arg Asp Ile Tyr Ala Ala Pro Phe Phe Arg Lys
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Synthetic enzyme consensus sequence

<400> SEQUENCE: 61

Ala Met Glu Arg Arg Arg Thr Ser Ala Ala Arg Arg Ser Tyr
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetic enzyme consensus sequence

<400> SEQUENCE: 62

Lys Ala Arg Ala Ala Val Ser Pro Gln Lys Arg Lys Ala
1               5                   10

<210> SEQ ID NO 63
<211> LENGTH: 16
<212> TYPE: PRT
<213> ORGANISM: Artificial Sequence
<220> FEATURE:
<223> OTHER INFORMATION: Synthetic enzyme consensus sequence

<400> SEQUENCE: 63

Arg Ala Arg Lys Arg Arg Leu Ser Ala Pro Pro Leu Ala Ser Gly Asp
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic enzyme consensus sequence

<400> SEQUENCE: 64

Ala Lys Ala Gly Pro Pro Leu Ser Pro Arg Pro Pro His Val His
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic enzyme consensus sequence

<400> SEQUENCE: 65

Asp Leu Phe Ile Pro Asp Asn Tyr Leu Lys Met Lys Pro Ala Pro
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic enzyme consensus sequence

```
<400> SEQUENCE: 66

Ala Glu Leu Asp Pro Glu Asp Ser Met Asp Met Asp Met Ala Pro
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic enzyme consensus sequence

<400> SEQUENCE: 67

Glu Asp Glu Ala Glu Glu Leu Ser Asp Glu Asp Glu Glu Leu Lys
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic enzyme consensus sequence

<400> SEQUENCE: 68

Ala Ala Gly Pro Ala Pro Leu Ser Pro Val Pro Pro Val Val His
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Synthetic enzyme consensus sequence

<400> SEQUENCE: 69

Asp Ala Ser Arg Pro Pro Pro Leu Ser Pro Leu Pro Ser Pro Arg Ala
1               5                   10                  15

<210> SEQ ID NO 70
<211> LENGTH: 9
<212> TYPE: PRT
<213> ORGANISM: Artificial Sequence
<220> FEATURE:
<223> OTHER INFORMATION: Synthetic arginase consensus sequence

<400> SEQUENCE: 70

Gly Arg Arg Arg Arg Arg Arg Arg Gly
1               5

<210> SEQ ID NO 71
<211> LENGTH: 17
<212> TYPE: PRT
<213> ORGANISM: Artificial Sequence
<220> FEATURE:
<223> OTHER INFORMATION: Synthetic supramolecular recognition sequence

<400> SEQUENCE: 71

Ala Ile Ser Gly Ser Gly Gly Ser Thr Tyr Tyr Ala Asn Ser Val Leu
1               5                   10                  15

Gly

<210> SEQ ID NO 72
<211> LENGTH: 20
<212> TYPE: PRT
<213> ORGANISM: Artificial Sequence
<220> FEATURE:
<223> OTHER INFORMATION: Synthetic supramolecular recognition sequence
```

<400> SEQUENCE: 72

Thr Asn Leu Gly Ile Leu His Ser Met Val Ala Arg Ala Val Gly Asn
1               5                   10                  15

Asn Thr Gln Gly
            20

<210> SEQ ID NO 73
<211> LENGTH: 17
<212> TYPE: PRT
<213> ORGANISM: Artificial Sequence
<220> FEATURE:
<223> OTHER INFORMATION: Synthetic supramolecular recognition sequence

<400> SEQUENCE: 73

Gly Ile Ile Thr Tyr Ala Leu Ser Gly Gly Glu Ile Lys Ile Leu Ala
1               5                   10                  15

Gly

<210> SEQ ID NO 74
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 74

Ser Ala Val Leu Leu Glu Ala Thr
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic protease consensus sequence

<400> SEQUENCE: 75

Ser Gln Asn Tyr Pro Ile Val Gln
1               5

<210> SEQ ID NO 76
<211> LENGTH: 12
<212> TYPE: PRT
<213> ORGANISM: Artificial Sequence
<220> FEATURE:
<223> OTHER INFORMATION: Synthetic arginase consensus sequence

<400> SEQUENCE: 76

Gly Arg Arg Arg Arg Arg Arg Arg Gly Ser Ser Ser
1               5                   10

<210> SEQ ID NO 77
<211> LENGTH: 24
<212> TYPE: PRT
<213> ORGANISM: Artificial Sequence
<220> FEATURE:
<223> OTHER INFORMATION: Synthetic supramolecular recognition sequence

<400> SEQUENCE: 77

Ala Val Tyr Tyr Cys Gln Gln Asn Asn Glu Asp Pro Arg Thr Phe Gly
1               5                   10                  15

Gly Gly Thr Lys Ser Ser Ser Gly
            20

```
<210> SEQ ID NO 78
<211> LENGTH: 21
<212> TYPE: PRT
<213> ORGANISM: Artificial Sequence
<220> FEATURE:
<223> OTHER INFORMATION: Synthetic supramolecular recognition sequence

<400> SEQUENCE: 78

Gln Phe Val Lys Asp Leu Leu Leu His Leu Lys Lys Leu Phe Arg Glu
1               5                   10                  15

Gly Arg Phe Asn Gly
            20

<210> SEQ ID NO 79
<211> LENGTH: 21
<212> TYPE: PRT
<213> ORGANISM: Artificial Sequence
<220> FEATURE:
<223> OTHER INFORMATION: Synthetic supramolecular recognition sequence

<400> SEQUENCE: 79

Gln Phe Val Lys Asp Ser Leu Leu His Leu Lys Lys Leu Phe Arg Glu
1               5                   10                  15

Gly Arg Phe Asn Gly
            20

<210> SEQ ID NO 80
<211> LENGTH: 21
<212> TYPE: PRT
<213> ORGANISM: Artificial Sequence
<220> FEATURE:
<223> OTHER INFORMATION: Synthetic supramolecular recognition sequence

<400> SEQUENCE: 80

Gln Phe Val Lys Asp Ser Leu Leu His Leu Ser Lys Leu Phe Arg Glu
1               5                   10                  15

Gly Arg Phe Asn Gly
            20

<210> SEQ ID NO 81
<211> LENGTH: 21
<212> TYPE: PRT
<213> ORGANISM: Artificial Sequence
<220> FEATURE:
<223> OTHER INFORMATION: Synthetic supramolecular recognition sequence

<400> SEQUENCE: 81

Gln Phe Val Lys Asp Ser Leu Leu His Leu Ser Lys Leu Phe Arg Glu
1               5                   10                  15

Ser Arg Phe Asn Gly
            20
```

NANOSENSORS AND METHODS FOR DETECTION OF BIOLOGICAL MARKERS

CROSS-REFERENCE TO RELATED APPLICATIONS

The present application is the U.S. National Stage of International Patent Application No. PCT/US2017/024070, filed Mar. 24, 2017, which claims the priority benefit of U.S. Provisional Patent Application Ser. No. 62/313,511, filed Mar. 25, 2016, entitled Methods and System for Collecting, Processing, Profiling, and Multi-sense Detection of Biological Markers within a Biological Sample, each of which is incorporated by reference in its entirety herein.

FEDERALLY SPONSORED RESEARCH OR DEVELOPMENT

This invention was made with government support under Contract No. UL1 TR001439 awarded by the National Institutes of Health, and Contract Nos. 1159966, 1242765, and 1411993 awarded by the National Science Foundation. The government has certain rights in the invention.

SEQUENCE LISTING

The following application contains a sequence listing in computer readable format (CRF), submitted as a text file in ASCII format entitled "SequenceListing," created on Mar. 23, 2017, as 21 KB. The content of the CRF is hereby incorporated by reference.

BACKGROUND OF THE INVENTION

Field of the Invention

The present invention relates to nanosensors and instruments (e.g., microfluidics and optical sensors) and detection techniques (e.g., multiplexing) for detecting target biological markers in a specimen collected from a subject.

Description of Related Art

Inflammation is a protective response of the body to cellular damage and tissue injury. Under normal and controlled conditions, the role of this process is to remove the injurious agents while promoting wound healing and repair. However, under uncontrolled conditions, inflammatory responses can lead to excessive cellular damage resulting in chronic inflammation and destruction of normal tissue. Inflammatory airway and lung diseases, such as asthma, chronic obstructive pulmonary disease (COPD), or lung injury are characterized by chronic inflammation, fibrosis, and airway remodeling. Asthma affects the health of 26 million people, including 7 million children in the United States. It is characterized by repeated episodes of wheezing, breathlessness, chest tightness, and nighttime or early morning coughing. In 2010, 1.8 million people visited an ED for asthma-related care, and 439,000 people were hospitalized because of asthma. The human airway is continuously exposed to microorganisms, gases and allergens. As a result, the airway lining epithelial cells form the first line of defense against these environmental insults through a barrier function and secretion of protective proteins and molecules. The barrier function is the result of an impermeable barrier of lining cells connected by tight junctions, which serves to prevent organisms from invading the airway and to prevent fluid losses. The spectrum of secreted epithelial molecules is different for various regions of the lung as a consequence of the specialized cell types. For example, upper airway ciliated epithelial cells produce protective epithelial lining fluid rich in antioxidants. Pseudostratified tracheal airway cells secrete protective mucins to facilitate mucociliary particulate clearance, while lower alveolar epithelial cells.

In both children and adults, viral infections trigger asthma exacerbations by stimulating inflammatory gene expression programs in infected epithelium. These viruses include Respiratory Syncytial Virus (RSV)/human metapneumoviruses in children and Rhinovirus in adults. RSV infections of the small airways (bronchioles) is the most common cause of lower respiratory tract infections in children, infecting virtually all children by the age of 3. A recent prospective, population-based study of 5000 children presenting for acute medical care estimated that 18% of acutely ill children have acute RSV infection. Here it was observed that the presence of RSV infection produces 3-times the risk of subsequent hospitalization over that seen in infections with other common cold viruses, and in young children, hospitalization rates are 17 per 1000 babies.

Overall, ~120,000 hospitalizations for bronchiolitis are seen in the US annually. RSV is the leading cause of infant viral death. Rhinovirus is the most common cause of viral respiratory tract infections in adults, and is responsible for exacerbations of asthma in this population.

There is a continuing need for rapid detection of clinically relevant biological markers indicative of diseased states or conditions, or for monitoring of disease progression and the response of the airway to therapeutic intervention as progress is being made toward the development of personalized medicine.

Cytokines are small proteins (~5-20 kDa) that are important in cell signaling. Cytokine release has an effect on the behavior of cells around them. Cytokines are also involved in autocrine signaling, paracrine signaling and endocrine signaling as immunomodulating agents. The term "cytokine" includes chemokines, interferons, interleukins, lymphokines, and tumor necrosis factors. They are produced by macrophages, B lymphocytes, T lymphocytes as well as endothelial cells, fibroblasts, and various stromal cells. Cytokines modulate the balance between humoral and cell-based immune responses. There are both pro-inflammatory cytokines and anti-inflammatory cytokines. Pro-inflammatory cytokines include IL-1β, Interleukin 6 (IL-6), and TNF-α, which are involved in the process of pathological pain. Anti-inflammatory cytokines include IL4, IL-10, IL-13 and IFN-alpha. Macrophage Inflammatory Protein-3 (MIP3A) is another small cytokine belonging to the CC chemokine family. It is strongly chemotactic for lymphocytes and weakly attracts neutrophils. CCL20 is implicated in the formation and function of mucosal lymphoid tissues. IL-6 acts as both a pro-inflammatory cytokine and an anti-inflammatory myokine. IL-6 is secreted by T cells and macrophages to stimulate immune response. It also plays a role in fighting infections, Atherosclerosis, Depression, Alzheimer's Disease, Systemic lupus erythematosus, Prostate cancer, and Rheumatoid arthritis. Thus, it is a strong candidate for biomarker detection for a variety of diseases and condition. Thymic stromal lymphopoietin (TSLP) plays an important role in the maturation of T cell populations through activation of antigen presenting cells. Produced mainly by non-hematopoietic cells such as fibroblasts, epithelial cells and different types of stromal or stromal-like cells. Expression is linked to many disease states including asthma, inflammatory arthritis, atopic dermatitis and other allergic states. Further, co-expression of various markers, such as cytokines and MMPs can be used to detect and monitor condition progression. There is a need for techniques and instruments capable of such co-detection, which would greatly improve specificity and the diagnostic power of collected patient specimen.

SUMMARY OF THE INVENTION

The present invention is broadly concerned with nanosensors, microfluidic devices, and detection techniques for capturing, detecting, and quantifying biological markers in biospecimens collected from a subject (typically but not necessarily a mammalian subject, and usually a human patient, although veterinary uses are contemplated, such as in dogs, cats, horses, pigs, monkeys, rodents, etc.).

In one aspect, described herein are methods of microfluidic detection of a biological marker in a biological sample collected from a subject. The methods generally comprise analyzing a biological sample with a microfluidics device. The microfluidic devices comprise a cartridge and a planar substrate retained in the cartridge. The cartridge comprises a sample inlet well formed in the cartridge above a sample application region in or on the substrate and at least one detection region in fluid communication with the sample application region via a microfluidic channel extending from the sample application region to the detection region. The microfluidic channel has a terminal end positioned distal from the inlet well, and an optional absorbent pad positioned at the terminal end (to facilitate flow of the sample completely through the channel). The detection region comprises a first nanosensor immobilized therein or thereon. The nanosensor comprises a central carrier particle, a first particle tethered to the carrier particle via an oligopeptide linkage, and a second particle directly attached to the carrier particle, wherein at least one of the first and second particles is a detectable particle and the other of the first and second particles is a quencher particle. The oligopeptide linkage comprises a supramolecular recognition sequence, a protease consensus sequence, a post-translationally modifiable sequence, or a sterically hindered benzylether bond for specific interaction with the target biological marker. The biological sample collected from the subject is introduced into the inlet well and the biological sample flows to the terminal end along the microfluidic chamber, wherein the biological sample contacts the detection region before reaching the terminal end. The detection region is exposed to an energy source to generate a detectable signal from the detectable particle in the first nanosensor, and changes (e.g., decrease or increase in signal, appearance of new signal, etc.) in the detectable signal are detected based upon interaction of the biological sample (and more specifically the target marker, if present in the sample) with the first nanosensor.

Microfluidic devices are also described herein. The microfluidic devices general comprise a cartridge and a planar substrate retained in the cartridge. The cartridge comprises a sample inlet well formed in the cartridge above a sample application region in or on the substrate and at least one detection region in fluid communication with the sample application region via a microfluidic channel extending from the sample application region to the detection region. The microfluidic channel has a terminal end positioned distal from the inlet well, and an optional absorbent pad positioned at the terminal end (to facilitate flow of the sample completely through the channel). The detection region comprises a nanosensor immobilized therein or thereon. The nanosensor comprises a central carrier particle, a first particle tethered to the carrier particle via an oligopeptide linkage, and a second particle directly attached to the carrier particle, wherein at least one of the first and second particles is a detectable particle and the other of the first and second particles is a quencher particle. The oligopeptide linkage comprises a supramolecular recognition sequence, a protease consensus sequence, a post-translationally modifiable sequence, or a sterically hindered benzylether bond for specific interaction with the target biological marker.

Also described herein are nanosensors for detecting the presence of an active protein in a sample. The nanosensors comprise a central carrier particle and a first particle connected to the central carrier particle via an oligopeptide linkage that comprises a supramolecular recognition sequence, wherein the protein has specific binding to the supramolecular recognition sequence without chemical modification or enzymatic cleavage of the linkage. A second particle is also directly attached to the central carrier particle via a non-cleavable linkage (that is generally shorter than the oligopeptide linkage of the first particle). In the sensors, at least one of the first and second particles is a detectable particle and the other of the first and second particles is a quencher particle. The nanosensor is configured such that the detectable particle and quencher particle are separated by a distance that enables Förster resonance energy transfer.

Methods for detecting the presence of an active protein in a sample from a mammal are also described herein. The methods generally comprise contacting a biological sample from the mammal with a nanosensor described herein; exposing the nanosensor to an energy source to generate a detectable signal from the detectable particle; and detecting changes in the detectable particle signal upon contact of the nanosensor with the sample (and more specifically with active proteins, if present, in the sample) wherein the changes correspond to protein activity in the sample.

DETAILED DESCRIPTION OF PREFERRED EMBODIMENTS

Nanosensors

Figure 1:
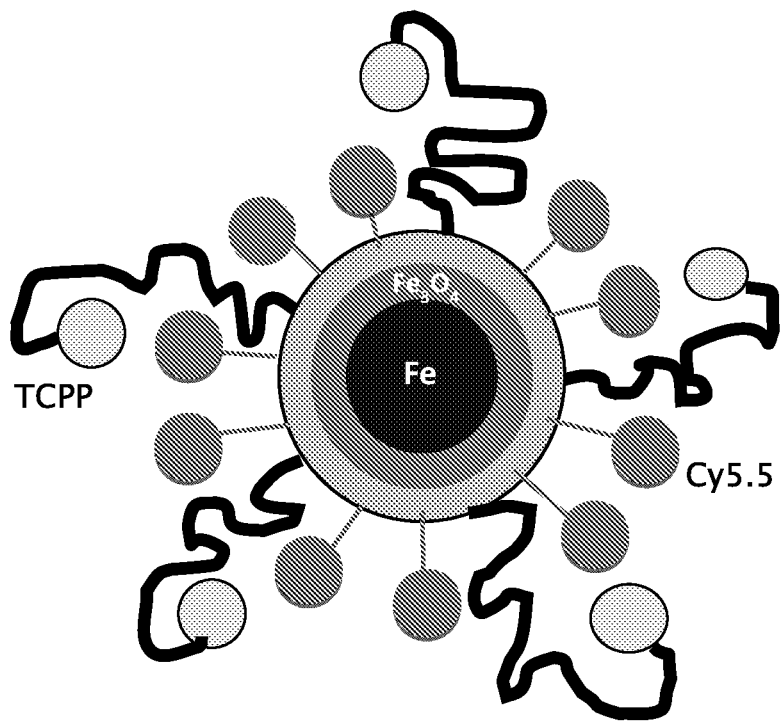
FIG. 1 is a cartoon illustration of an example of a cytokine nanosensor in accordance with an embodiment of the invention.

In one aspect, described herein are nanosensors for detecting cytokines, and other proteins based upon supramolecular recognition without chemical modification or enzymatic cleavage. In use, an oligopeptide tether between a central carrier particle and a detectable particle is recognized by the target protein, which binds thereto. Binding physically extends the recognition sequence linearly, increasing the distance between the detectable particle and the carrier particle, giving rise to a detectable change in the nanosensor, which is indicative of the presence of the target protein. An exemplary depiction of a nanosensor is shown in FIG. 1.

Figure 2:
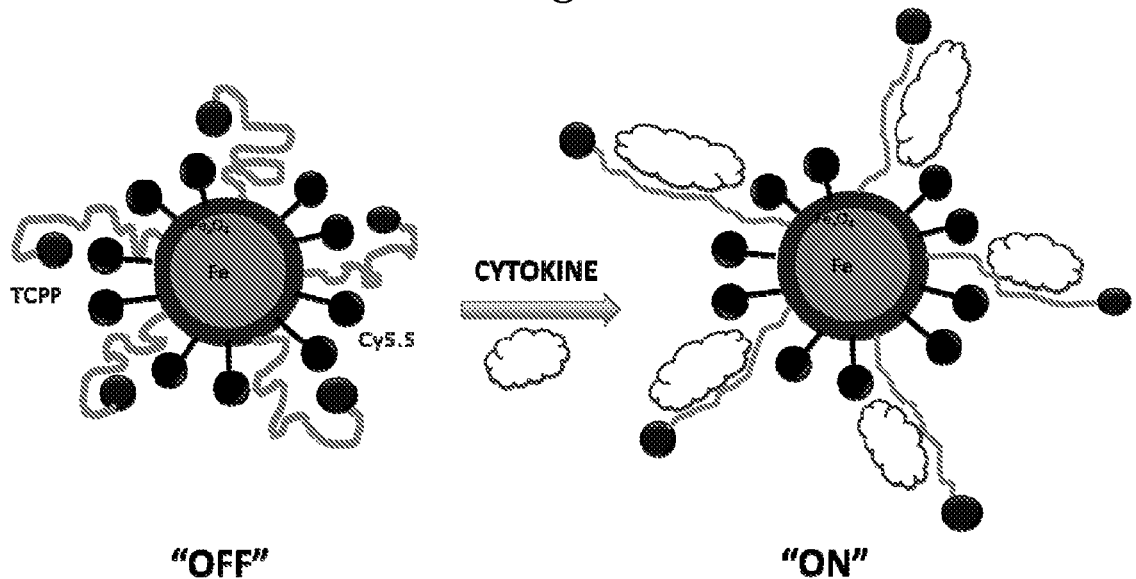
FIG. 2 is a cartoon illustration of the mechanism of action of an example of a cytokine nanosensor in accordance with an embodiment of the invention.

Whereas nanoplatforms for protease detection, such as those described in U.S. Pat. No. 8,969,027, incorporated by reference herein to the extent not inconsistent with the present disclosure, feature "protease consensus sequences" that undergo enzymatic cleavage, or nanoplatforms for detection of enzymatic posttranslational modification described in WO 2016/149637, incorporated by reference herein to the extent not inconsistent with the present disclosure, the particular nanosensors do not involve cutting or severing the oligopeptide between the nanoparticle and dye, or changing the chemical characteristics, but rather a physical binding of the target protein to the recognition sequence. Again, this binding leads to a change in the average distance between two particles, resulting in a characteristic change in a detectable signal for the particles used in the nanosensor, such as a fluorescence spectrum. The observable change in fluorescence (increase or decrease, depending on the chemical nature of the peptide sequences before and after binding) is a function of protein activity. The quenching effect can be enhanced by tethering a second dye to the surface of the carrier nanoparticle to facilitate FRET (Förster Resonance Energy Transfer). The general mechanism is depicted via a cartoon illustration in FIG. 2. It will be appreciated that unlike other sensor mechanisms, the present nanosensors are able to detect active proteins.

The nanosensors according to these embodiments comprise an oligopeptide, which is used as a peptide linkage between two particles. The linkage comprises a supramolecular recognition sequence for the target protein, which means that the linkage sequence has specificity (i.e., contains a selective binding site) for the target protein). Thus, it will be appreciated that the linkage sequences avoid non-specific binding motifs. Further, the oligopeptide linkage containing the supramolecular recognition sequence is preferably "non-cleavable" which means that it does not contain protease cleavage sites, and the like. The oligopeptide linkage attaches a detectable particle to a central carrier particle. In one or more embodiments, a quencher particle is also directly tethered or attached to the central carrier particle, such as through an amide bond. In other words, the phrase "directly attached" as used herein means that the quencher particle is connected directly to the surface of the central particle, or to a ligand layer on the surface of the central particle (and is not attached via an enzymatic substrate sequence or other consensus sequence).

Initially, the oligopeptide linkage in the nanosensor has a folded secondary structure, such as an alpha-helix and/or beta-sheet structure, so that the detectable particle is separated from the central carrier particle (and quencher particle at the carrier particle's surface) by a first distance. In the presence of the target protein, such as a cytokine, the protein binds to the supramolecular recognition sequence in the oligopeptide modifying the secondary structure of the oligopeptide sequence, such that it linearly extends or unfolds, and thus changes the distance of the second particle to the central carrier particle (and quencher particle). Accordingly, after being exposed to the target protein, the detectable particle is then separated from the central carrier particle (and quencher particle) by a second distance that is greater than the first distance in the initial nanosensor. The detectable particle generates a detectable signal that changes depending upon its proximity to the carrier particle or quencher particle, and which can be detected and correlated with activity of the target protein.

The central carrier particle can be a variety of particles discussed herein, with the proviso that it can be attached with two or more different particles. Preferably, the nanosensor comprises a plurality of quencher particles attached to a single central carrier particle, and a plurality of detectable particles attached to the same carrier particle via respective oligopeptide linkages. Preferably, the amount of quencher particles attached to the carrier particle is greater than the amount of detectable particles tethered to the carrier particle. In one or more embodiments, the ratio of the number of quencher particles (directly attached) to detectable particles (tethered) on each carrier particle is from about 1:1 to about 1:100, more preferably from about 1:1.5 to about 1:35, and more preferably about 1:35. In one or more embodiments, the central carrier particle is one that is capable of SET (Dipole-surface Energy Transfer), and/or participates in quenching of the detectable signal of one or both of the attached particles (and particularly the second particle). In one or more embodiments, the central carrier particle does not actively participate in the signal being detected in the assay, but is simply a carrier structure for tethering the first and second particles. Non-plasmonic particles can be used in certain embodiments.

The detectable particles generate a detectable signal (e.g., optical or spectroscopic), such as fluorescence or color change, which can be perceived visually or measured with an appropriate instrument. In one or more embodiments, the quencher and detectable particles are selected to show intense FRET in the pair. In one or more embodiments, the quencher and detectable particles are paired so as to enhance the SET quenching of the carrier particle.

The nanosensors are particularly suitable for detection methods based upon surface plasmon resonance and FRET between non-identical particles (i.e., nanoparticles or a dye and porphyrin, or two different dyes). FRET describes energy transfer between two particles. Surface plasmon resonance is used to excite the particles. A donor particle initially in its excited state, may transfer this energy to an acceptor particle in close proximity through nonradiative dipole-dipole coupling. Briefly, while the detectable particle is bound by the oligopeptide in its initial state, a first emission is observed upon excitation of the donor particle. Once the peptide binds to the supramolecular recognition sequence, FRET change is observed, and the emission spectra changes. In some instances, only the donor emission is observed. In other instances, the emission spectra simply changes (increases or decreases). In more detail, if both particles are within the so-called Förster-distance, energy transfer occurs between the two particles and a red-shift in emission is observed. During this ultrafast process, the energy of the electronically excited state or surface plasmon of the second particle is at least partially transferred to the first particle. In some embodiments, this means that a detectable signal (e.g., fluorescence, light) is actually emitted from the quencher particle. However, once the distance between the two particles is changed by the enzyme, light is emitted only from the detectable particle and a distinct blue-shift in absorption and emission can be observed. This is because the distance between both particles increases. In other embodiments, a signal may be detectable from both particles in the initial nanosensor, however, upon modification of the substrate sequence, the signal intensity from the detectable particle increases as the distance between the two particles increases.

In one or more embodiments, the quencher particle (directly attached to the central particle) is an acceptor and the detectable particle (tethered via the oligopeptide) is a donor. In general, excitation of the nanosensor is directed towards the particle having a higher energy state (e.g., the donor particle). Excitation of the detectable particle can preferably performed between about 400 nm and about 1500 nm, more preferably between about 500 nm to about 800 nm, and even more preferably between about 650 nm and about 800 nm. When using chromophore/luminophore particle pairs, there is also preferably an overlap between the excitation spectrum of the first chromophore/luminophore and the fluorescence or phosphorescence spectrum of the second chromophore/luminophore to permit adequate Förster energy transfer. In one embodiment, cyanine 5.5 (donor) and cyanine 7.0 (acceptor) form a very attractive FRET-pair.

In the assay, so-called Förster-distance, energy transfer occurs between the quencher and detectable particles and a change in absorbance and/or emission of the nanoplatform is observed. During this ultrafast process, the energy of the electronically excited state or surface plasmon of the detectable particle is at least partially transferred to the quencher particle. Excitation is preferably performed with an energy source of appropriate wavelength selected from the group consisting of a tungsten lamp, laser diode, laser, and bioluminescence (e.g., luciferase, renilla, green fluorescent protein). The changes in absorption and/or emission of the particles as the peptide binds (without cleaving or chemically modifying) the oligopeptide linkages will be observed over a time period of from about 1 second to about 120 minutes, preferably from about 1 second to about 30 minutes, and in some cases from about 30 seconds to about 10 minutes, depending upon protein activity.

In practice, the assay can first be calibrated for the particular nanosensor using a control sample with and without the target proteins, as described in the working examples. For storage and/or use, the nanosensors would typically be dispersed into a pharmaceutically acceptable solvent system, which could be any type of suitable diluent, excipient, vehicle or the like. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the nanoplatform other agents and to minimize any adverse side effects in the subject (for in vivo administration), as would be well known to one of skill in the art. Pharmaceutically-acceptable ingredients include those acceptable for veterinary use as well as human pharmaceutical use, and will depend on the route of administration. For example, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), or other acceptable vehicles, and the like.

In one or more embodiments, the nanosensors are particularly suited for detecting cytokines. The oligopeptide linkage comprises a linear supramolecular recognition sequence (i.e., paratope) for the receptor/binding site of the cytokine of interest. In the presence of the cytokine, stretching of the tether during cytokine binding leads to a signal change (e.g., fluorescence increase) from the attached detectable particle, which can be detected. The nanosensors can measure cytokine concentrations. However, this technology can be extended to virtually any protein target of interest. That is, one advantage of the inventive nanosensors is the flexibility to adapt the underlying nanosensor structure by modifying the particles, oligopeptide linkages, and the like to suit the sensor technology available, and likewise, using a variety of sensor technologies for detecting additional targets. For example, a similar nanosensor can be prepared for detecting protease activity, similar to described in U.S. Pat. No. 8,969,027, except that a quencher particle is directly attached to the central carrier particle as described herein to enhance the detectable signal, see FIG. 4A. Likewise, methods described herein can also be adapted for use with other nanosensors, such as those described in WO 2016/149637 for detection of enzymatic posttranslational modification, see FIG. 4B. Exemplary supramolecular recognition sequences are listed in Table 1 below.

TABLE 1

Supramolecular Recognition Sequences for the Detection of Protein Targets

| | Recognition Sequence(s) | SEQ ID NO: | Accession No. | LOD* Moles/L |
|---|---|---|---|---|
| Cytokine/Chemokine Targets | | | | |
| CCL 2 | CQEQFWW | 1 | P13500 | 10-14 |
| MCP-1[a] | PYFPRGSSYQGWN | 2 | P13500 | 10-15 |
| CCL 3 | CCIQNQ | 3 | P10147 | 10-15 |
| CCL 4 | AWYQPQFE | 4 | P13236 | 10-14 |
| CCL 21 | EQQKRN | 5 | O00585 | 10-15 |
| CXCL 2 | CNHGKFYC | 6 | P19875 | 10-14 |
| CXCL 5 | NIYCNIAY | 7 | P42830 | 10-13 |
| CXCL 8 (IL-8) | KAYRWEFI | 8 | P10145 | 10-16 |
| CXCL 9 | IQNSGAPCH | 9 | Q07325 | 10-15 |
| HSP 27 | WQEAKNANQM | 10 | Q5S1U1 | 10-15 |
| HSP 70 | RHQKTYSF | 11 | P0DMV8 | 10-15 |
| HSP 90 | XLPPHWAGAL | 12 | P02829 | 10-15 |
| MIF | XLPPHWAFAL | 13 | P14174 | 10-15 |
| Calprotectin | LTELEKALNSIIDVYHKYSLIKGNFHAV | 14 | S100A9 | 10-14 |
| CCL20[b] | GESMNFSDVFDSSEDYFVSVNTSYYSVDSE | 15 | P78556 | 10-15 |
| | GTQWWVVCQQFG | 16 | | |
| GCSF[c] | PGHWSDWSPS | 17 | P09919 | 10-15 |
| IL-6 | YFPEPVTVSGAGTFPAVLGSGQPPGKGL | 18 | P05231 | 10-16 |
| | TAVYYCANRAGWGMGDYWGQGTQVT | 19 | | |
| | TASNYGAGYSTNDRHS | 20 | | |
| | NRPAQAWMLG | 21 | | |
| IL-13 | AVYYCQQNNEDPRTFGGGTK | 22 | P35225 | 10-15 |
| | AGDGYYPYAMDNW | 23 | | |
| | GWLPFGFILISAG | 24 | | |
| | YQQKPGQPPKL | 25 | | |
| | SVNWIRQPPGKALEWLAMIWGDGKIVYNS | 26 | | |
| | WLPFGFILIS | 27 | | |
| IL1RL1[d] | TYYCQQWSGYPYTF | 28 | P14778 | 10-15 |
| MIP-1[e] | SHFPYSQYQFWKN | 29 | Q9BPZ7 | 10-15 |
| OSTF1[f] | DMSDTNWWKGTSKGRTGLIPSNYVAEQA ESIDNPL | 30 | Q92882 | 10-15 |
| TIMP-1[g] | IAGKLQSAGSALWTDQL | 31 | P01033 | 10-12 |
| TSLP[h] | SSPKHVRFSWHQDAVTVTC | 32 | Q960D9 | 10-14 |
| | AKCCPCQQWW | 33 | | |
| Peptide Aptamers-Exosome surface markers | | | | |
| CD-9[i] | VQEFYKDTYNKLKTK | 34 | P21926 | 10-14 |
| CD-63[i] | LNNHTASILNRMQANF | 35 | P08962 | 10-14 |
| CD-81[i] | VGIYILIAVGAVMMFVGFK | 36 | P60033 | 10-15 |
| Exosome content analysis-markers of lung inflammation | | | | |
| O00571[j] | NERNINITKDLLDLLVAH | 37 | O00571 | 10-14 |
| P05187[k] | DINWVKQRPGQGLEWI | 38 | P05187 | 10-15 |
| P54136[l] | VLLQGKNPDITKAWKL | 39 | P54136 | 10-15 |
| Q5T4S7[m] | NLSRSRWFDFPFTREE | 40 | Q5T4S7 | 10-14 |

[a]Monocyte Chemoattractant Protein-1;
[b]Chemokine (C-C motif) ligand 20 (CCL20) or liver activation regulated chemokine (LARC) or Macrophage Inflammatory Protein-3 (MIP3A);
[c]Granulocyte colony-stimulating factor;
[d]Interleukin-1-receptor-like type 1;
[e]Macrophage Inflammatory Protein;
[f]Osteoclast Stimulating Factor-1;
[g]Metalloproteinase Inhibitor 1;
[h]Thymic stromal lymphopoietin;
[i]CD: Cluster of Differentiation;
[j]ATP-dependent RNA helicase DDX3X (from human bronchial airway epithelial cells);
[k]Alkaline phosphatase, placental type, phosphatase PPB1;
[l]Arginine-tRNA ligase, cytoplasmic;
[m]E3 ubiquitin-protein ligase UBR4 (small airway epithelial cells);
*Estimated limit of detection (LOD).

The supramolecular recognition sequences can include one or more spacer residues on the N- and/or C-terminal ends. For example, between 1 and 10 amino acids (any amino acids, naturally and non-naturally, L- and D-, or combinations thereof) can be used at one or both ends as spacers. Examples include N-terminal sequences such as GAG- and C-terminal sequences such as -AG.

Any other linear peptide sequence of suitable length (e.g., at least 10 amino acid residues) can be used for the supramolecular recognition sequences, with the exception of sequences featuring consensus motifs. If synthesized on a peptide synthesizer, peptide sequences up to about 25 amino acid residues can be used, whereas sequence synthesized in an organism (e.g., *E. coli*) can be up to about 300 amino acid residues in length. Any designed sequence should to be checked for the presence of cleavage sequences, utilizing a data bank, such as MEROPS.

As noted, peptide-aptamers for targeting CD9, CD63, and CD81, which are generally accepted surface markers of exosomes have also been developed. They are capable of binding to the exosomes and permit their isolation directly from collected biospecimens using the nanosensors without prior (ultra)centrifugation. The combined use of CD9, CD63, and CD81 will ensure that virtually all exosomes occurring from the sample, such as from airway cells, will be trapped. After treatment with a lysis buffer, the cargo of the captured exosomes can then be analyzed. Analysis of exosomes presents another existing aspect of the technology. Exosomes occurring from small airway epithelial cells and bronchial airway epithelial cells differ significantly in their proteasomes (including the tetraspanin content (CD9, CD 63, CD81) in their outer membranes.

Enzyme consensus sequences that can also be used in nanosensors in combination with one or more above include those in Table 2 below, where the cleavage point is indicated by the

TABLE 2

| Enzyme | Consensus Sequence | SEQ ID NO: | Accession No. |
|---|---|---|---|
| ADAM 17 | LAQA-VVSS | 41 | P78536 |
| ADAM 33 | GSQH-IRAE | 42 | Q9BZ11 |
| Cathepsin B | SLLKSR-MVPNFN | 43 | P07858 |
| Cathepsin D | GDSG-LGRA | 44 | P07339 |
| Cathepsin E | EVAL-VALK | 45 | P14091 |
| Cathepsin K | LGLE-GANL | 46 | P43235 |
| Cathepsin L | AALG-SAPG | 47 | P07711 |
| Cathepsin S | SLLIFR-SWANFN | 48 | P25774 |
| Granzyme B | VEPN-SLEE | 49 | P10144 |
| NE | GEPL-SLLP | 50 | P08246 |
| MMP 1 | IPVS-LRSG | 51 | P03956 |
| MMP 2 | IPVS-LRSG | 51 | P08253 |
| MMP 3 | RPFS-MIMG | 52 | P08254 |
| MMP 7 | VPLS-LTMG | 53 | P09237 |
| MMP 8 | GPSG-LRGA | 54 | P22894 |
| MMP 9 | VPLS-LYSG | 55 | P14780 |
| MMP 11 | GAAN-LVRG | 56 | P24347 |
| MMP 12 | GVPLS-LTMG | 57 | P34960 |
| MMP 13 | PQGLA-GQRGIV | 58 | P33435 |
| MMP 14 | GPAG-LRLA | 59 | P50281 |
| ALK | RDIYAAPFFRK | 60 | Q9UM73 |
| AURKB | AMERRRTSAARRSY | 61 | Q96GD4 |
| CDK2 | KARAAVSPQKRKA | 62 | P24941 |
| PKD2 | RARKRRLSAPPLASGD | 63 | Q504Y2 |
| MAPK1 | AKAGPPLSPRPPHVH | 64 | P28482 |
| JAK2 | DLFIPDNYLKMKPAP | 65 | O60674 |
| PLK1 | AELDPEDSMDMDAP | 66 | P53350 |

TABLE 2 -continued

| Enzyme | Consensus Sequence | SEQ ID NO: | Accession No. |
|---|---|---|---|
| PLK3 | EDEAEELSDEDEELK | 67 | Q9H4B4 |
| ERK1/MAPK3 | AAGPAPLSPVPPVVH | 68 | P27361 |
| JunK2/MAPK9 | DASRPPPLSPLPSPRA | 69 | P45984 |
| ARG I/II | GRRRRRRG | 70 | P05089 (ARG1) P78540 (ARG2) |

In a further preferred embodiment of the current invention, inflammatory biological markers can be detected along with detection of specific viral, bacterial, or mold infections. For example, nanosensors could be prepared using a peptide aptamer against Capsid B (AISGSGGSTYYANSVLG (SEQ ID NO:71), recognition sequence for detecting *Haemophilus influenzae* B, or recognition sequences for *Haemophilus influenzae* NT (TNLGILHSMVARAVGNNTQG (SEQ ID NO:72)), or *Moraxella catarrhalis* (GIITY-ALSGGEIKILAG (SEQ ID NO:73)). Likewise, nanosensors for viral infections can be prepared using protease consensus sequences for HIV detection (SAVL-LEAT (SEQ ID NO:74), or SQNY-PIVQ (SEQ ID NO:75)).

It will be appreciated that each of the foregoing sensors described above can be designed in an alternative configuration where the detectable particle is attached to the central carrier particle in a "permanent" manner (e.g., via non-cleavable peptide sequence), whereas the quencher particle is attached via a supramolecular recognition sequence, a protease consensus sequence, a post-translationally modifiable sequence, or a sterically hindered benzylether bond that interacts with the target biomarker. In such embodiments, while the detectable particle remains relatively stationary and affixed to the carrier particle, the quencher particle is instead either cleaved or moved away from the detectable particle and carrier particle, to effect the change in distance between the particles, as described above. As noted, the increase in distance between the quencher particle and the detectable particle (from cleavage or elongation of the quencher particle tether) results in a detectable change in the signal from the nanosensor.

Figure 3:
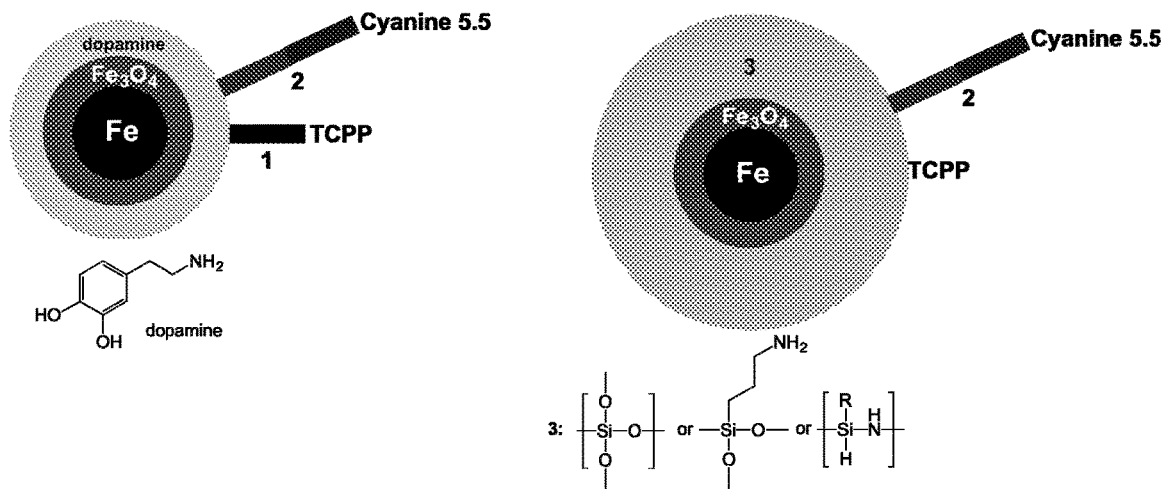
FIG. 3 is a cartoon illustration of an inverse nanosensor in accordance with an embodiment of the invention, in which the detectable particle is directly attached to the central carrier particle (e.g., via short dopamine spacer or designer polymer), while the quencher particle is tethered via a cleavable linkage.

Alternative embodiments of the invention concern "inverse" nanosensors from protease sensors discussed here, and illustrated in FIG. 3. When using a microfluidic-based device, such as paper microfluidic devices, the detectable particle will generally be cleaved off when enzymatic activity is detected. However, it would be desirable if the detectable signal occurring from this particle would occur from a constrained site on the test strip. Therefore, we have constructed the "inverse nanoplatforms for protease detection", in which the detectable particle is linked to the carrier particle by a short (e.g., 1.4-1.5 nm) peptide sequence. At this distance from the carrier particle (e.g., in the case of Fe/Fe$_3$O$_4$ nanoparticles: Fe core diameter 13+/−0.5 nm; shell diameter 2.0+/−1 nm, dopamine layer~1 nm) their plasmonic scattering is highest and, therefore, the fluorescence of the detectable particle is enhanced. Upon cleavage, the fluorescence decreases, not increases.

Another alternative embodiment involves a nanosensor to detect Hydrogen Sulfide (H$_2$S). H$_2$S has been recently established as powerful biomarker for chronic respiratory diseases, based on significant metabolic differences between healthy human subjects and patients with asthma or chronic obstructive pulmonary disease (COPD). In an exemplary embodiment, the nanosensor is utilized for measuring the H$_2$S concentration in biospecimens. The design of the nanosensor is based on the fact that the hydrogen sulfide anion (HS$^-$) is the predominant species under physiological conditions (approx. 80% at 37° C. and pH=7.4). HS$^-$ is a potent nucleophile that readily reacts with metal centers (for instance in coenzymes). The distinctly higher nucleophilicity of HS$^-$ will be utilized to differentiate this biological marker from cysteine, methionine, glutathione and cysteine-containing peptides and proteins. The approach is similar to the protease sensors discussed above. A detectable particle is tethered to a central carrier particle via a cleavable sterically hindered benzyl ether bond (i.e., with adjacent carbons substituted with methyl, ethyl, propyl, isopropyl, butyl, isobutyl, tert-butyl, etc.). Nucleophilic cleavage of the bond releases the detectable particle, and the associated change in the nanosensor can be detected.

Figure 4:
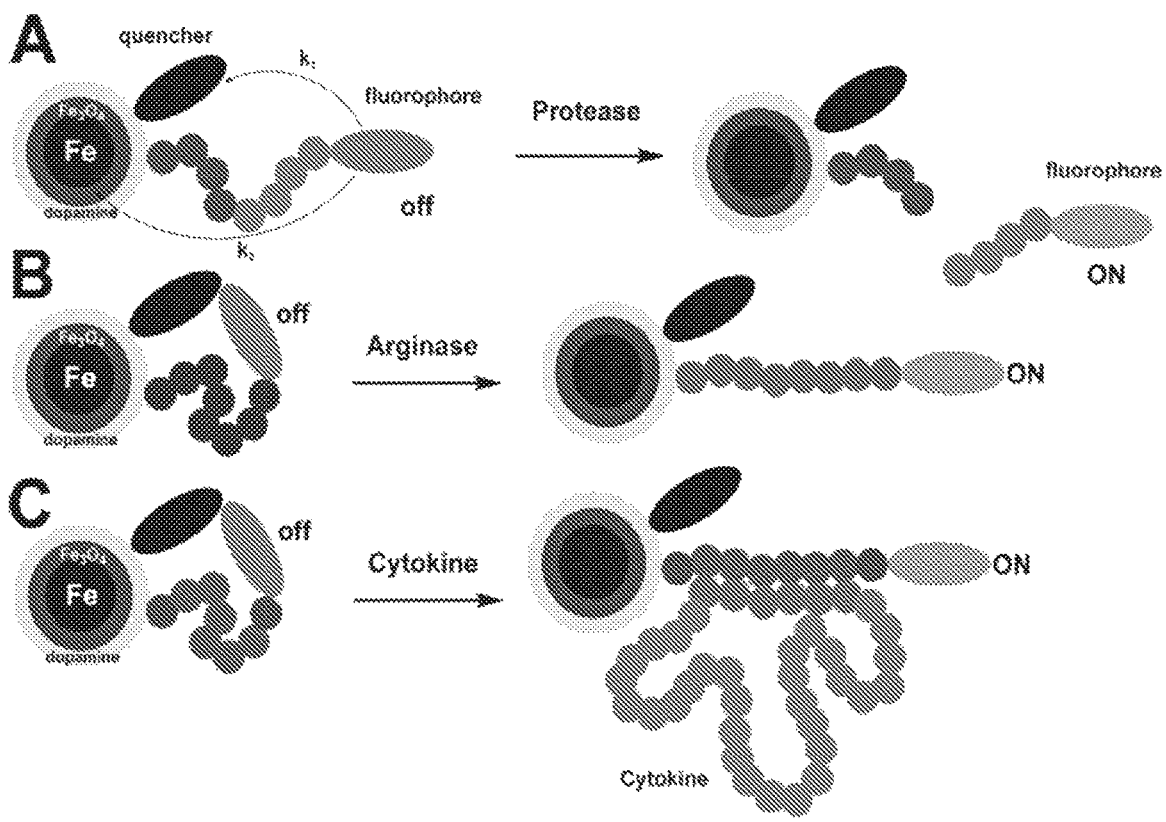
FIG. 4 is a cartoon illustration of different nanosensor types that can be used in the microfluidics devices, including (A) protease sensors; (B) arginase sensors; and (C) cytokine sensors.

It will be appreciated that assays according to the invention can utilize a combination of two or more of the various sensors discussed above. Importantly, nanosensors utilized in accordance with the invention will be designed to include a supramolecular recognition sequence, a protease consensus sequence, a post-translationally modifiable sequence, or a sterically hindered benzylether bond that gives rise to a specific interaction with a biological marker. As used herein, references to "specific interactions" (and the like) is intended to differentiate the inventive sensors from non-specific binding or reactions between molecules, and means that the set of specific target analytes for which the oligo-peptide sequence can interact is limited, and in some cases even exclusive, such that neither binding nor enzymatic cleavage occurs at an appreciable rate with any other molecule. The mechanism for these preferred configurations of nanosensors is illustrated in FIG. 4.

Particles for Nanosensors

A number of different types of particles can be used to form the nanosensors, depending upon the type of sensor used to measure the target's activity, as discussed in more detail below. Preferably, the excitation and emission spectral maxima of the particles are between 650 and 800 nm. Preferred particles for use in the nanosensors are selected from the group consisting of nanoparticles, chromophores/luminophores, quantum dots, viologens, and combinations thereof.

1. Nanoparticles

The term "nanoparticle" as used herein refers to nanocrystalline particles that can optionally be surrounded by a metal and/or nonmetal nanolayer shell. Such nanoparticles can be metal nanoparticles: metal, metal alloy, metal oxide, or core/shell metal nanoparticles (e.g. Fe$_2$O$_3$, Fe$_3$O$_4$). Metal nanoparticles can alternatively be surrounded by a second shell of silica, as described in U.S. Pat. No. 8,877,951, incorporated by reference herein to the extent not inconsistent with the present disclosure. Depending on the chemical composition of the nanoparticles and their actual size, the optimal distance between plasmonic core and shell can be determined experimentally.

Suitable nanoparticles preferably have a diameter of from about 1 nm to about 100 nm, more preferably from about 10 nm to about 50 nm, and even more preferably from about 5 nm to about 20 nm. Metal nanoparticles can comprise any type of metal (including elemental metal) or metal alloy. Preferably, the metal or metal alloy nanoparticles comprise a metal selected from the group consisting of gold (Au), silver (Ag), copper (Cu), nickel (Ni), palladium (Pd), platinum (Pt), cobalt (Co), rhodium (Rh), iridium (Ir), iron (Fe), ruthenium (Ru), osmium (Os), manganese (Mn), rhenium (Re), scandium (Sc), titanium (Ti), vanadium (V), chromium (Cr), zinc (Zn), yttrium (Y), zirconium (Zr), niobium (Nb), molybdenum (Mo), technetium (Tc), cadmium (Cd), lanthanum (La), lutetium (Lu), hafnium (Hf), tantalum (Ta), tungsten (W), actinium (Ac), lawrencium (Lr), rutherfordium (Rf), dubnium (Db), seaborgium (Sg), bohrium (Bh), Hassium (Hs), meitnerium (Mt), darmstadtium (Ds), roentgenium (Rg), ununbium (Uub), selenium (Se), and the oxides (e.g., FeO, $Fe_3O_4$, $Fe_2O_3$, $Fe_xO_y$ (non-stoichiometric iron oxide), CuO, NiO, $Ag_2O$, $Mn_2O_3$), hydroxides, sulfides, selenides, and tellurides of the foregoing, and combinations thereof.

In some embodiments, metal nanoparticles will be bimagnetic and comprise a metal or metal alloy core and a metal shell. Core/shell metal nanoparticles preferably comprise a metal or metal alloy core and a metal shell. Preferred cores are selected from the group consisting of Au, Ag, Cu, Co, Fe, and Pt. Even more preferably, the metal nanoparticles feature a strongly paramagnetic Fe core. Preferred shells are selected from the group consisting of Au, Ag, Cu, Co, Fe, Pt, the metal oxides (e.g., FeO, $Fe_3O_4$, $Fe_2O_3$, $Fe_xO_y$ (non-stoichiometric iron oxide), CuO, $Cu_2O$, NiO, $Ag_2O$, $Mn_2O_3$) thereof, and combinations thereof. Particularly preferred metal core/shell combinations are selected from the group consisting of Fe/Au, Fe(0)/$Fe_3O_4$, and Au/$Fe_2O_3$. A particularly preferred metal nanoparticle is a superparamagnetic Fe/$Fe_3O_4$ core shell nanoparticle. More preferably, the nanoparticles feature an iron(0) core, which is more magnetic than iron oxide, based upon coercivity. This means that smaller nanoparticles can be used (diameter less than about 10 nm), which have the same or greater magneticity than larger iron oxide nanoparticles (diameter of about 200 nm).

In one or more embodiments, the core of the metal nanoparticle preferably has a diameter of from about 2 nm to about 100 nm, more preferably from about 3 nm to about 18 nm and more preferably from about 5 nm to about 9 nm. The metal shell of the core/shell nanoparticle preferably has a thickness of from about 1 nm to about 10 nm, and more preferably from about 1 nm to about 2 nm. The nanoparticles preferably have a Brunauer-Emmett-Teller (BET) multipoint surface area of from about 20 $m^2/g$ to about 500 $m^2/g$, more preferably from about 50 $m^2/g$ to about 350 $m^2/g$, and even more preferably from about 60 $m^2/g$ to about 80 $m^2/g$. The nanoparticles preferably have a Barret-Joyner-Halenda (BJH) adsorption cumulative surface area of pores having a width between 17.000 Å and 3000.000 Å of from about 20 $m^2/g$ to about 500 $m^2/g$, and more preferably from about 50 $m^2/g$ to about 150 $m^2/g$. The nanoparticles also preferably have a BJH desorption cumulative surface area of pores having a width between 17.000 Å and 3000.000 Å of from about 50 $m^2/g$ to about 500 $m^2/g$, and more preferably from about 50 $m^2/g$ to about 150 $m^2/g$. The nanoparticle population is preferably substantially monodisperse, with a very narrow size/mass size distribution. More preferably, the nanoparticle population has a polydispersity index of from about 1.2 to about 1.05. It is particularly preferred that the nanoparticles used in the inventive nanoplatforms are discrete particles. That is, clustering of nanocrystals (i.e., nanocrystalline particles) is preferably avoided.

The nanoparticles can be stabilized or non-stabilized. Stabilized nanoparticles preferably comprise an organic monolayer surrounding the nanoparticle core. The term "stabilized" as used herein means the use of a ligand shell or monolayer to coat, protect (e.g., from bio-corrosion), or impart properties (e.g., water solubility) to, the nanoparticle. The monolayer can be comprised of several of the same ligands (i.e., homoligand) or of mixed ligands. Various techniques for attaching ligands to the surface of various nanoparticles are known in the art. For example, nanoparticles may be mixed in a solution containing the ligands to promote the coating of the nanoparticle. Alternatively, coatings may be applied to nanoparticles by exposing the nanoparticles to a vapor phase of the coating material such that the coating attaches to or bonds with the nanoparticle. Preferably, the ligands attach to the nanoparticle through covalent bonding. The number of ligands required to form a monolayer will be dependent upon the size of the nanoparticle.

The ligands comprise functional groups that are attracted to the nanoparticle's metal surface. Preferably, the ligands comprise at least one group selected from the group consisting of thiols, alcohols, nitro compounds, phosphines, phosphine oxides, resorcinarenes, selenides, phosphinic acids, phosphonicacids, sulfonic acids, sulfonates, carboxylic acids, disulfides, peroxides, amines, nitriles, isonitriles, thionitiles, oxynitriles, oxysilanes, alkanes, alkenes, alkynes, aromatic compounds, and seleno moieties. Preferred organic monolayers are selected from the group consisting of alkanethiolate monolayers, aminoalkylthiolate monolayers, alkylthiolsulfate monolayers, and organic phenols (e.g., dopamine and derivatives thereof). The thickness of the organic monolayer is preferably less than about 10 nm, and more preferably less than about 5 nm. Particularly preferred stabilized nanoparticles are selected from the group consisting of trioctyl-phosphinoxide-stablized nanoparticles, amine-stabilized nanoparticles, carboxylic-acid-stabilized nanoparticles, phosphine-stabilized nanoparticles, thiol-stabilized nanoparticles, aminoalkylthiol-stabilized nanoparticles, and organic phenol-stabilized nanoparticles.

For attachment to the oligopeptide linkages, the preferred ligands will preferably readily react with the thiol group of the terminal cysteine of the oligopeptide linkage. The nanoparticle surface will preferably be essentially completely covered with ligands. That is, at least about 70%, preferably at least about 90%, and more preferably about 100% of the surface of the nanoparticle will have attached ligands. The number of ligands required to form a monolayer will be dependent upon the size of the nanoparticle (and monolayer), and can be calculated using molecular modeling or ligand modeling methods.

Various techniques for attaching ligands to the surface of various nanoparticles are known in the art. For example, nanoparticles may be mixed in a solution containing the ligands to promote the coating of the nanoparticle surface. Alternatively, coatings may be applied to nanoparticles by exposing the nanoparticles to a vapor phase of the coating material such that the coating attaches to or bonds with the nanoparticle. Preferably, the ligands attach to the nanoparticle through covalent bonding.

Figure 5:
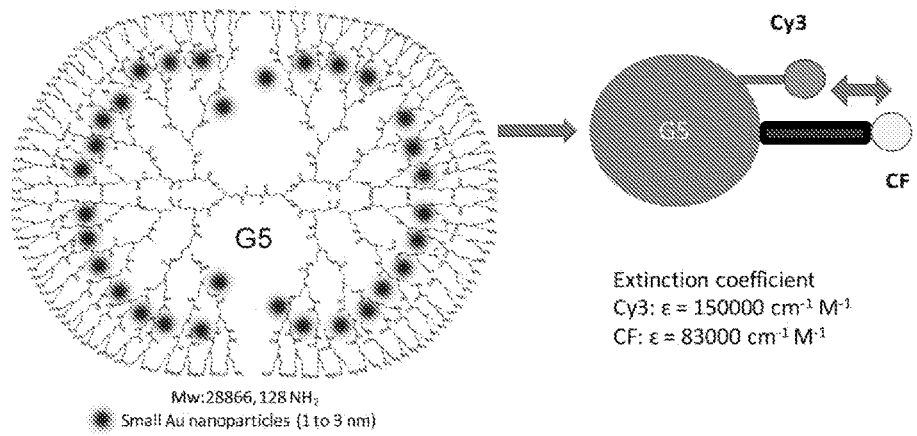
FIG. 5 is an illustration of a nanosensor using a starburst dendrimer containing gold nanoparticles in accordance with embodiments of the invention.

Nanoparticles can also be non-metal: non-metal oxide (e.g. $SiO_2$), polysilicone, polysilazane, or polysiloxazane, starburst dendrimers, or polymer latex nanoparticles. For example, in one or more embodiments, it is possible to replace the carrier nanoparticle with a starburst dendrimer or starburst dendrimer containing gold nanoparticles, as illustrated in FIG. 5. Poly-(amidoamine) (PAMAM) dendrimers have defined three-dimensional shape, size, topology, and peripheral functional groups. What makes PAMAM dendrimers different from other polymers is that PAMAM dendrimers are pure macromolecules, with precise molecular weight for each generation (starburst polymers). Dendrimers can be purchased according to desired specifications. Therefore, it is not necessary to synthesize inorganic nanoparticles. The approach is otherwise the same as described herein. One advantage is that the shelf life for dendrimer-based nanosensors is greater than 5 years. Further, PAMAM dendrimer stick to cellulose, and can be printed directly onto paper. This would facilitate mass fabrication of paper microfluidic devices by applying inexpensive desk jet printing technology, as described herein.

2. Chromophores/Luminophores

Chromophore/luminophore particles suitable for use in the inventive assays include any organic or inorganic dyes, fluorophores, phosphophores, light absorbing nanoparticles (e.g., Au, Ag, Pt, Pd), combinations thereof, or the metalated complexes thereof. Preferably, the chromophore/luminophore particles have a size (maximum surface-to-surface dimension, i.e., diameter) of less than about 100 nm.

Suitable organic dyes are selected from the group consisting of coumarins, pyrene, cyanines, benzenes, N-methylcarbazole, erythrosin B, N-acetyl-L-tryptophanamide, 2,5-diphenyloxazole, rubrene, and N-(3-sulfopropyl)acridinium. Specific examples of preferred coumarins include 7-aminocoumarin, 7-dialkylamino coumarin, and coumarin 153. Examples of preferred benzenes include 1,4-bis(5-phenyloxazol-2-yl)benzene and 1,4-diphenylbenzene. Examples of preferred cyanines include oxacyanines, thiacyanines, indocyanins, merocyanines, and carbocyanines. Other exemplary cyanines include ECL Plus, ECF, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, CypHer5, Dye-33, cyanines (Cy7, Cy7.5, Cy5.0, Cy5.5, Cy3Cy5 ET, Cy3B, Cy3.0, Cy3.5, Cy2), CBQCA, NIR1, NIR2, NIR3, NIR4, NIR820, SNIR1, SNIR2, SNIR4, Merocyanine 540, Pinacyanol-Iodide, 1,1-Diethyl-4,4-carbocyanine iodide, Stains All, Dye-1041, or Dye-304.

Cyanine dyes are particularly preferred organic dyes for use in the nanoplatforms. The fluorescent cyanine dye is tethered to the nanoparticle and experiences rapid fluorescence quenching by the plasmon of the Fe(0)-core. This is observed as long as the tether is smaller than the Förster-radius of the cyanine dye (5-6 nm for Cy3.0 and Cy3.5, 6-7 nm for Cy5.0 and Cy5.5, and approx. 7 nm for Cy7 and Cy7.5). The maximal length of the tether, consisting of the ligand (~2.84 nm) and not more than 12 amino acid residues in the cleavage sequences (up to 4 nm) indicates that shorter cleavage sequences (uPA and MMP's) are suitable for use with Cy3.x and Cy5.x dyes, whereas the cathepsins are preferably linked to Cy5.x and Cy.7.x dyes to permit optimal quenching of the tethered cyanine dyes. For all of the cyanines, their emission maxima are red-shifted with respect to the autofluorescence of human urine. Multiple cyanines can be linked to a single nanoparticle to create oligoplexing nanoplatforms, to measure the activity of up to four enzymes simultaneously. All four dyes in the UVA or blue region of the electromagnetic spectrum can be excited simultaneously, or each dye can be excited individually. All cyanine dyes have an excitation maximum, which is blueshifted by 20-25 nm with respect to their emission maximum (typical for fluorescent singlet states). Exemplary emission spectra of: NS-Cy3.0 ($\lambda$ex=538, $\lambda$em=560), NS-Cy5.5 ($\lambda$ex=639, $\lambda$em=660), NS-Cy7.0 ($\lambda$ex=740, $\lambda$em=760) and NS-Cy7.5 ($\lambda$ex=808, $\lambda$em=830).

Suitable inorganic dyes are selected from the group consisting of metalated and non-metalated porphyrins, phthalocyanines, chlorins (e.g., chlorophyll A and B), and metalated chromophores. Preferred porphyrins are selected from the group consisting of tetra carboxy-phenyl-porphyrin (TCPP) and Zn-TCPP. Preferred metalated chromophores are selected from the group consisting of ruthenium polypyridyl complexes, osmium polypyridyl complexes, rhodium polypyridyl complexes, 3-(1-methylbenzoimidazol-2-yl)-7-(diethylamino)-coumarin complexes of iridium(III), and 3-(benzothiazol-2-yl)-7-(diethylamino)-coumarin complexes with iridium(III).

Suitable fluorophores and phosphophores are selected from the group consisting of phosphorescent dyes, fluoresceines, rhodamines (e.g., rhodamine B, rhodamine 6G), and anthracenes (e.g., 9-cyanoanthracene, 9,10-diphenylanthracene, 1-Chloro-9,10-bis(phenyl-ethynyl)anthracene).

3. Quantum Dots

A quantum dot is a semiconductor composed of atoms from groups II-VI or III-V elements of the periodic table (e.g., CdSe, CdTe, InP). The optical properties of quantum dots can be manipulated by synthesizing a (usually stabilizing) shell. Such quantum dots are known as core-shell quantum dots (e.g., CdSe/ZnS, InP/ZnS, InP/CdSe). Quantum dots of the same material, but with different sizes, can emit light of different colors. Their brightness is attributed to the quantization of energy levels due to confinement of an electron in all three spatial dimensions. In a bulk semiconductor, an electron-hole pair is bound within the Bohr exciton radius, which is characteristic for each type of semiconductor. A quantum dot is smaller than the Bohr exciton radius, which causes the appearance of discrete energy levels. The band gap, $\Delta E$, between the valance and conduction band of the semiconductor is a function of the nanocrystal's size and shape. Quantum dots feature slightly lower luminescence quantum yields than traditional organic fluorophores but they have much larger absorption cross-sections and very low rates of photobleaching. Molar extinction coefficients of quantum dots are about $10^5$-$10^6$ $M^{-1}$ $cm^{-1}$, which is 10-100 times larger than dyes.

Core/shell quantum dots have higher band gap shells around their lower band gap cores, which emit light without any absorption by the shell. The shell passivates surface nonradiative emission from the core thereby enhancing the photoluminescence quantum yield and preventing natural degradation. The shell of type I quantum dots (e.g. CdSe/ZnS) has a higher energy conduction band and a lower energy valance band than that of the core, resulting in confinement of both electron and hole in the core. The conduction and valance bands of the shell of type II quantum dots (e.g., CdTe/CdSe, CdSe/ZnTe) are either both lower or both higher in energy than those of the core. Thus, the motions of the electron and the hole are restricted to one dimension. Radiative recombination of the exciton at the core-shell interface gives rise to the type-II emission. Type II quantum dots behave as indirect semiconductors near band edges and therefore, have an absorption tail into the red and near infrared. Alloyed semiconductor quantum dots (CdSeTe) can also be used, although types I and II are most preferred. The alloy composition and internal structure, which can be varied, permits tuning the optical properties without changing the particles' size. These quantum dots can be used to develop near infrared fluorescent probes for in vivo biological assays as they can emit up to 850 nm.

Particularly preferred quantum dots are selected from the group consisting of CdSe/ZnS core/shell quantum dots, CdTe/CdSe core/shell quantum dots, CdSe/ZnTe core/shell quantum dots, and alloyed semiconductor quantum dots (e.g., CdSeTe). The quantum dots are preferably small enough to be discharged via the renal pathway when used in vivo. More preferably, the quantum dots are less than about 10 nm in diameter, even more preferably from about 2 nm to about 5.5 nm in diameter, and most preferably from about 1.5 nm to about 4.5 nm in diameter. If different color emission is needed for creating multiple sensors (multiplex detection), this can be achieved by changing the size of the quantum dot core yielding different emission wavelengths. The quantum dots can be stabilized or unstabilized as discussed above regarding nanoparticles. Preferred ligands for stabilizing quantum dots are resorcinarenes.

Methods

Methods for noninvasive detection and quantification of various biological markers are also described herein. These methods utilize nanosensors described herein and can be carried out in health care facilities as an integral part of point of care resources, at home or in the field for assessing biological markers indicative of acute injury as well as chronic conditions.

Such biological marker-based diagnostics could have numerous applications in precision medicine, particularly for airway diseases, where the availability of point of care devices could lead to the development of personalized treatment strategies for individual patients based on the assessment of the temporal and spatial distributions of inflammatory markers of the airways. Because protein signatures in airways are not well reflected in circulating blood, the initial diagnostic would involve, in some aspects, sampling fluids from the airways using nasopharyngeal washes (in children), induced sputum, bronchoalveolar lavage, exhaled breath condensates, and the like. Biological samples for other conditions include other biological specimens and fluids, such as blood, urine, saliva, tears, sputum, bronchoalveolar lavage fluid, breath condensate, feces, rectal fluid, vaginal fluid, and the like. In one aspect, a biological sample is collected from a subject and prepared for analysis. The sample can be collected and prepared manually, which includes, for example, manual pipetting of sample, manual protein spot cutting, manual biopsy collection, manual blood draw, and manual microfluidic chip loading. Alternatively, and automated process can be used, which includes, for example, use of automated liquid handlers, automated protein spot cutters, automated biopsy collection, automated blood draws, and automated microfluidics chip loading. It will be appreciated that the biological sample contains secreted proteins, micro-vesicle proteins, exosomes and components thereof, including but not limited to RNA and DNA, enzymes, and the like, which can be used as biological markers indicative of the health status of the subject.

Once the biological sample has been collected, the same can be subjected to additional processing for analysis. For example, manual processing approaches can be used including, but is not limited to, manual transfer, manual mixing, and manual phased extraction of samples and chemical components. It will also be appreciated that automated processing approaches can also be used, including, but not limited to, the use of automated liquid handling devices for sample and chemical component transfer, mixing, and phased extraction. In a further preferred embodiment of the current invention, the automated processing step utilizes an automated microfluidics device for sample and chemical component transfer, mixing, and phased extraction. In general, the biological sample will be a liquid biospecimen. In one or more embodiments, the sample is mixed with a pharmaceutically acceptable buffer solution to yield a liquid biospecimen for analysis. In one or more embodiments, the sample (regardless of whether initially in liquid form) is mixed with a solution containing metal cofactors or other components to preserve enzymatic and protein activity in the sample during the processing and analysis.

For micro-vesicle proteins just as exosomes, additional sample processing steps may be required for target detection. In a preferred embodiment of the current invention, exosome surface recognition elements are used to isolate exosomes from the other biological material sample content. The surface recognition elements include, but are not limited to, exosome specific protein markers including tetraspanins (e.g., CD9, CD37, CD53, CD63, CD81 and CD82), endosome associated proteins (e.g., small Rab family GTPases, annexins and flotillin), proteins involved in exosome biogenesis (e.g., Alix, Tsg101 and ESCRT complex), heat shock proteins (Hsp70, Hsp90) and epithelial cell adhesion molecules (EpCam). Magnetic capture methodologies are used to capture the exosomes using fixed attachment of the corresponding surface recognition binding sequence. For example, magnetic nanoparticle-based nanosensors (i.e., magnetic capture nanosensors) can initially be used for isolation and capture of exosomes with supramolecular recognition binding sequences in the sensors that recognize and bind to exosome surface proteins. The nanosensors (containing bound exosomes) can then be filtered, for example, using magnets to remove the nanosensors from surrounding materials. Once the exosomes have been magnetically captured onto a plate, chip, or other collection vehicle, the exosomes are lysed to expose their cargo for further processing, profiling, and target detection. In an embodiment of the current invention, exosome lysis utilizes a plurality of methods such as, but not limited to heat, electromagnetic, acoustic, chemical, photonic, or combination thereof to achieve lysis. It will be appreciated that isolation and lysing of the exosomes may be carried out on the same microfluidics device, for example, in a microfluidics channel capture region "upstream" of the detection region. It may also be carried out in a separate microfluidics device, before subsequent introduction of the lysed exosomes into the analysis device. Further, conventional isolation and capture techniques can be used before the exosomes are assessing using the technology.

It is also noted that surface proteins can be used as biomarkers related to cancer diagnosis. Thus, it is not always necessary to lyse the captured exosomes, as the surface biomarkers themselves can be used for analysis of the sample.

It will be appreciated that the foregoing techniques related to preparing the exosomes for analysis has a distinct advantage over existing exosome processing techniques. Namely, current techniques rely on high-speed centrifugation and often damage the exosomes or significantly increases their fragility (which hampers additional manipulation or analysis). The inventive approach is, by contrast, relatively gentle, and preserves the functionality of the exosomes (and their contents).

Once the biological markers are prepared, the method proceeds to detection. In one or more embodiments, nanosensors according to embodiments of the invention are used for detection and identification of biological markers in the sample. The nanosensors are designed and/or selected based upon the desired target marker selected for detection. For example, the nanosensors can be used to diagnose lower respiratory tract infections by detecting markers associated with infected lower airway epithelial cell infection. These markers include CCL20, TSLP, and CCL3-L1. As noted herein, exosome contents can be used to determine whether the exosomes originated from the upper or lower airway, and further assist in localization of where the infection or other condition may originate from in the subject's body. The nanosensors can also be used for environmental risk assessment in patients with chronic lung disease. Exposure to air pollutants, ozone, particulates, acetaldehydes, acreleine, formaldehyde, tobacco smoke and other compounds triggers inflammation of the respiratory tract. Detection of markers such as cytokines, proteases, and/or kinases can be used to identify the stage at which lower respiratory tract inflammation is manifest, allowing for personalized environmental assessment. The nanosensors can also be used for measurement of lower respiratory tract inflammation in the real-time management of inflammation in asthma. Details regarding biological markers and understanding of protein expression patterns associated with severe asthma are described in U.S. Pat. No. 8,053,199, incorporated by references herein. Currently anti-inflammatory (corticosteroids, IL-13 antibodies and others) are given and monitored on the basis of symptoms and exacerbations. By testing for lower airway markers such as cytokines, proteases, and/or kinases patients and caregivers can track inflammation in real time and adjust treatments accordingly. Similarly, the nanosensors can be used for measurement of lower airway remodeling in severe asthma and chronic obstructive lung disease (COPD). Remodeling refers to the process of fibrosis of the respiratory tract, a process linked to progressive decline in lung function in a subset of patients with severe asthma and COPD. There is no treatment or diagnostic currently available. New therapies directed towards epigenetic remodeling are currently being developed. Our method will enable the development and approval of remodeling inhibitors for clinical use by detecting and measuring the presence of fibronectin, IL6, or vimentin, as indicative of progressive airway remodeling.

Opportunistic infections are also a significant complication in patients being treated for cancer, immunosuppressed through treatment of rheumatoid arthritis or inflammatory bowel disease, or those with HIV. Pneumocystis pneumonia (PCP) is the most common infection of HIV patients, and can only be diagnosed currently by invasive bronchoscopy. Invasive aspergillosis is also an opportunistic lung infection occurring in patients undergoing chemotherapy for leukemia. The nanosensors can be used to indicate the presence of distinct host response proteins when the fungus invades the airway in patients immunosuppressed from their leukemia treatment.

The nanosensors can also be used for monitoring for transplant rejections or host versus graft disease in lung transplants. Lung transplant patients are treated with intensive immunosuppressive therapy and their physicians treat a fine line between too much immunosuppression (get opportunistic infections), or too little, where they would reject the organ. If a transplant patient could monitor their immune profiles in a real time basis, this would make management of the transplant much easier. It will also be appreciated that the nanosensors can be used for monitoring for response to lung cancer treatment. Mobile biosensing would detect cancer signatures, such as cytokines, proteases, and/or kinases (e.g., MMPs, EMT, etc.), in the airway or circulating in the blood. This would include free proteins and those contained within microparticles (exosomes).

In conjunction with protein sample collection, processing, profiling, and detection, embodiments described herein can also be utilized in conjunction with traditional PCR/RT-PCR, real-time quantitative PCR/RT-PCR, and isothermal PCR/RT-PCR methodologies to assess bacterial, viral, and mold infections that are associated with increased or decrease protein level expression.

Thus, assays according to the invention should not only be considered as a stand-alone technology, but can be used in conjunction with traditional approaches, especially in risk groups that have been pre-identified as being at-risk by genetic testing.

In general, the detection involves contacting the prepared sample with the nanosensor (and generally a plurality of nanosensors) to create a reaction mixture. The nanosensors can then be probed or excited using the appropriate energy source. The wavelength used will depend upon the particles used in the nanosensors. The changes in absorption and/or emission of the particles are then detected over a period of time as the target biomarker interacts with the nanosensors (e.g., such as through binding and extension of the recognition sequence).

Devices

Embodiments described herein also rely on nanosensors integrated with microfluidic and smart device platforms, which in turn, can be read by a simple-but-robust fluorescence or optical reader. "Microfluidic" refers to techniques manipulating, controlling, and/or analyzing small volumes of (fluid) samples, generally ranging from microliters ($10^{-6}$) to picoliters ($10^{-12}$). In one aspect, microfluidic technology is employed to introduce rapid, high-throughput sample collection, sample processing, sample profiling and target detection. In a further preferred embodiment, the microfluidic device will interface with a mobile computing device such as, but not limited to, a smart phone or smart tablet. Mobile computing devices including tablets, smart phones, hand held computers, laptops, etc. that are capable of optically scanning a sample and transmitting the information to other computing devices. This integrated platform will revolutionize the current "traditional" protocols, which use multiple instruments with tedious, manual sample-handling steps. In a further preferred embodiment, a stand-alone, battery-powered diagnostic platform with rapid analysis times and multiplexing capabilities will achieve statistical significance of measured quantities, with minimum consumption of human fluids (<5 µl per sampling) using a hand-held smartphone-based system that can be used as a diagnostic tool by patients and medical professionals.

The microfluidic device utilizes a plurality of detection sites in fluid communication with a micro-scale sample inlet well for introducing and analyzing a small volume of sample fluid through capillary force. In one or more embodiments, the microfluidic device includes a substrate having a first major surface (e.g., top surface) and an opposing second major surface (e.g., bottom surface). In general, the top surface comprises a sample application region and at least one detection region. The detection region may generally occupy a space in the substrate having a volume of about 100 pL to about 1 µL. The sample application region is configured to receive an amount of the test sample (e.g., from about 10 µL to about 5 mL). The detection region comprises at least one nanosensor immobilized therein/thereon for detection of a biomarker in the sample. The substrate can be a woven or nonwoven solid support, which can be elongated or of various other geometric configurations.

The sample application region is in capillary flow communication with the detection region whereby a sample absorbed on the microfluidic substrate may flow by capillary action through the solid support from the sample application region to the detection region. Accordingly, there is a region of the substrate between the sample application region and the first detection region that defines a first path of flow of the material (i.e., a channel in/on the substrate from the application region to the first detection region). The substrate can be a test strip or ribbon (with two terminal ends) or other suitable geometric shape to facilitate flow of the material from the sample application region to the detection region. The top surface of the substrate will typically be substantially planar or flat, so as not to impede the flow or the sample, and comprise a porous membrane matrix with a suitable thickness that allows flow through of the test sample (liquid). The substrate can include a plurality of detection regions, each in fluid communication with the sample application region. This can include a plurality of channels extending between the sample application region and a respective detection region. It can also include a plurality of detection regions linearly or sequentially spaced along a single channel.

For fabrication, any suitable approach can be used to create hydrophobic regions in the substrate and thus define the hydrophilic channels to direct the flow of the test sample from the sample application region to (and past) the detection region(s). For example, the configuration of the channel(s) can be created using photosensitized polydimethylsiloxane (PDMS). The porous substrate is soaked in the PDMS and then the PDMS-soaked matrix is be patterned using a mask and an appropriate light source shone through the mask to transfer the mask pattern to the PDMS-soaked porous substrate. The PDMS in the exposed regions is cross-linked and the PDMS in the unexposed regions can be rinsed away using an organic liquid. These rinsed regions are hydrophilic and define the channels through which the sample flows. The photosensitized PDMS is amenable to large-scale mass production of sensor chips at ultra-low cost. Wax printing can also be used to pattern and define the channel architecture for higher throughput if necessary.

Figure 6:
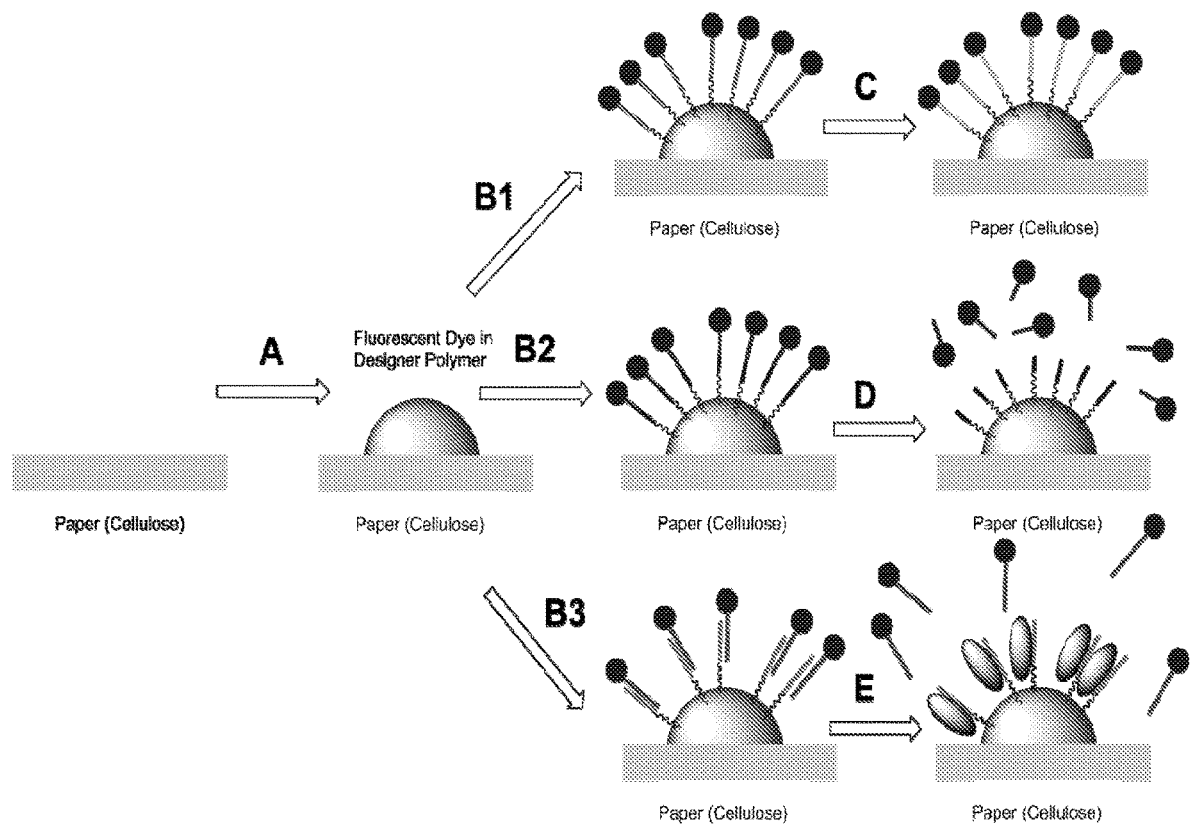
FIG. 6 is a cartoon illustration of the chemistry for attaching the nanosensors to a cellulose substrate in a microfluidics device in accordance with embodiments of the invention.

The developed nanosensors are pre-immobilized in each detection region of the substrate. An example of an approach for immobilization on cellulose is illustrated in FIG. 6. The nanosensors contain different recognition sequences for the target analyte or biomarker in the sample, and can be selectively pre-immobilized in each detection region, for example, through a needle-based pressure pull of reagents at the edge of the region. The detection regions containing the nanosensors are spatially separated. Therefore, a bandpass filter and a mask featuring pinholes are sufficient to observe the presence or absence of the detectable signal from clearly isolated regions. Thus, the collected sample is added to the sample application region and flows by capillary action to (and over/through) each detection region containing the nanosensors.

The microfluidic substrate can be any material that facilitates flow of the biological sample from the sample application region to the detection region(s) via capillary action. Thus, any porous or sorbent material (or combination of sorbent materials) can be used for the substrate, as long as it is capable of absorbing, either by capillary action or otherwise, molecules that pass through/along the substrate. For example, various sorbent materials (or combinations of sorbent materials) can be used, such as 100% cotton cellulose fiber (e.g., Whatman #1 filter paper or a similar type of material). Cellulose-based materials are particularly suited for use as test strips. In one or more embodiments, the device further comprises a wicking pad at or near the terminal end of the substrate (opposite the sample application region), with the detection region(s) being positioned therebetween. Thus, the sample, after being applied to the sample application region, wicks along the channel(s) in the substrate, causing the fluid sample to pass over the detection region(s) as it is "pulled' towards the wicking pad positioned near the terminal end of each channel (opposite the sample application region/inlet). Preferably, the detection region is positioned nearer to the sample application region than to the wicking pad. Other suitable materials for the substrate include other lateral flow assay materials, such as nylon, paper, polymers (e.g., polyester, polystyrene, polyacrylamide, nitrocellulose), and activated forms thereof.

A miniature foil heater/thermocouple can be integrated into the substrate at the detection region, if desired, to facilitate interaction of the sample with the nanosensors.

The test article further includes a cartridge for containing the solid support. The heater can also be part of a cartridge for the solid support, so long as it remains in physical contact with the solid support. Both the cartridge and solid support can be single use and disposable. The cartridge may also be reusable. In embodiments, the cartridge can be made from bio-degradable plastic. The cartridge body will generally include a bottom support structure configured to be positioned underneath the solid support (and adjacent the second major surface), and a top support structure configured to be position on top of the solid support (and adjacent the first major surface). The top support structure includes openings for depositing the biological sample and viewing changes in the nanosensors in detection region(s). The opening for deposition of the biological sample defines a sample inlet well with a sidewall extending from the opening to a bottom wall for containing the sample, where the bottom wall of the microwell is defined by the top surface of the solid support. The volume defined by the inlet well can range from about 10 µL to about 5 mL. The opening above the detection microwells can be a true "open" through-hole, or may simply be a clear viewing window.

Figure 7:
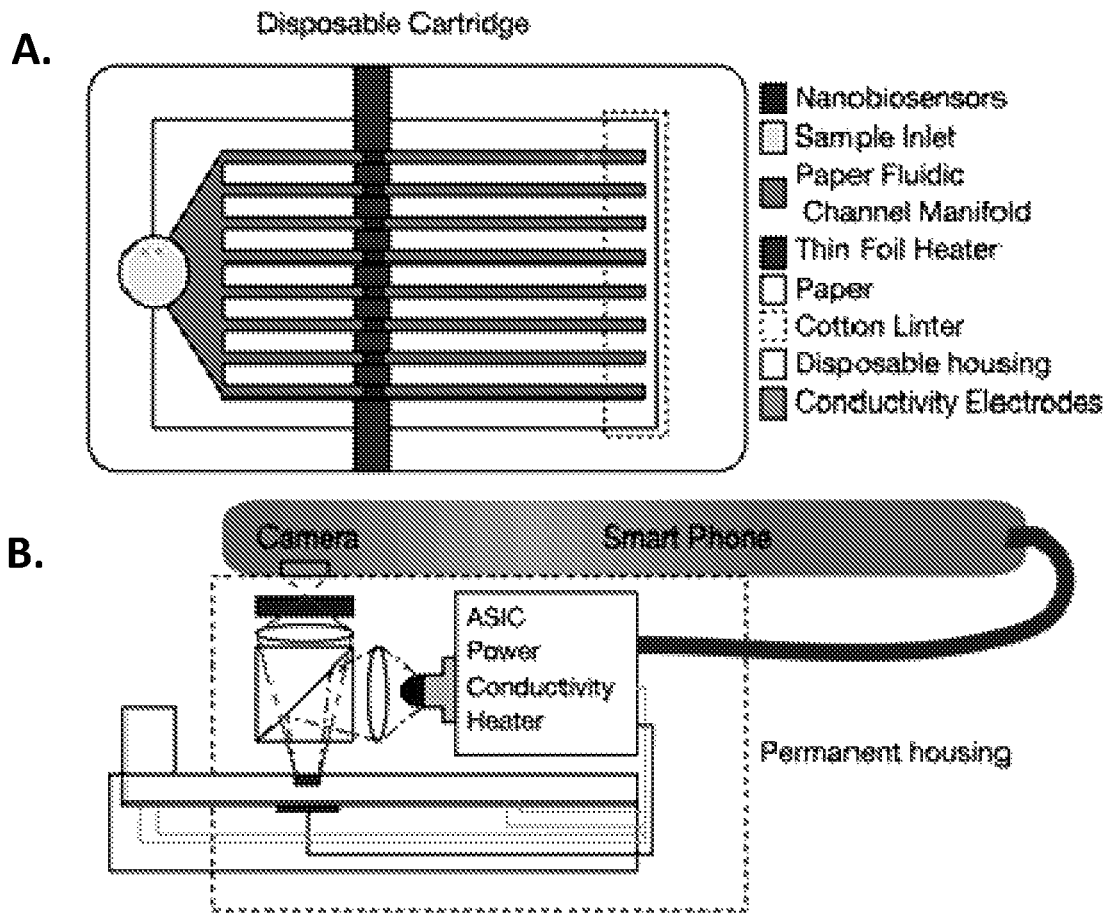
FIG. 7 illustrates a (A) top-down view and (B) side view of a generalized design for a microfluidics device in accordance with embodiments of the invention.

An exemplary device is illustrated in FIG. 7. The device further includes a housing that can be attached to a smart device and analysis cartridge. A permanent (non-disposable) housing can be used, which contains the detection optics and electronics necessary to control device heating and the assay timing. The cartridge contains the sample well, microfluidic substrate, conductivity pads, and a thin film foil heater. In use, a sample (e.g., ~2 mL of BALF fluid or ~2 mL of (lysis) buffers containing biospecimens) is added to a device with a parallel fluidic manifold as depicted. For example, the substrate includes 8 parallel channels with 6 of the channels containing a single optical-based nanobiosensor (OBN) readout pad. The 7th channel contains a positive control, and the 8th channel a negative control. The biosensors will be attached to the substrate using, for example, polysilazane attachment chemistry. All types of described nanosensors, including cytokine sensors described herein, as well as protease sensors, and arginase sensors, are adaptable to the microfluidics device. The polysilazane chemistry also allows a new approach to the nanosensor development where the primary florescent indicator is embedded directly into the polysilazane matrix as it is applied and the probe and quencher are attached afterward to the surface of the matrix. It will be appreciated that a variety of alternative cellulose linking chemistries are known in the art for immobilizing the nanosensors in the detection region(s).

After centrifugation, 500 µL of the BALF sample will be loaded into the sample inlet and evenly dispersed across the 8 channels through capillary action. The device design facilitates analysis of the sample without requiring pre-separation of the biological sample constituents. Thus, the nanosensor detection regions are positioned near the sample application region/inlet to reduce potential protein adsorption to the substrate fibers. In some embodiments, the substrate can be passivated/blocked using BSA or other blocking proteins (e.g. casein), or the substrate could potentially be coated with poly(ethylene oxide) or poly(ethyleneglycol) to reduce peptide/protein absorption. A wicking material is positioned at the terminal end of each channel to facilitate capillary flow of the entire volume of the sample across each detection zone.

Readout time can be automated. A conductivity detector can be used to mark the 0 time point when the sample inlet is wetted with the sample to quantitate the flow rate of the sample (i.e., the volume of sample that has passed over the detection region over a certain period of time). In general, the readout/detecting can be carried out anywhere from about 1 minute to about 20 minutes after the sample is introduced into the device. If sample viscosity varies significantly and adversely affects the rate of flow in the substrate, additional conductivity detectors can be spaced along the channel so that the readout time is based upon the total volume of sample passed over the nanosensor detection region(s). Fluorescence signal is best detected from the top 10 µm of the substrate so flow can be optimized to allow diffusion through the matrix to maximize signal. Channel dimensions and substrate wettability can be adjusted to provide a readout time of <10 min.

In one embodiment, upon interaction with the analytes in the sample with the nanosensor, a change may be detectable in the detection region. For example, in the presence of a target protease, the fluorophore (or quencher) is released from the nanosensor such that the fluorophore is no longer quenched. Thus, the fluorescence can be detected in the detection region, indicating that the target protease is active and present in the sample. For example, the maximum absorption of the TCPP is near 420 nm, so an inexpensive 420 nm LED or any other time of laser diode can be used for excitation of nanosensors using TCPP as the detectable particle. Collimating and beam shaping optics can also be used to create a narrow excitation line across the channels where the detection spots were laid down. COMSOL multiphysics simulations can be used to adjust the beam shaping optics to provide even illumination across all of the detection. The fluorescence emission will be collected through a 660 df 20 nm bandpass filter and imaged on a cell phone camera CCD for detection. It will be appreciated that the nanosensors are not limited to the TCPP-cyanine FRET pair exemplified in the examples. Any FRET sensing pair can be used. If other FRET pairs are used then the excitation wavelength and optical filters can be modified accordingly.

The turnover rates for the analyte enzymes are highest at 36° C. so a miniature foil heater/thermocouple can be integrated into the substrate. The heating can be controlled with PID software. The foil heater and thermocouple can also be moved off the disposable cassette and into the permanent housing with the optical detection system. The extent of the heated zone on assay performance can be identified in terms of potential diffusion and evaporation issues.

For example, if a 500 µL sample of BALF fluid is divided into 8 channels (6 for analytes and 2 for controls) that means each sensor will be exposed to about 60 µL of fluid. Clinically relevant biomarker concentrations are expected to be $10^{-11}$ to $10^{-8}$ M. The total number of moles for the lower expected concentrations should therefore be $\sim 6\times 10^{-16}$ moles which is well above the detection limit of the sensors. It will be appreciated that larger BALF volumes can be collected and so the volume used can be increased or the nanosensors can all be deposited in a single channel to further increase the number of moles of analyte they are exposed to. In this approach, the nanosensors would utilize a variety of different fluorophores with minimal spectral interference. Or, alternatively, the density of the sensors or the sensing region could be increased. The device will simultaneously measure at least 1 and as many as 20 biomarkers. Preferably, the device will measure between 3 and 15 biomarkers. More preferably, the device will simultaneously measure between 6 and 10 biomarkers.

Furthermore, relying on "paper" microfluidic technology will permit powering the device using the smart device battery only, without the need of an additional power source. Battery and supercapacitor technology is already available for powering extended applications of the device in locations without access to the electrical power grid. In future incarnations of the device, sample processing can be added to the sample inlet to filter out particulate matter so that centrifugal pretreatment of the sample will not be necessary. The most likely material for such pretreatment will be a polysulfone filter. This step will result in further reduced costs for the whole measurement process.

In a further preferred embodiment of the current invention, the relative optical density image analysis will be accomplished via a cross-platform smart device application written in Java for quantitative fluorescence measurement. LED field illumination with $\lambda=420$ nm, which completely covers the microwell chip region and allows the simultaneous detection of biological markers in the microwells. A collimating lens and a band-pass center wavelength of $l=650$ nm (625 nm-675 nm) will be attached to a 5×lens for eliminating unwanted background noise and enhancing the signal-to-noise ratio for imaging of TCPP-fluorescence.

Figure 8:
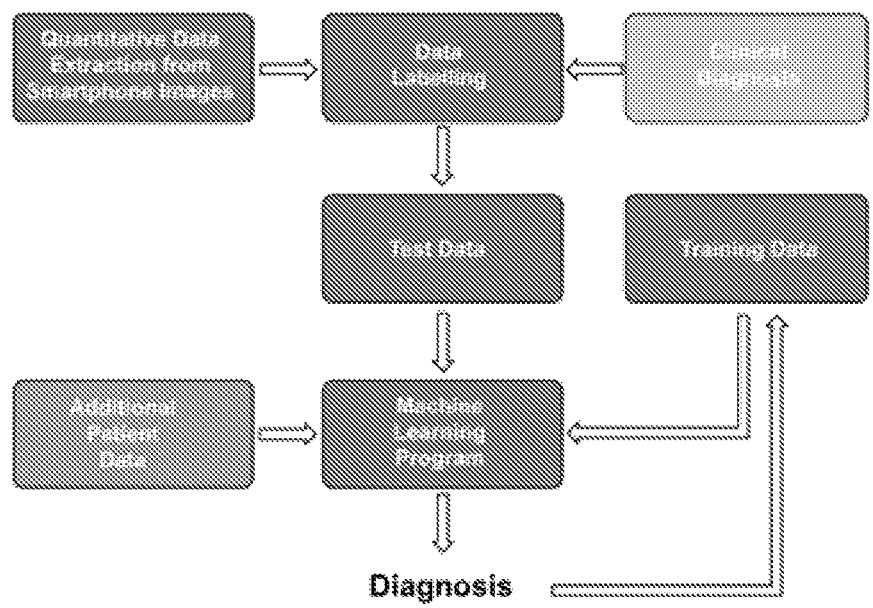
FIG. 8 is a flow chart of a learning algorithm for correlating data captured with the microfluidic devices.

In a preferred embodiment of the current invention, diagnostic results are displayed on smart phone of smart tablet and can be used to assist disease management and progression. Numerous learning algorithms are capable of capturing significant correlations between data sets by modeling the distribution of the data by introducing latent, or hidden, variables. Typical examples for this methodology are neural networks or factor analysis. The major advantage of Generative Topographic Mapping Algorithms (GTM) is that they can be extended to allow non-linear transformations while remaining computationally tractable. See FIG. 8. GTM is based on a constrained mixture of Gaussian functions whose parameters can be optimized using EM (expectation-maximization) algorithms. GTM algorithms are principally superior to Self-Organizing Map (SOM) algorithms, which do not define probability densities. GTM algorithms can be successfully utilized for the visualization and fast analysis of large arrays of chemical data. Various data distribution functions resulting in various probability distribution functions (e.g. data density and property landscapes) can be selected. Furthermore, GTM algorithms are very suitable for processing BIG DATA, if the necessity should arise in the future.

Thus, the smart device-based detection technology can be used for detection of protein signatures indicating the presence of regional epithelial injury or infection in airway samples or exhaled breath condensates; a nanosensor for point of care testing for monitoring the airway for the presence of inflammation from infection and/or environmental injury; a point of care device to diagnose or to triage children or adults with asthma for the presence of lower respiratory tract involvement; a smart-phone based device for real time monitoring of the impact of environmental exposures in home or industrial environments on the health of airway; a device for assessing progression of infection or resolution of infection in an outpatient setting; and a device for measuring response to therapy in patients with asthma or viral induced airway infections.

The use of the present nanosensors enables limits of detection (LOD) for proteases, post-translational modification enzymes (e.g., Arginase) and Cytokines/Chemokines that are significantly lower than picomolar. This technique is approaching femtomolar and sub-femtomolar LOD for numerous proteases and arginase. For cytokines, the technology is currently at LODs of about $10^{-14}$ moles $L^{-1}$. In contrast, immunoassays (ELISA), which rely on antibodies or antibody fragments, have LOD that are only sub-picomolar ($10^{-12}$ to $10^{-13}$ moles $L^{-1}$). An additional complication of immunoassay technology is that numerous antibodies are promiscuous and show significant off-target binding. That limits the number of targets that can be measured, whereas the inventive nanosensors and related methods involve highly specific recognition sequences, avoiding non-specific binding and interaction (and as such, false-positive or negative results). The present nanosensors can achieve LODs of from about $10^{-9}$ M to about $10^{-18}$ M.

The use of microfluidic devices has the advantage of processing the liquid biopsies within minutes, whereas competing technologies require several hours to reach their (respective) maximal LOD. Furthermore, microfluidic devices are capable of lowering the LOD by another one or two orders of magnitude. Therefore, the combined microfluidics and nanosensor technology is significantly faster and more sensitive than competing technologies.

Microfluidic technology also facilitates multiplexing. A unique advantage of this technology is that different biomarkers (e.g., several proteases, cytokines and kinases) can be measured in one liquid biopsy. That is, the technology permits simultaneous detection of different classes of biomarkers in a single platform—an approach previously limited to mass spectrometry. Further, the level of sensitivity far outperforms what can be achieved with MS, and also permits real-time detection and results. This enables the "Barcode Detection Principle", which is looking at 10-20 biomarkers for each disease. Looking at multiple biomarkers permits the differentiation between related diseases (e.g., lung inflammatory diseases vs. asthma) and the detection of diseases in very early states. The latter is, for instance, important for lung cancer detection, because cancer survival significantly increases when it is detected at stages 0 or 1, compared to 3 or 4. It is noteworthy that multiplex immunoassay technology exists (e.g. from Abcam), however, it still requires one antibody per bead or well. These beads/wells are combined to an array. This is conceptually different from the inventive technology.

Importantly, the nanosensor and methods measure the activity of target proteins and enzymes, as well as their concentrations and relative ratios. This is unique, because all antibody-based detection technologies utilize epitopes for target binding. They are not capable of sensing whether the enzymes are active or not. These enzymes are usually expressed as zymogens (inactive enzymes), which require either proteolytic activation or activation via posttranslational modification. Many of them show signaling activity when they are zymogens and enzymatic activity after activation. For the diagnosis of a disease, it is very important in what state (zymogene vs. active enzyme) a biomarker is. The present technology can provide that insight.

Further, this detection technology can be extended to capturing exosomes and measuring the activity of enzymes that are either bound to the exosomes surfaces or (after lysing) incorporated into exosomes. Further, lysis of the exosomes will permit the determination of the activity of enzymes or the concentration of cytokines that were contained in the exosomes' interior. Lysed exosomes can also be assessed for RNA and metabolites as markers of exosomal activities and function, as well as inflammation-induced changes in protease, kinase, or cytokine activity. Cancer-induced changes in phosphatases (e.g., alkaline phosphatase) and DNA/RNA synthesizing/modifying enzymes (e.g., ribonucleotide reductases or DNA/RNA helicases) in exosome content can also be quantified using the technology. The detection technology also permits direct or indirect assessment of exosomal stability and activity. Although the microfluidic platform is preferred to use in isolating the exosomes for analysis with the nanosensors, it will be appreciated that exosomes can alternatively be prepared and extracted using conventional technique of centrifuging the samples at low to high g for optimum duration, yielding a pellet containing exosomes that can be characterized using nanosensors described herein, in order to monitor and characterize exosomal activities and function defined by quantification of changes in protease, cytokine, and/or kinase secretion.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Nanosensor Preparation

In this Example, a nanosensor for detecting cytokine activity was prepared. The oligopeptides are synthesized by solid phase synthesis. The fluorescent dye is attached while the oligopeptide is still on the column. After cleavage from the resin (Wang resins are used), the oligopeptide is dialyzed, lyophilized and then purified by means of gel chromatography. Typical purities are 85% after synthesis, 95% after dialysis and 99++ percent after gel chromatography. The following supramolecular recognition sequence was used for IL-6: NRPQAWMLG (SEQ ID NO:21)

Synthesis of Peptide Sequence.

A commercially available dry resin (purchased from Peptides International) with the starting amino acid (500 mg) was placed in the reaction vessel. Next, 4 ml DCM was added until all resin beads are immersed to swell the resin in the DCM for 20 minutes. This helps the resin to react well with the next amino acid to be added. The resin suspension was gently swirled for 20 min. Then the DCM was removed by filtration under vacuum.

The first $N^\alpha$ Fmoc deprotection was performed using 4 ml 80/20 DMF/diethylamine solution. The mixture was stirred for 1 min and the solution was then removed by vacuum filtration. The same step was repeated within 10 min. The resin was then washed five times with 4 ml of DMF by stirring it for 30 s. The solvent was removed by vacuum filtration.

To add the second amino acid to the resin, the $N^\alpha$ Fmoc protected amino acid (Resin:Amino acid=1:3 molar) and HBTU (Resin:HBTU=1:2.9 molar) was dissolved in 9.6 ml of DIEA/DMF (1:23 v/v) solution. The mixture was then added to the resin in the vessel and stirred for 30 min. This step is repeated once to increase the probability of binding the amino acid to the resin. Then the coupling solution was removed by vacuum filtration. Washings were performed with 4 ml DMF for 30 s four times.

The desired peptide sequence was assembled in a linear fashion from the C-terminus to the N-terminus (the C_N strategy) by repetitive cycles of $N^\alpha$ deprotection and amino acid coupling reactions. Deprotection and coupling processes are repeated until the desired sequence is obtained. The TCPP (tetrakis-4-carboxyphenyl-porphyrin) dye is attached to the N-terminal of the peptide sequence utilizing the same procedure as if adding an amino acid.

Resin:TCPP molar ratio was 1:3. After the addition of dye to the resin, it was swirled for 24 hrs at RT and the excess dye was washed off with DMF solution.

In order to release the peptide from the resin, it was swelled with DCM. Then 4 mL of cleavage cocktail (trifluoroacetic acid/water/triisopropyl silane 3.8/0.1/0.1) was added to the resin. The resin was swirled gently for 3 hrs at RT. Then it was filtered into 20 ml cold diethyl ether. The peptide sequence was precipitated and was washed with cold ether three times. The precipitate was isolated by centrifugation (10000 rpm, for 5 min). Finally, argon was applied to dry the product for safe storage.

The oligopeptide was purified by quantitative HPLC. MALDI-TOF (Matrix-assisted laser desorption/ionization-time of flight mass spectrometry) was used to characterize the peptide sequence.

Synthesis of Nanosensor:

To assemble the cytokine nanosensor, 100 mg of $Fe/Fe_3O_4$ nanoparticles was mixed with 16.5 ml of distilled DMF, 14.13 mg of TCPP-bound peptide sequence, 10.0 mg of EDC, and 10.0 mg of DMAP. The mixture was stirred at room temperature for 24 hrs and the excess dye was removed by dialysis. The end-product was lyophilized.

Example 2

Nanosensor Calibration

The nanosensors can be calibrated according to the following procedures. Calibration of the IL-6 nanosensor was conducted with commercially available recombinant human IL-6 to validate the sensing capabilities. The calibration curves are recorded as a function of IL-6 concentration. Commercially available recombinant human IL-6 purchased from BD Biosciences was used. Concentrations ranging from $1.0 \times 10^{-16}$ mol $dm^{-3}$ to $1.0 \times 10^{-8}$ mol $dm^{-3}$ were utilized for the calibration process. Plate reader technology was used to measure the fluorescence signals. Five replicates from each concentration were analyzed in order to get accurate data. Recombinant human IL-6 is stored at −80° C. The assay procedure was as follows:

A Biotek FL800 plate reader (tungsten halogen lamp, excitation bandpass filter: 421±10 nm, analysis bandpass filter: 650±25 nm) with 96-well plates was used. The plate reader was set to 25° C. Distilled water was used for all procedures.

Solution (1): HEPES (25 µmol) buffer (2-[4-(2-hydroxyethyl) piperazin-1-yl]ethanesulfonic acid) prepared with Ca(II), Mg(II), and Zn(II)-enriched (10 µmol each) at 300 K (pH=7.2). Solution (2): $Fe/Fe_3O_4$ based nanoplatform was prepared by dispersing 0.3 mg of the nanoplatform 1.0 mL of HEPES buffer by sonication for 10 min at 25° C.

The following samples were prepared by adding solution (1) or nanoplatform (2) with 5 µL of commercially available L-6 sample; A: Sample Control (125 µL of solution (1)+5 µL IL-6 sample); B: Assay (125 µL of assay (2)+5 µL IL-6 sample); C: Assay Control (125 µL of nanoplatform (2)+5 µL of solution (1)). Each sample (total 130 µL) was loaded into one of the wells of 96-well plates. The solutions were incubated at 37° C. for 60 min and minimum five replicates of each assay were prepared. Detection of nanoplatform fluorescence was performed utilizing a 96-well fluorescence plate reader (BioTek Synergy 2) at 421 nm excitation wavelength.

Figure 9:
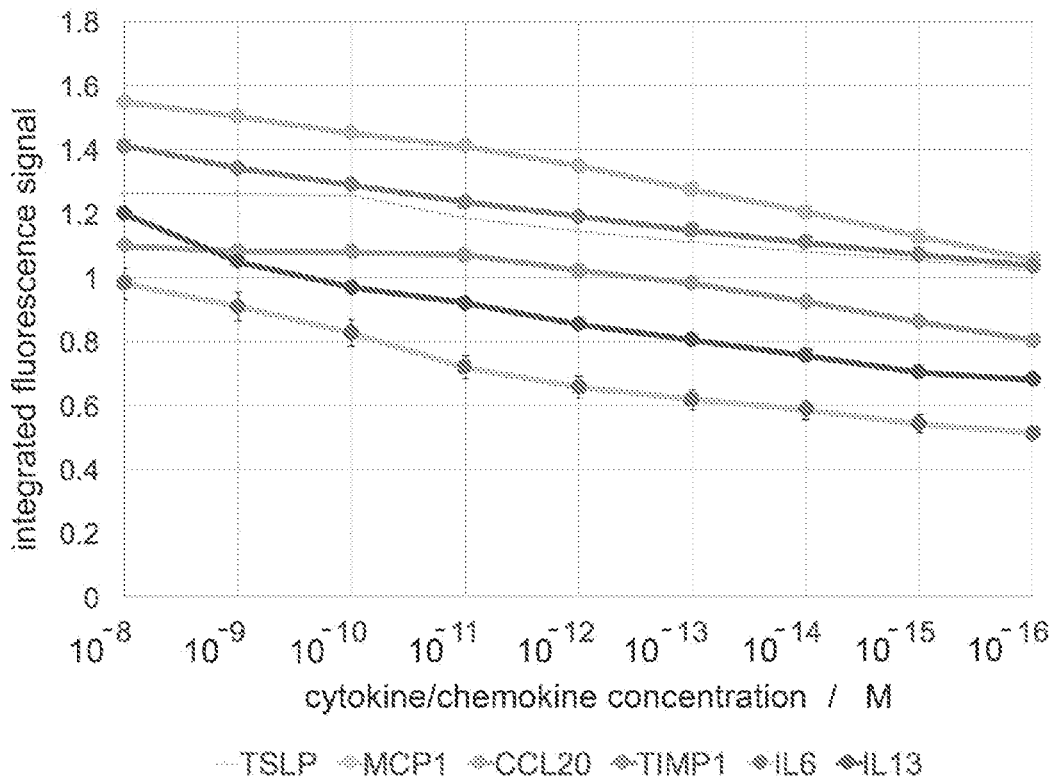
FIG. 9 is a graph of the calibration results for the nanosensors for cytokine detection, showing the log [cytokine concentration] vs. integrated fluorescence intensity, with a maximal experimental error from 5 repetitions of +/−3 relative percent.

Using the integration of the fluorescence decay graphs, calibration curves were recorded. The data is presented in the table below, as well as in FIG. 9.

Calibration with Commercially Available
Interleukin-6 (Enzo Lifesciences)

| Concentration | (Sample-Sample control)/Assay control |
|---|---|
| $\times 10^{-8}$ | 0.9795 |
| $\times 10^{-9}$ | 0.9064 |
| $\times 10^{-10}$ | 0.8260 |
| $\times 10^{-11}$ | 0.7163 |
| $\times 10^{-12}$ | 0.6558 |
| $\times 10^{-13}$ | 0.6167 |
| $\times 10^{-14}$ | 0.5847 |
| $\times 10^{-15}$ | 0.5309 |

Example 3

Development of Recognition Sequences

The supramolecular recognition sequences were developed according to the following procedure: A) The primary structure of the target was retrieved from a data bank (e.g. UniProtKB or Protein Data Bank). B) The tertiary structure of the target was determined and then refined utilizing protein structure predicting software, such as the GalaxyWEB protein structure prediction cluster, developed by Dr. Seok at the Computational Biology Lab, Seoul National University, Korea. C) The primary structure of a monoclonal antibody (MAB) fragment against the target was retrieved from a data source (e.g., Protein Data Bank, SciFinder, or information provided by the vendors of antibodies). A tertiary structure was generated using GalaxyWEB. D) A docking procedure between the target and antibody chain is simulated using the Mobyle platform developed by the Institut Pasteur Biology IT Center, Paris, France. This procedure reveals the "true" epitope of the target. E) A final "site finder" procedure is then performed on the Mobyle platform docking the epitope of the target to the improved structure of the antibody (Ab) fragment. This structure reveals the peptide sequence of the Ab fragment that is actually responsible for binding to the target.

If this sequence was linear, it was synthesized and used as a recognition sequence for the nanosensors. If it was not linear, or if the LOD of the resulting nanobiosensor was not at least $10^{-14}$ M, the in silico procedure was be repeated using the structural information from another mAb.

Example 4

Detection of MMPs and Cytokines in Exhaled Breath Condensate

Figure 10:
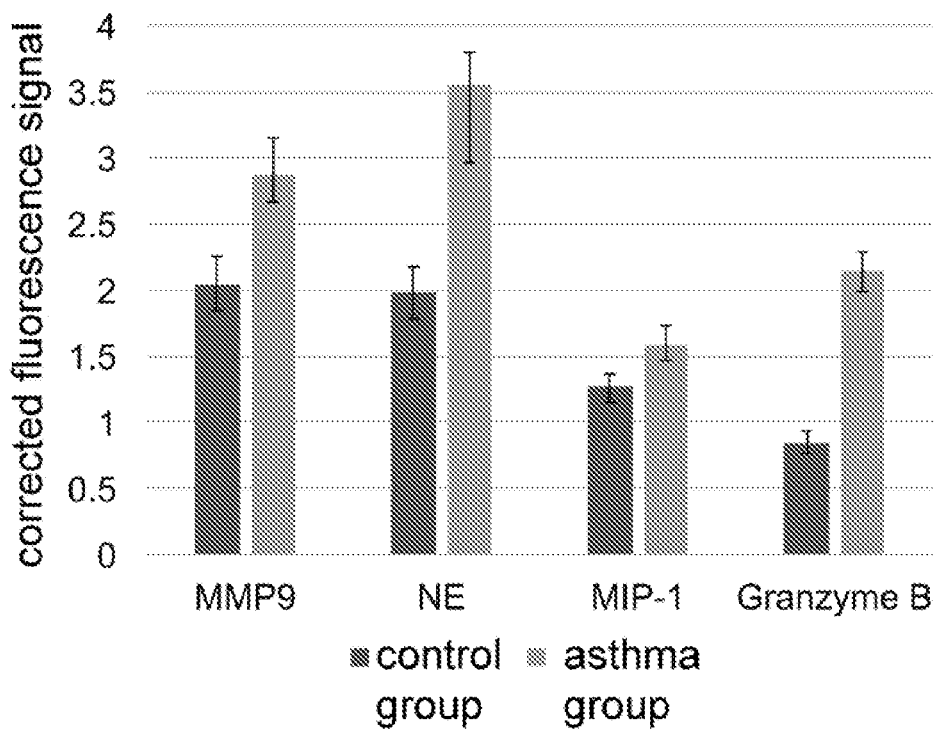
FIG. 10 is a graph of the MMP9, NE, MIP-1, and Granzyme B levels detected using a Synergy H1 fluorescence plate reader in the asthma and control groups from Example 4.

Exhaled breath condensate (EBC) samples from the UTMB biorepository bank were analyzed using nanosensors containing detection sensors for various biological markers. The EBC samples had been collected from three human subjects who did not show any signs of asthma, and three who were diagnosed with mild asthma (no corticosteroids). For these experiments each EBC sample was first mixed 1:1 (v/v) with Ca(II), Mg(II), and Zn(II)-enriched (0.35 mmol each) HEPES buffer (2-[4-(2-hydroxyethyl) piperazin-1-yl] ethanesulfonic acid) at 300K (pH=7.2). This mixture was then incubated for 60 min at 37° C. with respective nanosensors for ADAM 33 (disintegrin and metalloproteinase domain-containing protein 33), granzyme A,B, MMP's 8 and 9, neutrophil elastase (NE), and the cytokines MCP-1 (monocyte chemotactic protein 1) and MIP-1 (macrophage inflammatory protein 1) in HEPES buffer. Detection of nanosensor fluorescence ($\lambda_{exc}$=421 nm, $\lambda_{em}$: 680-720 nm) was performed utilizing a 96-well fluorescence plate reader (BioTek Synergy H1). For granzyme B (all three patients diagnosed with mild asthma), and neutrophil elastase (one patient), distinct differences in the enzyme activities in EBC between the mild asthma group and control group were found. Elevated levels of MMP 13 were not detected in either group. The levels of MMP8 (not shown) and MMP9 varied from subject to subject, but were clearly measurable. Individual levels of MCP-1 and MIP-1 were present in the ECB samples of all six human subjects. An important outcome of this experiment is that these important biomarkers (e.g., MMPs, granzymes, and cytokines) are present at readily measurable levels (picomolar to sub-nanomolar) in ECB. The results are presented in FIG. 10.

Example 5

Detection of MMPs and Cytokines in Mouse Bronchoalveolar Lavage Fluid

Figure 11:
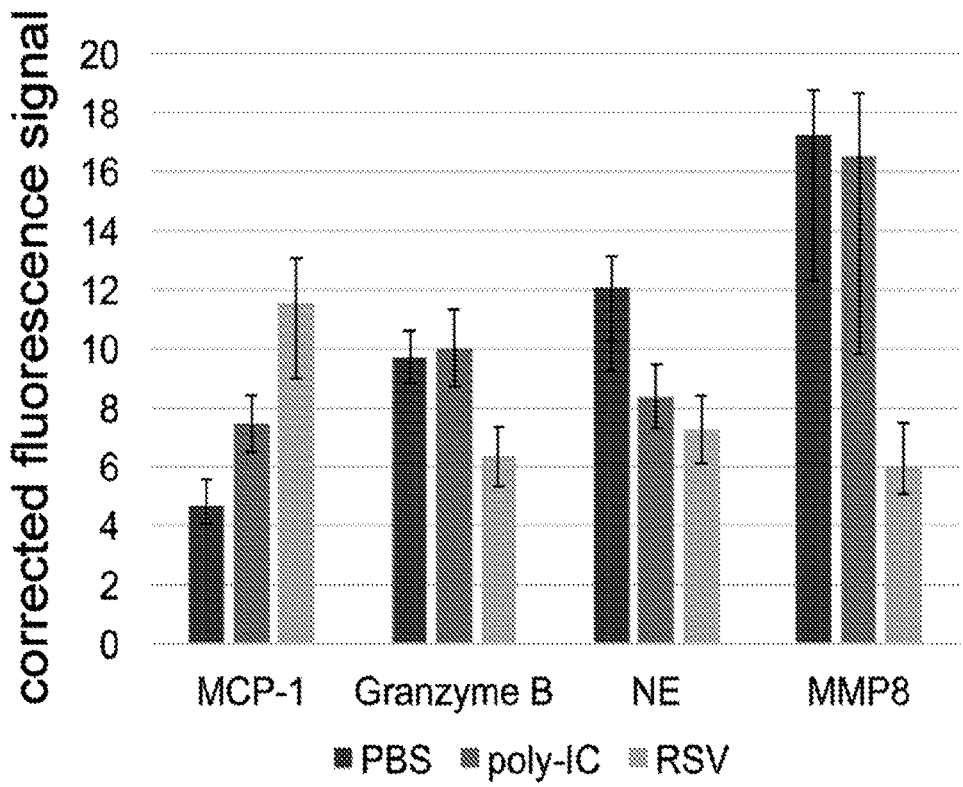
FIG. 11 is a graph of measurements of MMP8, neutrophil elastase, granzyme B and MCP-1 levels in murine BALF from Example 5 captured using a Synergy H1 fluorescence plate reader.

In preliminary studies, the lungs of nine mice were treated with phosphate buffered saline (PBS, group A), the immunostimulant polyinosinic:polycytidylic acid (poly IC) was administered to eight mice (group B) to induce lung injury and inflammation, and five mice were given Respiratory Syncytial Virus (RSV) to induce airway infection (group C). Bronchoalveolar lavage fluid (BALF) samples were collected from each mouse, and measured for various biomarkers. Among other proteases and cytokines, MMP-8, neutrophil elastase (NE), granzyme B and MIP-1 were measured in the BALF samples. Based upon the results, the administration of PBS has caused an immune reaction. All four biomarkers indicate that the mice in group B reacted to receiving poly(I:C), whereas a weaker immune reaction to RSV was observed in group C. The results are presented in FIG. 11.

1) Detection of Exosomes Via Light Scattering

A) Unfrozen bronchoalveolar lavage fluid (BALF) from untreated mice was diluted 1:1 with HEPES buffer.

B) 10 microliters of this mixture were mixed with 1.0 mL of HEPES buffer for measuring the hydrodynamic diameter of the exosomes (d=710 nm).

C) 10 microliters of a dispersion of 1.0 mg Fe/Fe$_3$O$_4$-nanoplatform bearing 75+/−5 peptide aptamers for binding of the tetraspanins CD9, CD 63, or CD81, in 1.0 mL of HEPES buffer were mixed with 1.0 mL of HEPES buffer for measuring the hydrodynamic diameters of the nanoplatforms for exosome detection:

Fe/Fe$_3$O$_4$-CD 9: 296+/−10 nm
Fe/Fe$_3$O$_4$-CD 63: 384+/−15 nm
Fe/Fe$_3$O$_4$-CD 81: 634+/−20 nm

Since the diameter of individual Fe/Fe$_3$O$_4$-nanoparticles is approx. 20 nm, as measured by TEM, these findings are a clear indication that clustering between individual Fe/Fe$_3$O$_4$-nanoparticles occurs.

Figure 12:
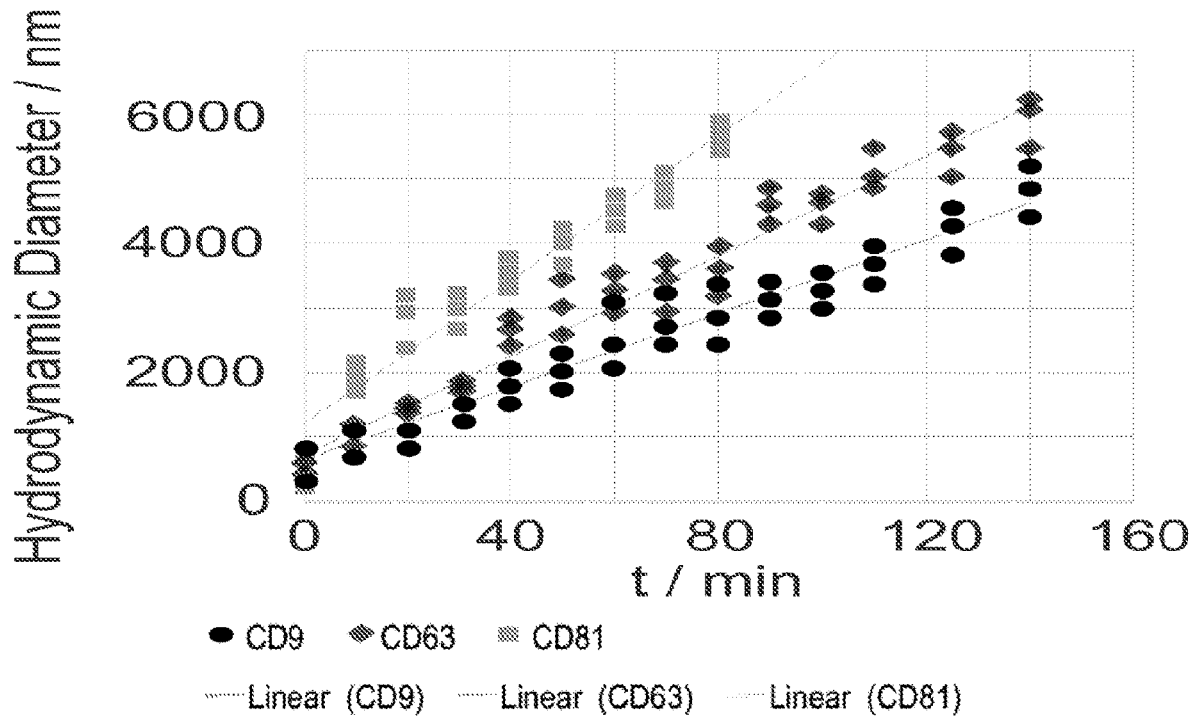
FIG. 12 is a graph of the hydrodynamic diameters of (forming) aggregates between the exosomes in BALF and the nanosensors designed for targeting CD9, CD63, and CD81. The Figure shows Hydrodynamic Diameter vs. Time (in minutes). The experiments were performed using a Nanobrook 90Plus Zeta Particle Size Analyzer (Brookhaven Instruments Corporation)

D) 10 microliters of exosome-containing HEPES buffer and 10 microliters of CD (9,63, or 81)-nanoplatform— containing HEPES buffer were added to 1.0 mL of HEPES buffer and vortexed for 10 s. Then, the hydrodynamic diameter was measured at 298K as a function of time. The results are summarized in FIG. 12. From the data, the following conclusions can be drawn:

Shortly after incubating the exosomes and the nanoplatforms with targeting peptide aptamers, significant increases in the observed hydrodynamic diameters can be seen. This can be interpreted as evidence that the exosomes promote the clustering of the nanoplatforms. This is a highly dynamic process, which is not finished after 140 min. However, the presence of exosomes can be detected with certainty 10 min. after incubation.

Each of the nanoplatforms bearing CD9, CD63 and CD81 has different binding efficacies, or, alternatively, the three tetraspanins are not available in equal concentrations at the exosomes' surfaces.

Incubation of at least 1 h is recommended if the exosomes should be magnetically captured for subsequent lysis and analysis of their protein, DNA and RNA content. However, this is not necessary for detecting the presence of exosomes.

2) Detection of Exosomes Using Electrical Impedance Measurements

Electrical Impedance Spectroscopy is a powerful electrochemical method for the characterization of interfaces. The underlying equation is an expression analogous to Ohm's Law that permits calculating the impedance of a system as:

$$Z = \frac{E^1}{I^1} = \frac{E_1 \sin(\omega t)}{I_1 \sin(\omega t + \phi)} = Z_1 \frac{\sin(\omega t)}{\sin(\omega t + \phi)}$$

Z0: Impedance, φ: Phase Shift (Phase Angle)

Figure 17:
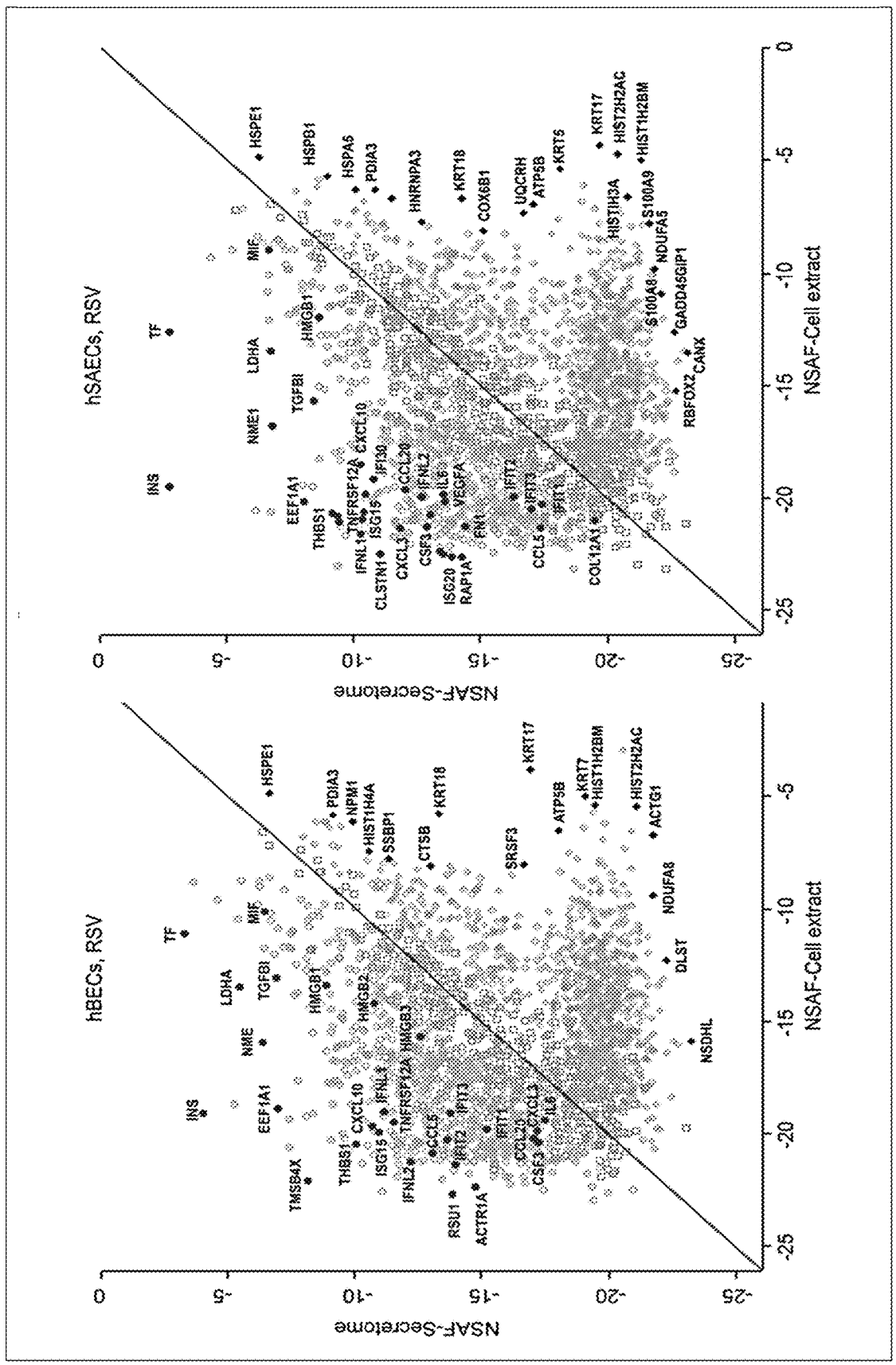
FIG. 17 is a graph showing (left panel) the differential expression of secreted proteins (top) vs cell lysates (bottom) for hBECS, and (right panel) the differential expression of secreted proteins in secreted proteins vs lysates for hSAECs.

The Phase Angles as a function of applied frequency ω were investigated in 0.10 M HEPES buffer. FIG. 17 shows the observed phase angles for the following compositions:
0.10M HEPES buffer
100 microliters of this exosomes/HEPES 1:1 v/v were mixed with 1.0 mL of HEPES buffer for measuring the hydrodynamic diameter of the exosomes
10 microliters of a dispersion of 1.0 mg $Fe/Fe_3O_4$-nanoplatform bearing 75+/−5 peptide aptamers (see Table 1) for binding of the tetraspanin CD 81, in 1.0 mL of HEPES buffer were mixed with 1.0 mL of HEPES buffer.
100 microliters of exosome-containing HEPES buffer and 10 microliters of CD 81-nanoplatform—containing HEPES buffer were added to 1.0 mL of HEPES buffer.

Figure 13:
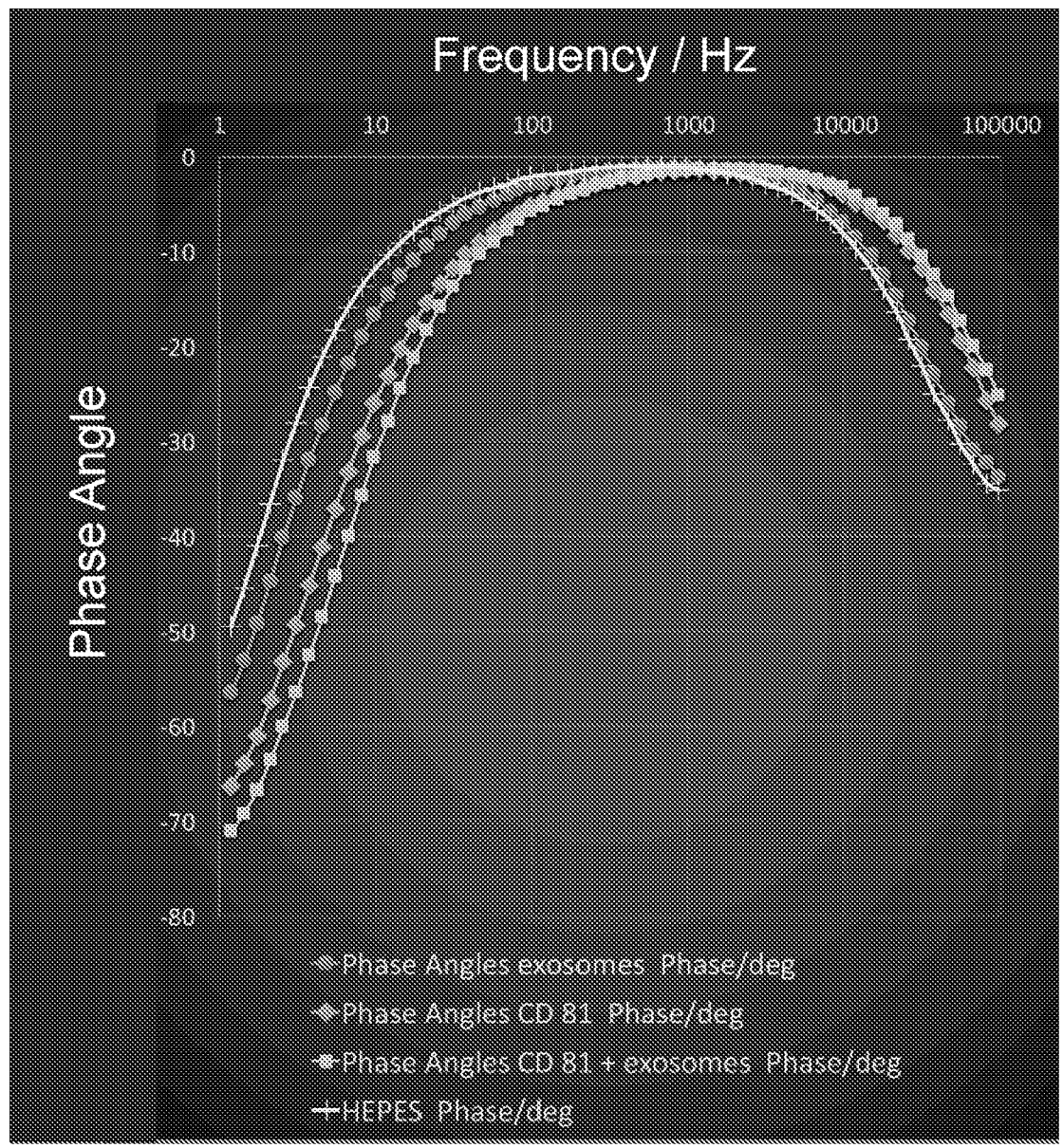
FIG. 13 is a graph of the plot of the observed phase angles between applied voltage and measured current as a function of frequency, collected using a CHI 650B Analyzer/Workstation with Pt net electrode (Methrohm) under the following parameters: Initial E=0.3 V, high frequency=1×105 Hz, low frequency=1 Hz, Impedance FT, Amplitude=0.005 V, quiet time: 30 s. log 10 Frequency vs. Phase Angle is shown.

All mixtures were constantly purged with N2 for 10 min before and during the measurements. All measurements were repeated three times. It is noteworthy that the supramolecular associates between exosomes and nanoplatforms bearing 70 peptide aptamers for CD 81 recognition can be discerned in the low frequency range (1-10 Hz) of FIG. 13 (which is a so-called Bode Phase Plot). This offers, principally, an opportunity for the fast recognition and differentiation of exosomes in a Point-of-Care Device (POCD). The nanoplatforms for CD 9 and CD 63 detection showed, principally, the same behavior.

Example 6

Microfluidic Device Valve and Pump Design

Figure 14:
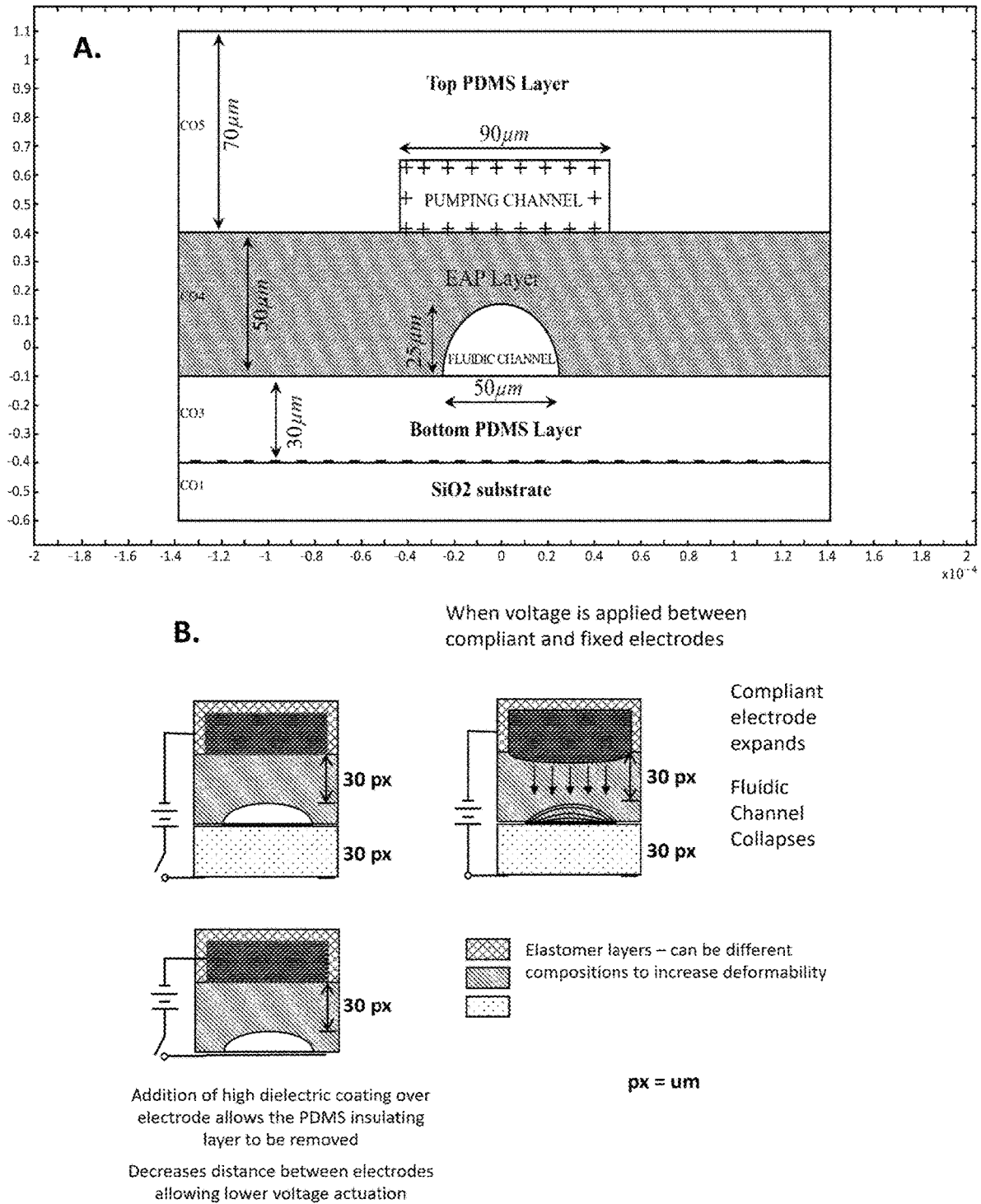
FIG. 14 illustrates the general Configuration of IDEA valves. (A) COMSOL multiphysics simulation 2-D cross section of an IDEA actuator. (B) Depiction of the operation of an IDEA actuator. Once the switch (e.g. optodiode) is closed the force generated between the two electrodes closes the fluidic channel between them. In order to minimize the distance between the compliant electrode (top) and the non-compliant electrode (bottom), the bottom PDMS layer may be replaced by a thin layer high dielectric film. This film can be made amenable to surface modification.

In this example, a new design paradigm for a dielectric actuator for fabrication of both valves and pumps on microfluidic devices is described. An exemplary design is shown in FIG. 14. In this design the fluidic channel is sandwiched between a liquid compliant electrode (top) and a planar electrode (bottom). When an electric field is applied between the two electrodes the dielectric layer and fluidic channel between them changes shape due to the force generated between the electrodes. As the dielectric is not compressible, the dielectric layer must change shape as discussed above. The easiest method to relieve the stress is to compress the fluidic channel thus pinching off the channel between the 2 electrodes. This effectively forms a valve, which under unpowered conditions is normally open. In order to minimize the distance between the two electrodes without exceeding the electrical breakdown capacity of the dielectric, a thin insulating (dielectric) layer may be applied between the bottom electrode and the fluidic channel. This layer may be formed of silicones, titanium oxides, titanates (e.g., Sr and Ba) or perovskite materials that have significantly higher electrical breakdown potentials than PDMS or other types of elastomers. In addition, such surfaces have functionalities that make them suitable for modification and the attachment of sensing species as described below.

Figure 15:
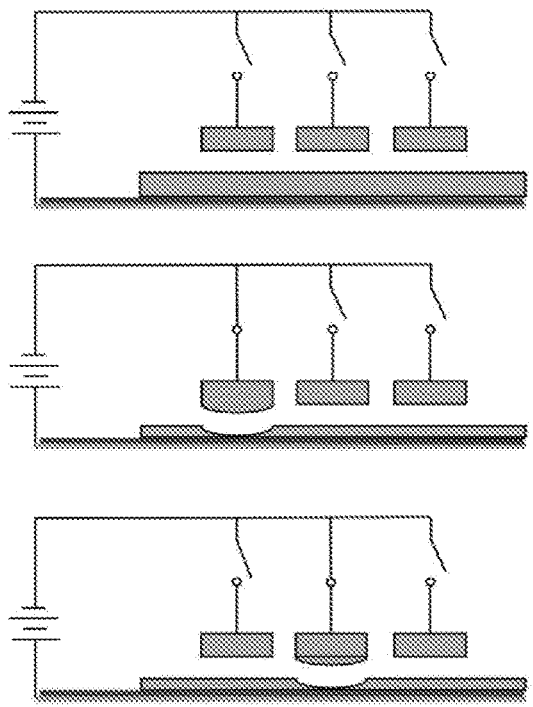
FIG. 15 illustrates 3 valves along a channel that can be configured to create a peristaltic pump in the microfluidic device.

By creating 3 normally open valves along a channel (FIG. 15) a peristaltic pump can be created that is improved over pneumonic actuation. That is, pneumatic actuation requires significant off chip equipment, and the solenoid valves used to operate the gas lines are power intensive. In addition, liquid/air tight seals with the chip must be made for all of the valve control lines. Dielectric valves, conversely, do not require air/liquid tight interfaces. Connections to electrical power supplies can be made using small, flexible wires or pins. The capacitance of the actuators is low and so little power is required to drive the valves. This allows high voltage/low current power supplies to be used for actuation. Such supplies could even be powered using computer USB ports. In such designs, a single power supply can be used with several high voltage switches. The switches can be opto-diodes. Such switches can work at speeds of over a kHz. They are compact and inexpensive.

Figure 16:
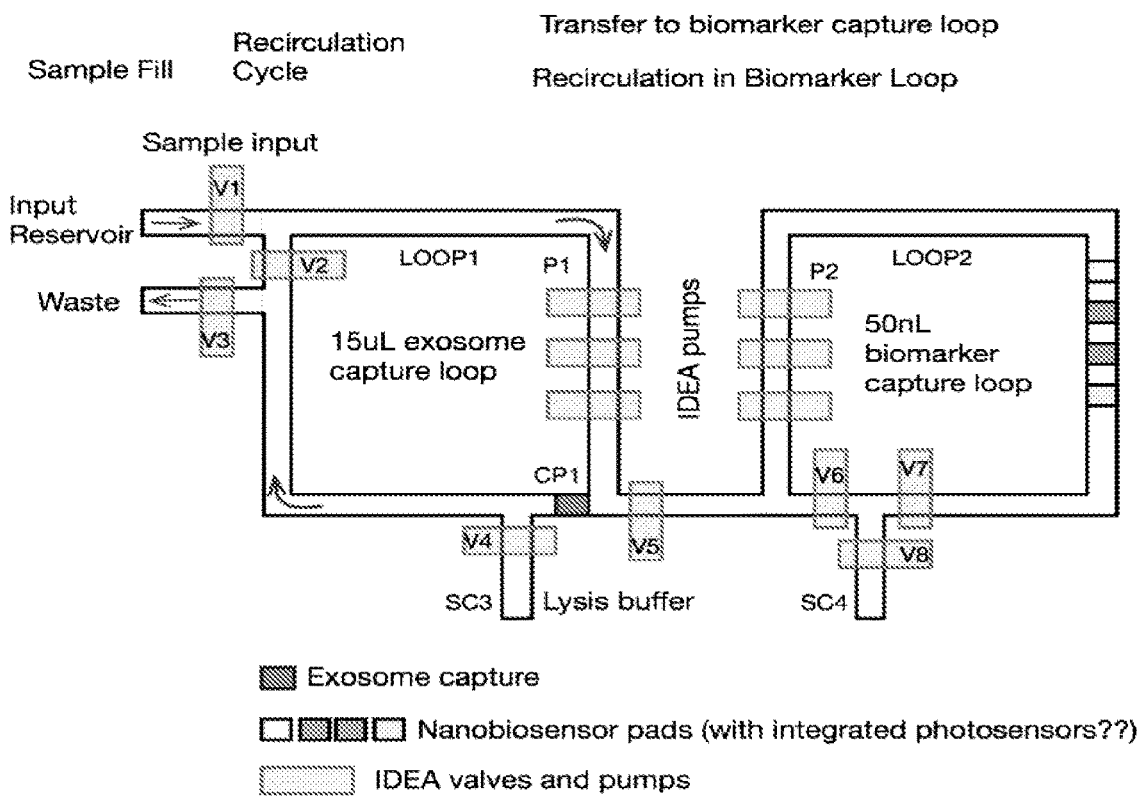
FIG. 16 is a diagram (not to scale) of a point of care device with integrated IDEAs for the detection of biomarkers in bodily fluids.

A design for an exemplary robust point of care (POC) system that can be used for disease diagnosis is shown in FIG. 16. In this device, two recirculating microfluidic loops are used to first concentrate a biologically significant molecule or species (e.g., exosomes), from a biological sample (e.g. blood, sputum, nasal lavage, etc.) and then to detect the biological marker(s) using a variety of sensing platforms. In the first loop, a volume of several mL of biological fluid can be loaded into the loop displacing a sterile PBS type buffering system. The fluid is first loaded into an input reservoir. Valves V1 and V3 are opened while valves V2, V4, and V5 are closed. The pump in loop one (LOOP1) is opened and the sample drawn into the loop as the PBS is displaced and sent to waste. Once LOOP1 is filled. Valves V1 and V3 are closed and valve V2 is opened. The sample is then recirculated over the capture pad CP1 until a sufficient quantity of the analyte (e.g., species, exosome, etc.) is captured. The capture may be attained using a variety of affinity agents including but not limited to antibodies, aptamers, peptide aptamers, Fab fragments, etc. Once captured and concentrated on CP1, pump P1 will be stopped. Valves V4, V5, V7, and V8 will be opened. Pump P1 valves will be closed along with valve V6. Pump P2 will then be actuated to pull lysis buffer out of side channel SC3, over the capture pad CP1 and into the second loop. The concentrated analytes released from CP1 will flow through LOOP2 displacing the sterile PBS solution in that loop. The displaced sterile PBS will exit through side channel SC4. After filling LOOP2 with the concentrated analyte, valves V5 and V8 will be closed and valves V6 and V7 will be opened. This will allow the recirculation of the analytes in LOOP2 over the sensor pads. The recirculation will continue to occur until a sufficient of biomarkers if present are captured to produce a detectable signal.

The device material used to fabricate the microfluidic channels and the compliant electrode can be a silicone, modified silicone or acrylic elastomer. These materials are highly transparent. The bottom electrode can be made from indium tin oxide (ITO) deposited on a thin glass slide, as the ITO and slide are transparent and will allow easy observation and troubleshooting of the device. The non-compliant electrode material, however, can be any electrically conducting substance. Between the stationary electrode and the fluidic channels a high dielectric coating will preferably be used. This coating may be a silicone, acrylic, cellulose acetate, or barium (or strontium) titanate, among others. The bottom non-compliant electrode may cover the entire bottom plane of the device and serve as a ground plane or high voltage plane. The valves would then be actuated by applying a potential to the compliant electrodes or grounding them if they are otherwise floating. Alternatively, all of the compliant electrode channels can be grounded and the non-compliant electrodes patterned individually on the glass slide. In this configuration, the valves could be individually actuated either through switching the ground electrodes from floating to grounded or be applying a potential to one of more of the patterned non-compliant electrodes.

Example 7

Printable Detection Systems for Paper Microfluidic Devices

The disadvantage of all nanoplatforms/nanobiosensors for the detection of biospecimens of interest is that they have to be pre-assembled. The following modification permits the printing of the sensing nanoplatform in consecutive steps using conventional desk-jet technology. A fluorescent dye, preferentially with a high fluorescence or phosphorescence quantum yield (e.g. Rhodamine B) will be dissolved in an inorganic solvent (e.g. a hydrocarbon, an ether, or an ester), together with a polysilazane designer polymer:

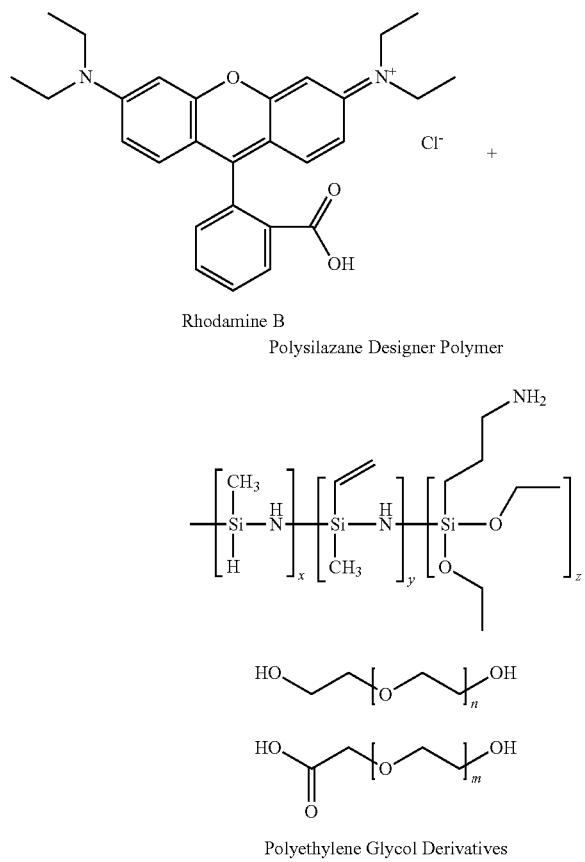

Rhodamine B
Polysilazane Designer Polymer

Polyethylene Glycol Derivatives

A mixture of rhodamine B, a polysilazane designer polymer (x, and z can be varied from 0-100 percent, y from 0-25 percent); n,m are between 1 and 100,000 will be dissolved in a solvent without functional groups featuring polar hydrogens (—COOH, —OH, —NH, —SH, HX, etc). Typically, 1-10% by weight of the polysilazane designer polymer and 0-5 percent by weight of the polyethylene glycol derivatives are dissolved, leading to a stable "ink" (store in the dark and protect from humidity). This ink can be used to print spots of immobilized dyes onto cellulose paper. The surface will be hydrophilic, so that aqueous buffers can react with it. An exemplary protocol is below.

A: Printing of the Designer-polysilazane supported fluorescent dye (every fluorescent dye possessing a functional groups featuring at least one polar hydrogen) onto the paper. The polar hydroxy groups react either with the Si—H groups of the designer polysilazane under formation of $H_2$ and O—Si bonds, or they exchange Si—NH— against Si—O—, and $NH_3$ is eventually released. After 0-10 min of solvent evaporation and formation of a fluorescent dye containing coating, step B follows. This technology is forming sub-micrometer layers on immobilized fluorescent dyes on paper (or, more generally, substrates).

B1: Printing of an oligopeptide used in posttranslational sensors featuring 1-5 serines at their C-terminal ends (e.g., GRRRRRRRGSSS, SEQ ID NO:76), dissolved in DMF or any other dipolar aprotic solvent (DMA, acetonitrile) or methyl-group capped oligoethylene glycol, in which the oligopeptides are soluble. The —OH groups of the serine units at the C-terminal end react with the designer polysilazane under formation of H2 and O—Si bonds, or they exchange Si—NH— against Si—O—, and NH3 is eventually released. At the N-terminal end of the oligopeptide is a FRET partner or quencher attached, which is matched with the emission spectrum of the immobilized dye.

B2: The same reaction as described under B1 can be applied to print the "classic" consensus sequences onto the very thin layer of immobilized fluorescent dye. Again, we add 1-5 serines to the C-terminal end of the polymer. Principally, threonine or tyrosine would work as well.

B3: A different strategy has been devised for determining the concentrations of cytokines (protein targets) in paper microfluidic devices. The first oligopeptide that is printed onto the thin layer of designer-polysilazane immobilized fluorescent dye contains the paratope for binding the target (e.g., cytokines, growth factors, enzymes that don't cleave/chemically modify the oligopeptide tether). It contains 1-5 serines at its C-terminal end, as previously described. Serines are optimal, because they are hydrophilic and facilitate the aqueous buffers containing the target proteins to flow over the nanosensor capture area (instead of around it). The second oligopeptide contains the epitope of the original target. It will be displaced by the real target, which causes the release of the quencher, which is attached to the N-terminal end of the second oligopeptide. In order to make sure that the second oligopeptide is released by the target, and to provide a larger range of detection, a series of mutations are introduced in the second oligopeptide. This causes consecutively weaker binding to the first oligopeptide and, consequently, easier release.

C: Reaction Possibilities:

C1: Reaction with arginase (or other posttranslational modifying enzyme). The fluorescence is increased, because the distance between immobilized fluorescent dyes and quencher increases.

C2: Classic protease-cleavage reaction, except that the quencher is removed.

C3: The real target displaces oligopeptide 2, and together with it the quencher. Using Interleukin 13 as the example, Oligopeptide 1, to be bound to the surface of the polysilazane designer polymer: AVYYCQQNNEDP-RTFGGGTKSSSG (SEQ ID NO:77). Oligopeptides 2: Dye-QFVKDLLLHLKKLFREGRFNG (SEQ ID NO:78), Dye-QFVKDSLLHLKKLFREGRFNG (SEQ ID NO:79), Dye- QFVKDSLLHLSKLFREGRFNG (SEQ ID NO:80), and Dye-QFVKDSLLHLSKLFRESRFNG (SEQ ID NO:81). One, two and three serines are introduced into the developed sequence. Each serine weakens the binding constant by approximately one order of magnitude. Virtually, any natural or unnatural amino acid, as well as D-amino acid at any position in the sequence can be used to weaken the binding and thus provide a greater range of measurements (if mixtures of oligopeptides 2 are bound to oligopeptide 1).

Example 8

Analysis of Cell-Type Differences in the Epithelial Secretomes

The invention is useful in the assessment of inflammatory response in the airways induced by the exposure of the airway to pathogens, allergens, and toxins by characterizing and quantifying the response of a patient's lower respiratory tract based on the analysis of protein patterns in the airway fluids and utilizing a novel sample collection device interfaced with smartphone and mobile computing platform. These proteins can be free-floating or bound in nanovesicles (exosomes).

RSV infections produce a variety of clinical syndromes including upper respiratory tract infections (with or without recurrent otitis media) and lower respiratory tract infections (LRTIs). Although the majority of infections produce an uncomplicated URI, in ~2% of predisposed children RSV can spread into the lower airways, producing LRTI. RSV is consequently the most common cause of childhood LRTIs, responsible for 120,000 hospitalizations for LRTI (bronchiolitis) in the US annually, and represents the leading cause of infant viral death worldwide. Apart from its acute morbidity, severe LRTIs are associated with reshaping the pulmonary immune response, producing Th2 polarization and enhancing susceptibility to recurrent virus-induced wheezing through the next several decades of life. The mechanisms by which LRTIs reprogram the pulmonary immune system are not fully understood.

LRTIs from RSV are due, in part, to secreted signals from lower airway cells that modify immune response and trigger airway remodeling. To understand this process, we applied an unbiased quantitative proteomics analysis of the RSV-induced epithelial secretory response in cells representative of the trachea (hBECs) vs small airway bronchiolar cells (hSAECs). A workflow was established using telomerase-immortalized human epithelial cells that revealed highly reproducible cell type-specific differences in both secreted proteins and nanoparticles (exosomes). Approximately one-third of secretome proteins are exosomal, with the remainder from lysosomal and vacuolar compartments. We applied this workflow to three independently derived primary human cultures from trachea (phBECs) vs bronchioles (phSAECs). 577 differentially expressed proteins from control supernatants and 966 differentially expressed proteins from RSV-infected cell supernatants were identified at a 1% false discovery rate (FDR). Fifteen proteins unique to RSV-infected phBECs were regulated by epithelial-specific ets homology factor (EHF). 106 proteins unique to RSV-infected hSAECs were regulated by the transcription factor NFκB. In this latter group, we validated the differential expression of Chemokine (C—C Motif) Ligand 20 (CCL20)/macrophage-inducible protein (MIP)3α, thymic stromal lymphopoietin (TSLP) and chemokine (CC) ligand 3-like 1(CCL3-L1) because of their roles in Th2 polarization. CCL20/MIP3α was the most active mucin-inducing factor in the RSV-infected hSAEC secretome, and was differentially expressed in smaller airways in a mouse model of RSV infection. These studies provide insights into the complexity of innate responses, and regional differences in epithelial secretome participating in RSV LRTI-induced airway remodeling.

Materials and Methods

Cell Culture and Treatment.

Immortalized human bronchial epithelial cells (tert-hBECs) and small airway epithelial cells (tert-hSAECs) were established by transducing primary cells with human telomerase and cyclin-dependent kinase (CDK)-4 retrovirus constructs (22, 23). hBECs and hSAECs were grown in basal medium supplemented with growth factors (Lonza, Walkersville) in 10 cm Petri dishes in a humidified incubator with 95% air/5% $CO_2$ at 37° C. At 80-90% confluence, the medium was changed, fresh basal medium without growth supplements was added to the plates, and the cells infected with pRSV (MOI 1.0) for 24 h. Conditioned Medium (CM) was collected and centrifuged at 2000×g at 4° C. for 20 min to remove any dead cells. The supernatant was centrifuged at 10,000×g at 4° C. for 10 min to remove any cell debris. The supernatant was used immediately for secretome analysis. Cells from the same plates were lysed in Trizol for whole-cell protein preparation. Experiments were performed in biological triplicates.

For studies with primary human bronchial epithelial cells (phBECs) and phSAECs, cells from three different donors were obtained from Lonza. CM was prepared from hBECs or hSAECs 24 h post-infection (MOI=1.0). When indicated, CM for UV-inactivated RSV-infected cells was used to stimulate hBECs at a 1-25% (vol/vol) concentration for the indicated times. UV inactivation was as previously described (24). For antibody neutralization, 20 μL of RSV-CM was mixed with anti-CCL20 Ab (R&D Systems, Minneapolis, Minn.).

Exosome Preparation.

Exosome isolation was performed by differential centrifugation at +4° C. to minimize protein degradation. Cells were removed by low-speed centrifugation at 400×g, 10 min. The cleared supernatant was then sequentially centrifuged at 2000×g for 15 min and 10,000×g for 30 min to remove any remaining cell debris/microvesicles. Exosomes were finally pelleted by ultracentrifugation at 100,000×g for 2 h and washed in PBS (without Ca++ or Mg++) at 100,000×g, 60 min. After washing, the pellet was resuspended in a total of 200 μL of PBS. Exosome size was estimated by dynamic light scattering using a Malvern High-Performance Particle Sizer (Malvern Instruments, Westborough Mass.). Data acquisition and analysis were performed using Dispersion Technology Software (DTS, V4.1.26.0) configured for HPPS analysis. Each experimental group had three independent replicates.

Preparation of Sucrose Cushion-Purified RSV (pRSV).

The human RSV A2 strain was grown in Hep-2 cells and prepared by sucrose cushion centrifugation as described. The viral titer was determined by a methylcellulose plaque assay. pRSV aliquots were quick-frozen in dry ice-ethanol, and stored at −70° C. until use.

Immunofluorescence (IF) Microscopy.

Airway cells were plated on cover glasses pretreated with rat tail collagen (Roche Applied Sciences). The cells were fixed with 4% paraformaldehyde in PBS, permeabilized with 0.1% Triton X-100, blocked in 10% goat serum, and incubated with primary rabbit polyclonal Ab to cytokeratin-7 or 19 as indicated. After incubation with Alexa-goat anti-Rb Ab, cells were washed and counterstained with 4',6-diamidino-2-phenylindole (DAPI). The cells were visualized with a Zeiss fluorescence LSM510 confocal microscope at 63× magnification. IF of paraffin-embedded mouse lung was performed following standard protocols. Briefly, lung sections (5-μm) were deparaffinized in xylene and hydrated in ethanol (100%-70%). Sections were washed with deionized water. Antigen unmasking was done with 1.0 mM EDTA, pH8.0. Sections were washed in H$_2$O and blocked with 10% goat serum for 1 h at room temperature in the dark, followed by primary antibody against CCL20 (1:200 dilution, Abcam) overnight at 4° C. in the dark. Sections were washed with TBS-Tween (0.1%) buffer and incubated with goat secondary Ab conjugated with Alexa 568 (DAKO) for 1 h at room temperature in the dark. Sections were washed in TBS-Tween (0.1%), incubated with DAPI for 1 min, mounted on coverslips and visualized by confocal microscopy (Zeiss) and photographed at 63× magnification.

Apoptosis Assay.

Apoptosis was measured using a commercial annexin V-FITC apoptosis detection kit following the manufacturer's protocol (BioVision, Milpitas, Calif.). Briefly, hBEC and hSAEC cells (1×10$^6$) were infected with or without RSV (MOI 1.0) for 24 h. Cells were dislodged with Accutane (Millipore), washed once with PBS and incubated with 5 μL of annexin V-FITC and 5 μL of Propidium Iodide (PI) in 500 μL of binding buffer for 5 min at room temperature in the dark. Annexin V-FITC and PI labeling was measured by flow cytometry.

Transmission Electron Microscopy (TEM).

A 10 μL aliquot from the exosome suspension was diluted in deionized water, applied to 200 mesh Formvar/carbon coated copper grids (Electron Microscopy Sciences) for 10 min at room temperature (24° C.) and negatively stained with 2% uranyl acetate (UA). The grids were examined in a Philips CM-100 transmission electron microscope at 60 kV FEI (Thermo-Fischer). Exosome images were acquired with a Gatan Orius 2001 charge-coupled device (CCD) camera.

Secretome Digestion.

About 10 mL of the CM supernatant was added into a 3K filter unit (Millipore, Billerica, Mass.) and centrifuged at 14,000×g for 15 min. 400 μL of 8 M urea was added into the filter unit and centrifuged at 14,000×g for 15 min, and this step repeated once. The solution remaining in the filter device was collected for protein digestion. Proteins were reduced with 10 mM dithiothreitol for 30 min, followed by alkylation with 30 mM iodoacetamide for 60 min in the dark. The sample was diluted 1:1 with 50 mM ammonium bicarbonate. Proteins were digested with 1.0 μg LysC-tr (Promega) for 12 h at 37° C. and then diluted 4:1 with 50 mM ammonium bicarbonate. The proteins were further digested with 1.0 g trypsin (Promega) for 16 h at 37° C. The digestion was stopped with 0.5% trifluoracetic acid (TFA) and the peptides desalted on a reversed-phase SepPak C18 cartridge (Waters); peptides were eluted using 80% acetonitrile (ACN). The eluate was dried in a SpeedVac and the peptides acidified with 2% ACN-0.1% TFA.

Cellular Proteome Digestion.

About 50 μg of proteins in 8 M guanidine were reduced with 10 mM dithiothreitol, alkylated with 30 mM iodoacetamide, sequentially digested with 1.0 μg LysC-tr and 1.0 μg trypsin as described above for secretome proteins.

Exosome Digestion.

The proteins present in the exosomes were separated from the lipid components by chloroform/methanol precipitation. After resuspension of the chloroform/methanol precipitation pellet in 45 μL of 8 M guanidine, proteins were reduced with DTT, alkylated with iodoacetamide, and sequentially digested with LysC-tr and trypsin as described above.

LC-MS/MS Analysis.

A nanoflow UHPLC instrument (Easy nLC, Thermo Fisher Scientific) was coupled on-line to a Q Exactive mass spectrometer (Thermo Fisher Scientific) with a nanoelectrospray ion source (Thermo Fisher Scientific). Peptides were loaded onto a C18 reversed-phase column (25 cm long, 75 m inner diameter) and separated with a linear gradient of 5-35% buffer B (100% acetonitrile in 0.1% formic acid) at a flow rate of 300 nL/min over 240 min. MS data were acquired using a data-dependent Top15 method dynamically choosing the most abundant precursor ions from the survey scan (400-1400 m/z) using HCD fragmentation. Survey scans were acquired at a resolution of 70,000 at m/z 400. Unassigned precursor ion charge states as well as singly charged species were excluded from fragmentation. The isolation window was set to 3 Da and fragmented with a normalized collision energy of 27. The maximum ion injection times for the survey scan and the MS/MS scans were 20 ms and 60 ms, respectively, and the ion target values were set to 1e6 and 1e5, respectively. Selected sequenced ions were dynamically excluded for 30 seconds. Data were acquired using Xcalibur software (Thermo).

Data Processing and Bioinformatic Analysis.

Mass spectra were analyzed using MaxQuant software version 1.5.2.8 using the Andromeda search engine. The initial maximum allowed mass deviation was set to 10 ppm for monoisotopic precursor ions and 0.5 Da for MS/MS peaks. Enzyme specificity was set to trypsin, defined as C-terminal to arginine and lysine excluding proline, and a maximum of two missed cleavages were allowed. Carbamidomethylcysteine was set as a fixed modification, and N-terminal acetylation and methionine oxidation as variable modifications. The spectra were searched with the Andromeda search engine against the Human and RSV SWISSPROT sequence database (containing 20,193 human protein entries and 11 RSV protein entries) combined with 248 common contaminants, and concatenated with the reversed versions of all sequences. Protein identification required at least one unique or razor peptide per protein group. Quantification in MaxQuant was performed using the built in XIC-based label-free quantification (LFQ) algorithm (29). The required false discovery rate (FDR) for identification was set to 1% at the peptide and 1% at the protein level, and the minimum required peptide length to 6 amino acids. Contaminants, reverse identification and proteins only identified by site were excluded from further data analysis. The raw data, and database search results are deposited in ProteomeXchange under Project Accession Number PXD005814. For comparative analysis, the LFQ values were log 2-transformed. After filtering (at least 2 valid LFQ values in at least one group), remaining missing LFQ values were imputed from a normal distribution (width: 0.3; down shift: 1.8). Significance analysis of microarrays (SAM) was used to assess the statistical significance of protein abundances using 1% FDR adjustment and a two-fold cutoff. The normalized spectral abundance factor (NSAF) value for each protein was calculated as $$(NSAF)_k = (I/L)_k / \Sigma_{i=3}^{N} (I/L)_i,$$

where the total MS intensity (I) of the matching peptides from protein k was divided by the protein length (L) and then by the sum of I/L for all uniquely identified proteins in the dataset.

For pairwise comparisons, missing NSAF values for proteins that were only present in either CM or the whole-cell lysate (WCL) were imputed from a normal distribution (width: 0.3; down shift: 1.8). For principal component analysis, unsupervised hierarchical clustering, GO annotation enrichment, and Fisher's exact tests, we used the Perseus bioinformatics platform. We used Ingenuity Pathways Analysis (IPA) for upstream regulator analysis. Gene set enrichment analysis was performed by quantifying canonical pathway enrichment. Exosome analyses were performed by searching the ExoCarta exosome database.

Stable Isotope Dilution (SID)-Selected Reaction Monitoring (SRM)-MS.

The SID-SRM-MS assays were developed. The peptides were chemically synthesized incorporating isotopically labeled [$^{13}C_6^{15}N_4$] arginine or [$^{13}C_6^{15}N_2$] lysine to a 99% isotopic enrichment (Thermo Scientific). The secretome and cellular proteome were digested as described above. The tryptic digests were reconstituted in 30 µL of 5% formic acid/0.01% TFA. An aliquot of 10 µL of diluted stable isotope-labeled standard (SIS) peptides was added to each tryptic digest. These samples were desalted with a ZipTip C18 cartridge; the peptides were eluted with 80% can, dried, reconstituted in 30 µL of 5% formic acid/0.01% TFA, and directly analyzed by liquid chromatography (LC)-SRM-MS using a TSQ Vantage triple quadrupole mass spectrometer equipped with a nanospray source (Thermo Scientific, San Jose, Calif.). Online chromatography was performed using an Eksigent NanoLC-2D HPLC system (AB SCIEX, Dublin, Calif.). An aliquot of 10 µL of each tryptic digest was injected onto a C18 reversed-phase nano-HPLC column (PicoFrit™, 75 µm×10 cm; tip ID 15 m) at a flow rate of 500 nL/min with a 20-min 98% A, followed by a 15-min linear gradient from 2-30% mobile phase B (0.1% formic acid/90% acetonitrile) in mobile phase A (0.1% formic acid). The TSQ Vantage was operated in high-resolution SRM mode with Q1 and Q3 set to 0.2 and 0.7-Da Full Width Half Maximum (FWHM). All acquisition methods used the following parameters: 1800 V ion spray voltage, a 275° C. ion transferring tube temperature, a collision-activated dissociation pressure at 1.5 mTorr, and the S-lens voltage used the values in the S-lens table generated during MS calibration.

All SRM data were manually inspected to ensure peak detection and accurate integration. The chromatographic retention time and the relative product ion intensities of the analyte peptides were compared to those of the SIS peptides. The variation of the retention time between the analyte peptides and their SIS counterparts should be within 0.05 min, and no significant differences in the relative product ion intensities of the analyte peptides and SIS peptides were observed. The peak areas in the extract ion chromatography of the native and SIS version of each signature peptide were integrated using Xcalibur® 2.1. The default values for noise percentage and baseline subtraction window were used. The ratios between the peak area of the native and SIS versions of each peptide were calculated.

Quantitative Real Time PCR (Q-RT-PCR).

For gene expression analyses, 1 µg of RNA was reverse-transcribed using Super Script III in a 20 µL reaction mixture (34). One L of cDNA product was diluted 1:2, and 2 µL of diluted product was amplified in a 20 µL reaction mixture containing 10 µL of SYBR Green Supermix (Bio-Rad) and 0.4 µM each of forward and reverse gene-specific primers. The reaction mixtures were aliquoted into a Bio-Rad 96-well clear PCR plate and the plate sealed with Bio-Rad Microseal B film before insertion into the PCR machine. The plates were denatured for 90 s at 95° C. and then subjected to 40 cycles of 15 s at 94° C., 60 s at 60° C., and 1 min at 72° C. in an iCycler (Bio-Rad). PCR products were subjected to melting curve analysis to assure that a single amplification product was produced. Quantification of relative changes in gene expression was calculated using the ΔΔCt method. Data were expressed as fold change mRNA normalized to cyclophilin or PolB mRNA abundance as indicated as an internal control.

RSV Infection in BALB/c Mice.

BALB/c mice (Harlan) were inoculated intranasally (in) with 50 µL of pRSV (final inoculum, $10^7$ pfu) diluted in PBS under light anesthesia. Twenty-four hours later, the animals were euthanized and their lungs fixed in paraformaldehyde for immunohistochemical analysis. Sections were prepared and stained with H&E or Periodic Acid Schiff (Abcam) stains using standard techniques.

Results

Analysis Pipeline for Cell Type-Specific Differences in the Epithelial Secretome In the first experiment, we examined the effects of RSV on secreted proteins in hBECs derived from the trachea vs hSAECs, derived from the terminal bronchioles. RSV effectively replicates in both cell types, expressing cytokines, producing infectious virions and syncytia formation. To directly compare the levels of RSV replication, tert-hBECs and tert-hSAECs were infected with sucrose cushion-purified (p)-RSV (MOI=1, 24 h). Cells were lysed and the expression of RSV nucleoprotein (N), matrix protein (M), phosphoprotein (P) and matrix M2-1 (M2-1) determined by LC-MS/MS. The levels of RSV expression for all proteins measured were dramatically elevated in tert-hBECs and tert-hSAECs relative to uninfected cells. Interestingly, RSV protein replication was 4-fold higher in tert-hBECs than in tert-hSAECs. Similar results were observed in the conditioned medium (CM) from each cell type (although the protein abundance was lower due to medium dilution), indicating viral secretion. FIG. 17 (left panel) shows the differential expression of secreted proteins (top) vs cell lysates (bottom) for hBECS, while FIG. 17 (right panel) shows the differential expression of secreted proteins in secreted proteins vs lysates for hSAECs.

To determine the effects of RSV infection on cell viability, apoptosis and necrosis rates of control and RSV-infected tert-hBECs and tert-hSAECs (MOI=1, 24 h) were measured by flow cytometry. Cellular necrosis was minimal in both cell types in the absence or presence of RSV infection. However, in the absence of infection, tert-hBECs had a higher basal apoptotic rate than did tert-hSAECs (18.8% vs 10.8%). In both cell types, RSV infection reduced the apoptosis rate. The apoptotic rate of tert-hBECs fell from 18.8 to 12.5%, and of tert-hSAECs fell from 10.8% to 7.9%. The data confirms that under these conditions, the cells are viable, and actively replicating and secreting RSV.

We next sought to quantify the reproducibility of our label-free proteomics workflow to detect changes in secreted proteins by cell type and in response to RSV infection. Cell culture supernatants from 4 independent biological replicates from tert-hBECs vs tert-SAECs were analyzed in mock-infected cells and 24 h after RSV infection. 1,559 proteins were identified in the supernatants with a false discovery rate (FDR) of <1%, determined by target-decoy database searching. To determine biological reproducibility, pairwise analysis of the log 2-transformed protein abundance was performed. The Pearson correlations ($r^2$) were >0.85, indicating a high degree of concordance (Table I). We noted that across samples, the $r^2$ was greater for the RSV-induced CM vs control (for control tert-hBECs, the group-wise mean $r^2$=0.863±0.008, whereas the RSV-infected terthBEC groupwise mean $r^2=0.957\pm0.005$; and for control tert-hSAECs, mean $r^2=0.863\pm0.01$ vs RSV-infected tert-hSAEC mean $r^2=0.936\pm0.011$; both $p<0.05$ Student's t-test).

These data indicate that the method was reproducible, and that the highly abundant proteins in the RSV-induced CM were more accurately measured.

TABLE I

Proteins unique to hSAECs. Shown is a list of proteins unique to hSAECs.

| | | |
|---|---|---|
| Q13509 | Tubulin beta-3 chain | TUBB3 |
| Q9Y570 | Protein phosphatase methylesterase 1 | PPME1 |
| P07738 | Bisphosphoglycerate mutase | BPGM |
| P61081 | NEDD8-conjugating enzyme Ubc12 | UBE2M |
| P56211 | cAMP-regulated phosphoprotein 19 | ARPP19 |
| Q9BV57 | 1,2-dihydroxy-3-keto-5-methylthiopentene dioxygenase | ADI1 |
| Q9H8S9 | MOB kinase activator 1A; MOB kinase activator 1B | MOB1A; MOB1B |
| P50583 | Bis(5-nucleosyl)-tetraphosphatase [asymmetrical] | NUDT2 |
| P99999 | Cytochrome c | CYCS |
| P42126 | Enoyl-CoA delta isomerase 1, mitochondrial | ECI1 |
| Q9P2F8 | Signal-induced proliferation-associated 1-like protein 2 | SIPA1L2 |
| A6NDG6 | Phosphoglycolate phosphatase | PGP |
| Q1KMD3 | Heterogeneous nuclear ribonucleoprotein U-like protein 2 | HNRNPUL2 |
| Q86TI2 | Dipeptidyl peptidase 9 | DPP9 |
| P25325 | 3-mercaptopyruvate sulfurtransferase | MPST |
| O43813 | LanC-like protein 1 | LANCL1 |
| P40261 | Nicotinamide N-methyltransferase | NNMT |
| Q00169 | Phosphatidylinositol transfer protein alpha isoform | PITPNA |
| P61086 | Ubiquitin-conjugating enzyme E2 K | UBE2K |
| Q13126 | S-methyl-5-thioadenosine phosphorylase | MTAP |
| P10768 | S-formylglutathione hydrolase | ESD |
| P50479 | PDZ and LIM domain protein 4 | PDLIM4 |
| P82979 | SAP domain-containing ribonucleoprotein | SARNP |
| P27144 | Adenylate kinase 4, mitochondrial | AK4 |
| Q9BY32 | Inosine triphosphate pyrophosphatase | ITPA |
| P48637 | Glutathione synthetase | GSS |
| Q9GZP4 | PITH domain-containing protein 1 | PITHD1 |
| Q9NZD2 | Glycolipid transfer protein | GLTP |
| Q05397 | Focal adhesion kinase 1 | PTK2 |
| P52943 | Cysteine-rich protein 2 | CRIP2 |
| P42771 | Cyclin-dependent kinase inhibitor 2A, isoforms 1/2/3; Cyclin-dependent kinase 4 inhibitor B | CDKN2A; CDKN2B |
| P30519 | Heme oxygenase 2 | HMOX2 |
| Q9P0L0 | Vesicle-associated membrane protein-associated | VAPA |
| P21399 | Cytoplasmic aconitate hydratase | ACO1 |
| P09417 | Dihydropteridine reductase | QDPR |
| P23434 | Glycine cleavage system H protein, mitochondrial | GCSH |
| P35270 | Sepiapterin reductase | SPR |
| Q92882 | Osteoclast-stimulating factor 1 | OSTF1 |
| O15347 | High mobility group protein B3 | HMGB3 |
| Q99798 | Aconitate hydratase, mitochondrial | ACO2 |
| Q9Y2D5 | A-kinase anchor protein 2 | AKAP2 |
| P58107 | Epiplakin | EPPK1 |
| Q9NX46 | Poly(ADP-ribose) glycohydrolase ARH3 | ADPRHL2 |
| P04181 | Ornithine aminotransferase, mitochondrial; Ornithine aminotransferase, hepatic form; Ornithine aminotransferase, renal form | OAT |
| P50452 | Serpin B8 | SERPINB8 |
| Q96EK6 | Glucosamine 6-phosphate N-acetyltransferase | GNPNAT1 |
| Q969D9 | Thymic stromal lymphopoietin | TSLP |
| Q8TEA8 | D-tyrosyl-tRNA(Tyr) deacylase 1 | DTD1 |
| Q5JRX3 | Presequence protease, mitochondrial | PITRM1 |
| Q53FA7 | Quinone oxidoreductase PIG3 | TP53I3 |
| P54105 | Methylosome subunit pICln | CLNS1A |
| O75884 | Putative hydrolase RBBP9 | RBBP9 |
| O95994 | Anterior gradient protein 2 homolog | AGR2 |
| Q8NBJ7 | Sulfatase-modifying factor 2 | SUMF2 |
| P16619 | C-C motif chemokine 3-like 1; LD78-beta(3-70); LD78-beta(5-70) | CCL3L1 |
| P52566 | Rho GDP-dissociation inhibitor 2 | ARHGDIB |
| O60749 | Sorting nexin-2 | SNX2 |
| P36551 | Oxygen-dependent coproporphyrinogen-III oxidase, mitochondrial | CPOX |
| Q9UFN0 | Protein NipSnap homolog 3A | NIPSNAP3A |
| Q8WWM9 | Cytoglobin | CYGB |
| P04179 | Superoxide dismutase [Mn], mitochondrial | SOD2 |
| P67870 | Casein kinase II subunit beta | CSNK2B |
| O60701 | UDP-glucose 6-dehydrogenase | UGDH |
| P30084 | Enoyl-CoA hydratase, mitochondrial | ECHS1 |

TABLE I-continued

Proteins unique to hSAECs. Shown is a list of proteins unique to hSAECs.

| | | |
|---|---|---|
| P13804 | Electron transfer flavoprotein subunit alpha, mitochondrial | ETFA |
| O15305 | Phosphomannomutase 2 | PMM2 |
| O76054 | SEC14-like protein 2 | SEC14L2 |
| P49411 | Elongation factor Tu, mitochondrial | TUFM |
| Q5T2P8 | Annexin A8-like protein 1 | ANXA8L1 |
| Q16836 | Hydroxyacyl-coenzyme A dehydrogenase, mitochondrial | HADH |
| Q9Y4K1 | Absent in melanoma 1 protein | AIM1 |
| Q9HD15 | Steroid receptor RNA activator 1 | SRA1 |
| Q59GN2 | Putative 60S ribosomal protein L39-like 5/39 | RPL39P5; RPL39 |
| O15400 | Syntaxin-7 | STX7 |
| P31146 | Coronin-1A | CORO1A |
| Q13642 | Four and a half LIM domains protein 1 | FHL1 |
| Q9H993 | UPF0364 protein C6orf211 | C6orf211 |
| Q15149 | Plectin | PLEC |
| P35754 | Glutaredoxin-1 | GLRX |
| Q01995 | Transgelin | TAGLN |
| P48745 | Protein NOV homolog | NOV |
| O00244 | Copper transport protein ATOX1 | ATOX1 |
| P26885 | Peptidyl-prolyl cis-trans isomerase FKBP2 | FKBP2 |
| P06132 | Uroporphyrinogen decarboxylase | UROD |
| P37268 | Squalene synthase | FDFT1 |
| Q08257 | Quinone oxidoreductase | CRYZ |
| Q8NFU3 | Thiosulfate sulfurtransferase/rhodanese-like domain-containing protein 1 | TSTD1 |
| Q9NQR4 | Omega-amidase NIT2 | NIT2 |
| P30838 | Aldehyde dehydrogenase, dimeric NADP-preferring | ALDH3A1 |
| P78556 | C-C motif chemokine 20; CCL20(1-67); CCL20(1-64); CCL20(2-70) | CCL20 |
| O95394 | Phosphoacetylglucosamine mutase | PGM3 |
| Q9ULC4 | Malignant T-cell-amplified sequence 1 | MCTS1 |
| P12532 | Creatine kinase U-type, mitochondrial | CKMT1A |
| Q6FI81 | Anamorsin | CIAPIN1 |
| P42330 | Aldo-keto reductase family 1 member C3 | AKR1C3 |
| Q13011 | Delta(3,5)-Delta(2,4)-dienoyl-CoA isomerase, mitochondrial | ECH1 |
| P51572 | B-cell receptor-associated protein 31 | BCAP31 |
| O75390 | Citrate synthase, mitochondrial | CS |
| P30520 | Adenylosuccinate synthetase isozyme 2 | ADSS |
| Q9NQ88 | Fructose-2,6-bisphosphatase TIGAR | TIGAR |
| Q9H2U2 | Inorganic pyrophosphatase 2, mitochondrial | PPA2 |
| Q15833 | Syntaxin-binding protein 2 | STXBP2 |
| P21266 | Glutathione S-transferase Mu 3 | GSTM3 |
| O75368 | SH3 domain-binding glutamic acid-rich-like protein | SH3BGRL |
| P43490 | Nicotinamide phosphoribosyltransferase | NAMPT |
| Q8WUP2 | Filamin-binding LIM protein 1 | FBLIM1 |
| P19623 | Spermidine synthase | SRM |
| Q9HAV7 | GrpE protein homolog 1, mitochondrial | GRPEL1 |
| P29218 | Inositol monophosphatase 1 | IMPA1 |
| P34897 | Serine hydroxymethyltransferase, mitochondrial | SHMT2 |
| Q9BSJ8 | Extended synaptotagmin-1 | ESYT1 |
| P23368 | NAD-dependent malic enzyme, mitochondrial | ME2 |
| P42704 | Leucine-rich PPR motif-containing protein, mitochondrial | LRPPRC |
| O15231 | Zinc finger protein 185 | ZNF185 |
| Q13630 | GDP-L-fucose synthase | TSTA3 |
| O00515 | Ladinin-1 | LAD1 |

Secretome Proteins are a Distinct Population of Proteins from that Produced by Cellular Lysis To further extend our findings that the proteins in the secretome are not derived from cellular lysis, cellular lysates were prepared from the same experiment and analyzed in parallel. 1,929 unique proteins were quantified from the tert-hBEC and tert-hSAEC whole-cell lysates (WCL). The global protein expression patterns in the CM and WCLs were first examined using principal component analysis (PCA). In this analysis, 91.6% of the variability was accounted for in the first two dimensions, indicating a robust analysis. The WCLs from control or RSV-infected cells clustered by cell type and presence of RSV infection, indicating that biological replicates were consistent. We noted that the control tert-hBEC WCL formed a distinct cluster from that of the tert-hSAEC WCLs, separated by the second principal component dimension. The RSV-infected tert-hBEC WCLs moved in the second dimension to form a cluster that overlapped with both control and RSV-infected tert-hSAEC WCLs. Both the control secretomes of tert-hBECs and tert-hSAECs clustered together, widely separated in the first dimension from the WCL clusters. Upon RSV infection, both the tert-hBEC and tert-hSAEC secretomes migrated up in the second dimension and down in the first dimension. Together, these analyses indicate that the secretome represented a distinct protein set from the cellular lysate, and that RSV induced significant changes in its composition.

460 proteins were present only in the secretome, 885 proteins were unique to the cellular proteome, and 1,044 proteins were present in both datasets. To further confirm that these protein sets were distinct, we conducted unbiased genome ontology cellular component (GOCC) enrichment analysis of the proteins present only in the CM dataset. This analysis indicated that the secretome was enriched with proteins derived from the extracellular region part (205 out of 460 proteins), while the cytoplasmic and mitochondrial proteins were depleted (Fisher Exact test, Benjamini-Hochberg FDR 0.1%; data not shown). By contrast, proteins unique to the WCL were enriched with mitochondrial, ribosomal, and nuclear proteins, and proteins in the extracellular region were depleted.

To confirm that the secreted proteins were independent of cellular lysis in a more quantitative manner, we used the normalized spectral abundance factor (NSAF) method to confirm the enrichment of the proteins in CM and WCL. In spectral counting, larger proteins usually generate more peptides and therefore more spectral counts than smaller proteins. Therefore, the number of spectral counts for each protein is first divided by the protein length, which defines the spectral abundance factor (SAF). Furthermore, to accurately account for sample-to-sample variation, individual SAF values are normalized by dividing by the sum of all SAFs for proteins identified in the sample, resulting in the NSAF value. In this manner, NSAF values are standardized across distinct samples, allowing direct comparisons of the relative protein abundance across samples.

We then conducted a pairwise comparison of NSAF values of proteins in the RSV CM to that of the WCL in RSV-infected tert-hBECs. A two-sample t-test was used to assess the statistical significance of protein enrichment in the RSV CM to that of the WCL. For tert-hBECs, proteins enriched in the CM (indicated in red, Benjamini-Hochberg FDR 1%) included macrophage inhibitory factor (MIF-1), macrophage migration CXCL-10, interferon-stimulated gene-15, high mobility group box (HMGB) 1/2, interferon-induced protein with tetratricopeptide repeats (IFIT)-3, IFN lambda 2, and others. All of these proteins are well-characterized, secreted proteins with defined roles in innate immunity. The abundance of these proteins was depleted in the WCLs. Conversely, we identified high-abundance intracellular proteins in the cell extract (indicated in blue, Benjamini-Hochberg FDR 1%) that were depleted in the CM, including histones H2HAC/1H2BM, mitochondrial single-stranded DNA-binding protein (SSBP)-1, heat shock 10 kDa protein 1 (HSPE1), and actin gamma (ACTG)-1.

Similar observations were made in the comparison of high-abundance proteins in the tert-hSAEC CM and WCLs. Although the proteins comprising the tert-hBEC and tert-hSAEC CM were similar, we noted that CCL5 was in high abundance in the tert-hBEC and much lower in the tert-hSAEC CM. Conversely, CCL20 and IL-6 were much more highly abundant in the tert-hSAEC secretome than in the tert-hBEC secretome. Together these data indicate that the CM samples represent a distinct proteome profile vs that in the WCL. We will refer to this population of proteins as the "secretome" in the remainder of this study.

Biological Functions of the RSV-Induced Secretome

To further support the conclusion that the secretome and cell lysates represent distinct protein pools, we conducted unbiased genome ontology cellular component (GOCC) enrichment. The top-ranked cellular components for the RSV-induced secretome of tert-hBECs (indicated in red) were "extracellular matrix," "extracellular space" and "extracellular organelle," indicating that this sample was enriched in extracellular proteins relative to the reference human proteome. The cellular components corresponding to "cell part," "macromolecular complexes," and "ribonucleoprotein complexes" were depleted in the secretome. By contrast, in the tert-hBEC WCLs, the GOCCs "nucleolar ribonucleoprotein complex," "NADH dehydrogenase complex," and "ribosomal complex" were the top-ranked components. Similarly, the "proteinaceous extracellular matrix" and "extracellular matrix" were the two most significantly depleted cellular components (blue bars, FIG. 2F). These data further support that the proteins identified in the secretome represent a distinct population from the intracellular proteome in the WCL. There were similar findings for tert-hSAECs, with extracellular proteins being the most highly enriched proteins in the hSAEC secretome GOCC analysis. We noted that the cellular component terms for the hBEC and hSAEC secretomes were almost identical.

RSV Induces Exosome Production in a Cell Type-Dependent Pattern

We noted that the majority of 1,044 proteins that were present in both the tert-hBEC and tert-hSAEC secretomes were cytosolic proteins. These cytosolic proteins may be secreted via unconventional protein secretory pathways, perhaps mediated by Golgi or endosomal export mechanisms. To this point, we found that 65 of these common proteins, including heat shock cognate 71 kDa protein (HSPA8), glyceraldehyde-3-phosphate GAPDH), and annexin A2 (ANXA2) are prominent exosomal proteins. To provide some insight into whether endosomal transport was contributing to the RSV-induced secretome, we isolated and quantified exosomal proteins from control and RSV-infected tert-hBECs and tert-hSAECs.

Figure 18:
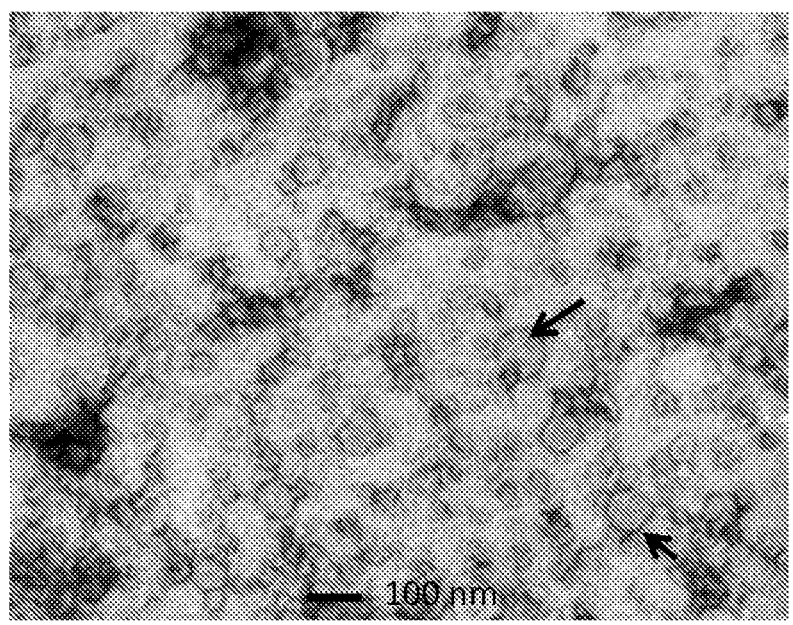
FIG. 18 is a transmission electron microscope (TEM) image of RSV-induced SAEC microparticles, ×98,000, Arrow=100 nm vesicle.

Ultracentrifuge-purified exosomes manifested 112.8±2.0 nm in size by dynamic light scattering, and exhibited a characteristic membrane composition in TEM (FIG. 18). From this fraction, 937 exosomal proteins were identified; of these, 564 proteins were identified in the secretome (373 proteins unique to the exosomal fraction were below the limit of detection and not observed in the secretome analysis). The 937 proteins were subjected to GOCC. Significantly enriched cellular components included lysosomal, vacuolar, and endoplasmic reticular. Out of 937 identified exosome proteins, 853 were quantified across the experimental groups. Pairwise comparison by cell type and presence of RSV infection was accomplished using Student's t-test, as shown in a Volcano plot, where the Log 2 fold change is plotted vs the Log 10-transformed p value. RSV infection caused up-regulation of 220 tert-hSAEC and 241 tert-hBEC exosomal proteins; and downregulation of 146 tert-hSAEC and 223 tert-hBEC exosomal proteins (FDR<0.05). The protein contents in the exosome also display cell type differences. In the basal state, 31 proteins were more abundant in the tert-hSAEC exosome fraction, while 60 proteins were more abundant in the tert-hBEC exosome fraction (FDR<0.05). After RSV infection, 273 exosome proteins were different by cell type, with 134 proteins more abundant in RSV-infected tert-hSAEC exosomes and 139 proteins more abundant in RSV-infected tert-hBEC exosomes (FDR<0.05).

We applied a statistical filter using a p value (Student's t-test with Benjamini-Hochberg FDR correction of <0.05) and an expression filter of ±5-fold change between control vs RSV-infected NSAF to identify the most highly differentially expressed exosomal proteins. The expression patterns were next compared by hierarchical clustering. These data clearly indicate that the exosomal proteins are different by cell type, and modified by the presence of RSV infection.

Of the 559 proteins in the secretome not directly found in the exosomal fraction, 80 proteins have identifiable signal peptides, with the remainder being enriched in lysosomal and vacuolar proteins. These findings suggest that the RSV-induced epithelial secretome is mediated primarily by exosomal protein release, with a smaller fraction due to lysosome- or vacuole-mediated export, and a small fraction by classical protein secretion.

Differential Expression Patterns by Cell Type

We next examined the differential expression patterns of secretome by cell type. Statistical analysis of microarray (SAM) was applied to identify differentially expressed proteins using 1% false discovery rate (FDR). SAM identified 71 proteins distinct in the control secretomes from tert-hBECs vs tert-hSAECs. Of these, 61 were upregulated in the tert-hSAEC secretome. Similarly, 131 proteins showed differential expression in the RSV-induced secretomes from tert-hBECS and tert-hSAECS. Of these, 65 were upregulated in hSAECs.

The differentially expressed proteins were subjected to 2-dimensional hierarchical clustering. Hierarchical clustering groups proteins whose expression patterns are most similar across cell type and treatment condition. The samples are also clustered by the patterns of proteins. In this analysis, the treatment groups co-clustered in the vertical dimension, consistent with the findings in PCA analysis that the replicates from each cell type are highly similar. By inspection of the proteins in the rows, 5 distinct patterns of protein expression emerged. One group represented proteins abundant in control tert-hBECs whose expression is inhibited in response to RSV (not expressed by tert-hSAECs). One group represented proteins expressed by tert-hSAECs whose abundance is decreased in response to RSV. One group represented proteins only expressed by RSV-infected tert-hSAECs. One group represented proteins induced by RSV that are common to both cell types. One group represented proteins induced by tert-hBECs but not tert-hSAECs. One of these groups contained a number of immunologically significant proteins, including CXCL1, IL-6 and CCL20. These data suggest that RSV induces cell-type differences in the secretion of immunologically significant cytokines. Collectively, our analysis pipeline developed using tert-immortalized human epithelial cells, enables the reliable analysis of epithelial secretomes to understand differences by cell type and RSV-induced expression patterns.

Primary Epithelial Cell Secretomes

We next applied our analysis pipeline to primary isolates of human BECs (phBECs) and primary isolates of SAECs (phSAECs). To control for donor effects, the analysis was conducted on three independent donors; two biological replicates were analyzed for each. As validation of the distinct phenotypes, immunofluorescence microscopy was conducted to examine differences in epithelial cytokeratin expression. phBECs express cytokeratins 7 and 19; by contrast, hSAECs have low (or undetectable) cytokeratin 7 and strong cytokeratin 19 expression. Both cell types support active RSV replication and secretion of virus.

Secretome fractions were prepared from control and RSV-infected primary cells. We identified 2,376 proteins with FDR 1%. SAM analysis identified 577 proteins in the secretome from control (uninfected) cells whose expression varied by cell type, and 966 proteins in the secretome from RSV-infected cells whose expression varied by cell type (FDR of 1%). To focus on the most robust differentially expressed proteins, we filtered proteins that showed a 5-fold expression change or greater; this resulted in 492 of the most highly significant and induced proteins. This filtered dataset was subjected to 2-dimensional hierarchical clustering, where each column represents a sample and each row represents an individual protein's abundance. We observed that each sample co-clustered with its replicate, as well as by being grouped by cell type and RSV treatment. The row-wise clustering of proteins produced a pattern highly similar to that observed in the Tert-immortalized hBECs and hSAECs; in this example, cluster 2 represents 11 proteins upregulated by RSV infection in phBECs; cluster 3 represents 116 proteins upregulated by RSV infection in phSAECs; and cluster 4 contains 203 proteins induced by both cell types (Table II).

TABLE II

Proteins upregulated in RSV infected hSAECs.

| Protein ID | Name | Enrichment vs control |
| --- | --- | --- |
| P05187 | ALPP PLAP | 5.9623 |
| Q02878 | RPL6 TXREB1 | 5.916594 |
| P47914 | RPL29 | 5.902925 |
| P62280 | RPS11 | 5.819751 |
| P42677 | RPS27 MPS1 | 5.54576 |
| P42766 | RPL35 | 5.380875 |
| P67809 | YBX1 NSEP1 YB1 | 5.363283 |
| P29034 | S100A2 S100L | 5.029694 |
| P18621 | RPL17 | 5.021404 |
| P62888 | RPL30 | 4.961142 |
| P62851 | RPS25 | 4.758911 |
| P0CW22 | RPS17L | 4.75418 |
| P62841 | RPS15 RIG | 4.634076 |
| P61221 | ABCE1 RLI | 4.593896 |
| P11802 | CDK4 | 4.565168 |
| P80723 | BASP1 NAP22 | 4.535751 |
| P10321 | HLA-C HLAC | 4.533401 |
| P27816 | MAP4 | 4.450186 |
| P27708 | CAD | 4.422149 |
| Q07020 | RPL18 | 4.402696 |
| P23921 | RRM1 RR1 | 4.383801 |
| P07910 | HNRNPC HNRPC | 4.376354 |
| P18124 | RPL7 | 4.340407 |
| P84243 | H3F3A H3.3A H3F3 PP781; H3F3B H3.3B | 4.315348 |
| P62241 | RPS8 OK/SW-cl.83 | 4.303235 |
| P49327 | FASN FAS | 4.301689 |
| P29692 | EEF1D EF1D | 4.269896 |
| Q5T4S7 | UBR4 KIAA0462 | 4.205561 |
| P05787 | KRT8 CYK8 | 4.16108 |
| P08727 | KRT19 | 4.109557 |
| P06748 | NPM1 NPM | 4.069667 |
| P23246 | SFPQ PSF | 3.967895 |
| Q9Y3U8 | RPL36 | 3.910983 |
| P36578 | RPL4 RPL1 | 3.846813 |
| P26373 | RPL13 BBC1 OK/SW-cl.46 | 3.834861 |
| Q03135 | CAV1 CAV | 3.834401 |
| Q8NE71 | ABCF1 ABC50 | 3.832577 |
| O14879 | IFIT3 CIG-49 IFI60 IFIT4 ISG60 | 3.819192 |
| P62917 | RPL8 | 3.806039 |
| Q9NZB2 | FAM120A C9orf10 KIAA0183 OSSA | 3.77524 |
| Q13751 | LAMB3 LAMNB1 | 3.772181 |
| P02545 | LMNA LMN1 | 3.770924 |
| P35579 | MYH9 | 3.736661 |
| Q1KMD3 | HNRNPUL2 | 3.661 |
| P62081 | RPS7 | 3.638772 |
| P46778 | RPL21 | 3.614243 |
| P11586 | MTHFD1 | 3.606673 |
| P78527 | PRKDC HYRC HYRC1 | 3.572419 |
| P62753 | RPS6 OK/SW-cl.2 | 3.554307 |
| Q04637 | EIF4G1 EIF4F EIF4G EIF4GI | 3.551725 |
| P61254 | RPL26 | 3.515504 |
| Q14764 | MVP LRP | 3.472228 |
| P39023 | RPL3 OK/SW-cl.32 | 3.470414 |
| P38646 | HSPA9 | 3.457434 |
| Q13630 | TSTA3 SDR4E1 | 3.441326 |
| P61353 | RPL27 | 3.425266 |
| P32969 | RPL9 OK/SW-cl.103; | 3.413274 |
| Q969Q0 | RPL36AL | 3.359976 |

TABLE II-continued

Proteins upregulated in RSV infected hSAECs.

| Protein ID | Name | Enrichment vs control |
|---|---|---|
| P14868 | DARS PIG40 | 3.344514 |
| O15027 | SEC16A | 3.32998 |
| Q92896 | GLG1 | 3.320409 |
| Q14258 | TRIM25 | 3.317392 |
| P62750 | RPL23A | 3.289345 |
| Q02543 | RPL18A | 3.281097 |
| P84098 | RPL19 | 3.267736 |
| P29966 | MARCKS MACS PRKCSL | 3.201019 |
| Q9P2J5 | LARS KIAA1352 | 3.172232 |
| P50914 | RPL14 | 3.136532 |
| P09914 | IFIT1 | 3.109962 |
| P05387 | RPLP2 | 3.083298 |
| Q7L5D6 | GET4 | 3.060109 |
| P62424 | RPL7A SURF-3 SURF3 | 3.051523 |
| Q00839 | HNRNPU | 3.042754 |
| P83731 | RPL24 | 3.026573 |
| Q8WX93 | PALLD | 3.010279 |
| P15924 | DSP | 2.933567 |
| P49207 | RPL34 | 2.925651 |
| P31689 | DNAJA1 | 2.917788 |
| P46779 | RPL28 | 2.913665 |
| O75369 | FLNB | 2.872175 |
| P61313 | RPL15 | 2.856303 |
| P62913 | RPL11 | 2.853224 |
| P12268 | IMPDH2 | 2.818721 |
| P62899 | RPL31 | 2.812293 |
| P27635 | RPL10 | 2.812172 |
| Q7L2H7 | EIF3M | 2.810656 |
| O95232 | LUC7L3 | 2.738709 |
| P62701 | RPS4X | 2.726098 |
| O15427 | SLC16A3 MCT4 | 2.723415 |
| P16070 | CD44 | 2.708791 |
| P01891 | HLA-A | 2.704322 |
| Q6UXN9 | WDR82 | 2.696573 |
| O00571 | DDX3X | 2.686682 |
| P49411 | TUFM | 2.65141 |
| Q13753 | LAMC2 | 2.630439 |
| Q7Z2W4 | ZC3HAV1 | 2.590558 |
| P46776 | RPL27A | 2.564557 |
| P62906 | RPL10A NEDD6 | 2.560694 |
| P62263 | RPS14 PRO2640 | 2.547316 |
| P40429 | RPL13A | 2.508743 |
| P35268 | RPL22 | 2.497353 |
| Q04695 | KRT17 | 2.470875 |
| P30484 | HLA-R HLAB | 2.460592 |
| Q12906 | ILF3 | 2.454803 |
| Q9Y6G9 | DYNC1LI1 DNCLI1 | 2.437955 |
| P84103 | SRSF3 | 2.425323 |
| P22102 | GART | 2.389263 |
| P05388 | RPLP0 | 2.367745 |
| P15559 | NQO1 | 2.349192 |
| Q13347 | EIF3I | 2.336395 |
| P46782 | RPS5 | 2.331808 |
| O43143 | DHX15 | 2.321755 |
| Q969P0 | IGSF8 | 2.296126 |
| O60701 | UGDH | 2.282827 |
| Q08211 | DHX9 | 2.278905 |
| Q13451 | FKBP5 | 2.264556 |
| Q10471 | GALNT2 | 2.262035 |
| Q9BXJ9 | NAA15 | 2.258991 |
| Q16787 | LAMA3 | 2.223071 |
| Q13501 | SQSTM1 | 2.217754 |
| P62269 | RPS18 | 2.191759 |
| P02786 | TFRC | 2.181157 |
| P17987 | TCP1 | 2.158966 |
| Q99729 | HNRNPAB | 2.084764 |
| Q07955 | SRSF1 ASF | 2.071358 |
| P35527 | KRT9 | 2.041417 |
| Q01650 | SLC7A5 | 2.035409 |
| Q16643 | DBN1 | 2.033986 |
| Q99613 | EIF3C | 2.030562 |
| P15170 | GSPT1 ERF3A | 2.026143 |
| P62244 | RPS15A | 1.982094 |
| P62314 | SNRPD1 | 1.981879 |
| P62910 | RPL32 PP9932 | 1.956094 |
| P62249 | RPS16 | 1.953426 |
| P54136 | RARS | 1.937232 |
| Q13045 | FLII FLIL | 1.930296 |
| Q7Z6Z7 | HUWE1 | 1.928768 |
| O43795 | MYO1B | 1.92866 |
| Q9H3U1 | UNC45A SMAP1 | 1.886301 |
| O95084 | PRSS23 | 1.875822 |
| Q00341 | HDLBP | 1.868465 |
| Q6NZI2 | PTRF | 1.846114 |
| P38159 | RBMX | 1.844283 |
| P30050 | RPL12 | 1.843198 |
| P23229 | ITGA6 | 1.839993 |
| P05121 | SERPINE1 | 1.819857 |
| P62277 | RPS13 | 1.801165 |
| Q16831 | UPP1 UP | 1.766436 |
| O14828 | SCAMP3 | 1.757245 |
| O00567 | NOP56 | 1.750694 |
| P46781 | RPS9 | 1.733911 |
| Q9UQ80 | PA2G4 | 1.708888 |
| P61247 | RPS3A | 1.695866 |
| P31943 | HNRNPH1 | 1.694482 |
| P08195 | SLC3A2 | 1.661627 |
| Q9Y265 | RUVBL1 | 1.655713 |
| P05386 | RPLP1 | 1.653083 |
| O95819 | MAP4K4 | 1.650489 |
| Q96FJ2 | DYNLL2 | 1.646425 |
| Q08J23 | NSUN2 | 1.642181 |
| P62829 | RPL23 | 1.63921 |
| Q16630 | CPSF6 | 1.631618 |
| P63173 | RPL38 | 1.630901 |
| P62847 | RPS24 | 1.627244 |
| Q29963 | HLA-C HLAC | 1.622203 |
| P55263 | ADK | 1.605915 |
| P30838 | ALDH3A1 | 1.593838 |
| P47895 | ALDH1A3 | 1.587489 |
| P53396 | ACLY | 1.557952 |
| Q99880 | HIST1H2BL | 1.552392 |
| Q15435 | PPP1R7 | 1.551719 |
| P62805 | HIST1H4A | 1.54406 |
| P51991 | HNRNPA3 | 1.541353 |
| Q9NR30 | DDX21 | 1.533667 |
| Q9Y230 | RUVBL2 | 1.526808 |
| Q14204 | DYNC1H1 | 1.496601 |
| Q15149 | PLEC PLEC1 | 1.483699 |
| Q92841 | DDX17 | 1.471951 |
| P62854 | RPS26 | 1.468868 |
| P07437 | TUBB | 1.463055 |
| P46940 | IQGAP1 | 1.445934 |
| P46783 | RPS10 | 1.421238 |
| P68371 | TUBB4B | 1.413509 |
| Q9Y263 | PLAA | 1.388859 |
| P13010 | XRCC5 | 1.388359 |
| O76021 | RSL1D1 | 1.381233 |
| P63244 | GNB2L1 | 1.361151 |
| O15371 | EIF3D | 1.346582 |
| P26006 | ITGA3 | 1.33307 |
| P07203 | GPX1 | 1.331746 |
| Q92888 | ARHGEF1 | 1.324795 |
| P22234 | PAICS | 1.320945 |
| P15880 | RPS2 | 1.314672 |
| Q14152 | EIF3A | 1.296245 |
| O60884 | DNAJA2 | 1.289154 |
| P04264 | KRT1 KRTA | 1.288633 |
| Q9HCY8 | S100A14 | 1.280084 |
| O94776 | MTA2 | 1.266098 |
| P23396 | RPS3 | 1.240189 |
| Q13409 | DYNC1I2 | 1.237869 |
| P48643 | CCT5 | 1.23081 |
| P08865 | RPSA | 1.226981 |
| P46379 | BAG6 | 1.224478 |
| P13645 | KRT10 | 1.181838 |
| P07814 | EPRS | 1.17945 |
| P34897 | SHMT2 | 1.17018 |
| Q13310 | PABPC4 | 1.169041 |
| P60228 | EIF3E | 1.164251 |
| Q93008 | USP9X | 1.139412 |
| P60660 | MYL6 | 1.138793 |

TABLE II-continued

Proteins upregulated in RSV infected hSAECs.

| Protein ID | Name | Enrichment vs control |
| --- | --- | --- |
| P19105 | MYL12A | 1.134988 |
| P47897 | QARS | 1.132772 |
| Q92973 | TNPO1 | 1.115839 |
| P13489 | RNH1 | 1.112878 |
| Q92900 | UPF1 | 1.111604 |
| Q9BUF5 | TUBB6 | 1.109345 |
| P02533 | KRT14 | 1.088403 |
| Q16629 | SRSF7 | 1.084932 |
| P46777 | RPL5 | 1.072118 |
| Q13085 | ACACA | 1.060328 |
| Q16881 | TXNRD1 | 1.04443 |
| P50990 | CCT8 | 1.041376 |
| P26640 | VARS | 1.02682 |
| P09913 | IFIT2 | 1.024306 |
| P13639 | EEF2 | 1.01451 |
| P35908 | KRT2 | 1.006343 |
| P68366 | TUBA4A | 1.002294 |
| P39019 | RPS19 | 1.001507 |

Independent Confirmation of Differential Secretion Patterns

Figure 19:
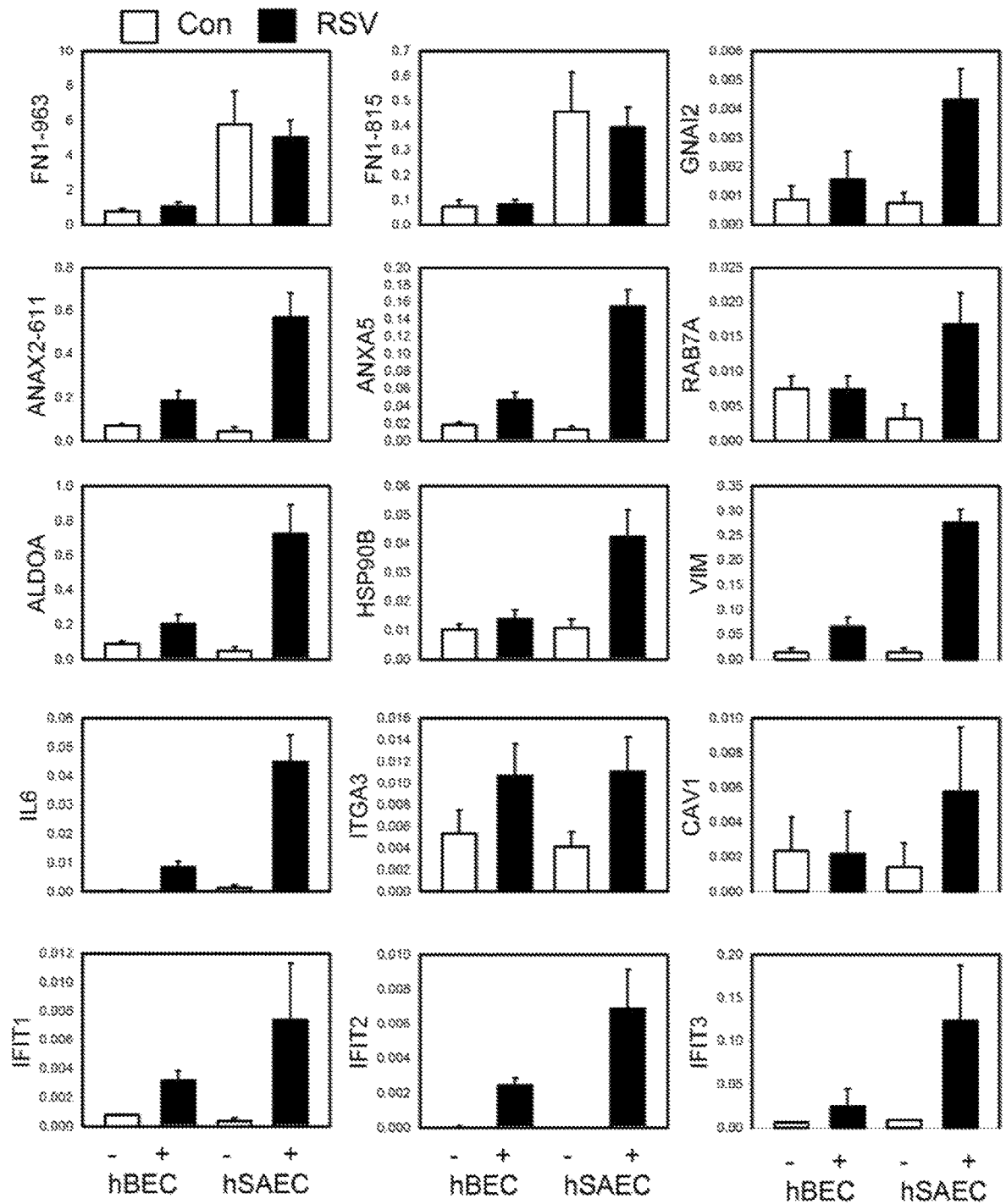
FIG. 19 shows graphs of SID-SRM for each protein providing independent confirmation of differential secreted proteins.

To validate the differentially expressed protein patterns, we independently quantified their expression using SID-SRM-MS. The results are shown in FIG. 19. This method is a 'targeted' MS approach for the detection and accurate quantification of proteins in a complex background where signature proteotypic peptides unique to the protein of interest are monitored in a high mass accuracy mass spectrometer. Because the peptide fragments are then subjected to fragmentation, the assay provides structural specificity and therefore is the most accurate approach available for direct quantification of target proteins in a complex mixture. SRM assays were developed for the measurement of 15 proteins. These assays confirmed the constitutive cell type-specific expression of fibronectin (FN1), and the RSV-induced expression of guanine nucleotide-binding protein (GNAL2), annexin (ANA)-X2, ras oncogene (RAB)-7A, aldolase (ALDO)-A, heat shock protein (HSP)-90, vimentin (VIM), IL-6, integrin alpha 3 (ITGA3), caveolin (CAV)-1 and IFIT-1/2/3 by phSAECs. These data indicated that RSV induces differential expression of proteins by cell type.

Biological Functions of Secreted Proteins

To gain further understanding of RSV-inducible proteins, we analyzed the clusters by GO biological function and Gene Set Enrichment Analysis (GSEA), primarily focusing on clusters 2, 3 and 4. The 11 proteins in cluster 2 were too limited to identify extensive enriched GO categories. Relative to the human proteome, cluster 2 was depleted in the GO category for metabolic process. GSEA showed enrichment for extrinsic prothrombin pathway and fibrinolysis pathway, predominantly determined by the presence of fibrinogen. The 116 proteins in cluster 3, uniquely expressed by RSV-infected hSAECs, showed enrichment for metabolic processes (organic acid, cellular ketone, and small molecule) relative to the human proteome, and depletion in RNA processing. GSEA identified enrichment of canonical pathways for glycoxylate, carbonyl, porphyrin and amino acid metabolism, and oxidative reduction. This analysis suggests that phSAECs secrete proteins controlling nucleotide-sugar bioenergetic processes in response to RSV.

The 203 proteins secreted by both epithelial cell types were analyzed in the same manner. This analysis identified the most GO functions numerically, many of which could be collapsed into mRNA processing (splicing, catabolism, ribonuclease complex assembly), DNA cell cycle regulation and others. GSEA indicated enrichment in mRNA destabilization, Wnt signaling, HIV factor interactions and mRNA interaction/metabolism.

Upstream Factor Analysis of Proteins Unique to hSAECs

To obtain further insights into the differentially regulated proteins, we subjected all proteins showing differential expression to IPA upstream regulator analysis. Upstream regulator analysis compares the known effect (transcriptional activation or repression) of a transcriptional regulator on its target genes to the observed changes in protein abundance. In phBECs, the epithelium-specific ets homologous factor (EHF) was predicted to be more upregulated and responsible for regulating MUC1, serum amyloid A2 and kallikrein-related peptidase (KLK-6/7). In phSAECs, the NFkB transcription factor was predicted to be activated to a greater degree in response to RSV infection than in hBECs. The NFkB network is responsible for regulating TSLP, CCL20, BMP2, MMP3 and SOD2.

Secretion of Th2-Differentiating and Mucin-Inducing Cytokines

Figure 20:
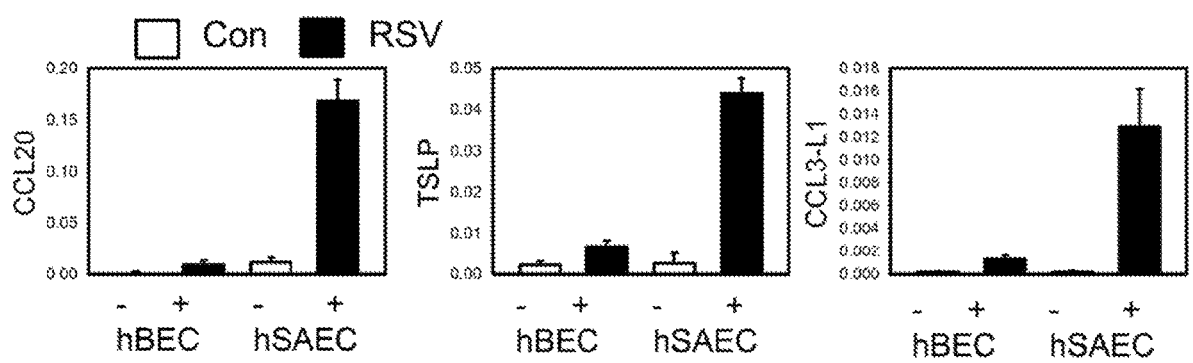
FIG. 20 shows graphs CCL20, TSLP and CCL3-L1 are selectively secreted by lower hSAECs. SID-SRM-MS for each protein by cell type from uninfected (−) or RSV infected (+) cells.

Our protein-level analysis of the proteins unique to hSAECs identified three proteins highly relevant to the pathogenesis of RSV LRTI-TSLP, CCL20, and CCL3-L1. See FIG. 20. These proteins contain signal peptide sequences and are found in the free (non-exosomal fraction). TSLP is produced by RSV-infected airway epithelium and promotes Th2 differentiation by inducing the maturation of antigen-presenting dendritic cells. CCL20 is a potent inducer of epithelial mucin production, Th17 lymphocyte and dendritic cell chemotaxis that promotes formation of mucosal lymphoid tissue formation and plays an important role in the pathology of RSV-induced lung inflammation. Chemokine (C—C motif) ligand 3-like 1 (CCL3-L1) is chemotactic for monocytes and lymphocytes, and interacts with CCR5, a receptor linked to RSV LRTI.

We therefore selected these three immunologically important proteins previously implicated in the pathogenesis of RSV LRTI for validation experiments. To independently measure their differential expression by RSV infection and cell type, we developed and applied highly specific SID-SRM-MS assays to measure target protein abundance in the phBEC and phSAEC secretomes in the presence or absence of RSV infection. We were able to detect a 10-fold increase in CCL20, TSLP and CCL3-L1 expression in RSV-infected phSAECs relative to uninfected controls. By contrast, RSV-infected phBECs showed only 2-fold induction of each chemokine, and at much lower amounts than that in phSAECs. The presence or absence of the BSA/growth factor supplements in the cell culture medium did not affect the RSV-induced cell-type differences in the secretion of CCL20, TSLP and IL-6.

phSAEC-Secreted CCL20 is a Biologically Active Mucin Inducer

Although mucins constitute an important arm of the innate immune response via their ability to trap microorganisms, mucins also play an important role in the pathogenesis of airway obstruction in RSV LRTI. As described earlier, mucous plugging of the small airways is an important mechanism for atelectasis in bronchiolitis, producing ventilation-perfusion mismatching and hypoxia. To determine whether the RSV-induced CCL20 production was at levels sufficient for biological activity, we first evaluated whether phBECs express the CCR6 receptor CCR6 mRNA expression by Q-RT-PCR. Both cell types express CCR6 in uninfected and infected conditions. We next stimulated naïve phBECs with either recombinant CCL20 or CM from RSV-infected phSAECs and assayed for MUC5A mRNA expression by Q-RT-PCR. Recombinant CCL20 induced a reproducible 8-fold induction of MUC5AC mRNA expression relative to control, which was lost at higher concentrations. RSV-CM produced a similar 8-fold induction of MUC5A. Both of these activities were inhibited by the addition of neutralizing CCL20 Ab; pre-immune IgG had no effect. Together these data indicate that RSV-infected phSAECs produce biologically active CCL20 that stimulates mucin production.

Confirmation of Enhanced CCL20 in Lower Airway Epithelial Cells In Vivo

Our quantitative in vitro proteomic studies suggest that lower airway epithelial cells exhibit enhanced CCL20 secretion upon RSV infection. To confirm this, we examined CCL20 expression in a BALB/c mouse model of acute RSV infection established in our laboratories. Immunofluorescence (IF) assays were performed on proximal and distal airways in control and RSV-infected mice. In the absence of primary antibody, no fluorescence was observed. In proximal airways, IF was faintly distributed within the epithelial layer and weakly induced upon RSV infection. By contrast, CCL20 IF was strongly induced in the smaller airways, both upon RSV infection. These (<1 mm diameter) airways were lined with single layer of cuboidal epithelium and lacked cartilage representing bronchiolar and terminal bronchiolar structures (adjacent to alveoli).

To examine whether enhanced mucin production was seen in this model, tissue sections were stained with PAS to assess mucin production. We observed enhanced PAS staining in these smaller, distal airways. Together, these studies confirm that lower airway epithelial cells in the distal airways produce enhanced CCL20 expression with increased mucin production in this mouse model of RSV infection.

Discussion

In this study, we apply unbiased proteomics to identify 577 high-confidence proteins whose RSV-induced expression patterns differ between primary human epithelial cells derived from the conductive airway (trachea) and those of the small airways (bronchioles). A surprising finding was that about third of the proteins identified in the secretome are exosomal. Although a number of RSV-inducible proteins are common, RSV induces a group of proteins unique to the phSAECs that are immunologically significant—TSLP, CCL20, CCL3-L1 and IL-6. Differential expression of these proteins was independently validated by specific SID-SRM-MS assays. We demonstrate that CCL20 is the major mucin-promoting cytokine in hSAECs secretome, and validate its preferential expression in lower airways in a BALB/c mouse model of RSV infection. These data advance our understanding of the epithelial innate response and provide insight into how RSV LRTI is associated with enhanced mucin production and lower airway obstruction. Our study surprisingly shows the novel observation that TSLP and CCL20 are preferentially secreted by RSV-infected lower airway epithelial cells, perhaps providing information on how LRTI is associated with Th2 lymphocyte skewing, DC recruitment and Th17 activation.

Example 9

Exosome Preparation and Characterization

Exosomes are small 90-100 nm extracellular vesicles derived from endosomal multivesicular bodies (exosomes) that function in extracellular signal transduction. Enclosed within protective phospholipid bilayers, exosomes proteins, vasoactive leukotrienes, and small RNAs (sncRNA and miRNAs), whose dynamic composition is determined by the microenvironment of the secreting cell. Currently we understand that exosomes participate in signal transduction in distant target cells, affect cellular behavior. With greater understanding of how exosomal content is affected by changes in the microenvironment of the cellular origin, profiling and quantification of exosome content may be used as "liquid biopsies" to detect occult cellular stress, inflammation, tissue injury, wound healing, tissue remodeling and cancer. Although much study has focused on exosomes in the circulation, virtually all cell types produce exosomes and consequently they are found in virtually all biological fluids, including the airway.

To characterize; 1) the proteomic, RNA and metabolic content of exosome; 2) exosomal activities and 3) exosomal function, sample collection and storage conditions need to be identified that have minimal impact on exosome integrity. We characterized the effects of storage conditions on airway exosome composition, integrity and morphology By comparing surface and morphological properties as well as protein content of enriched exosomes from the airway following storage at 4° C. and at −80° C. As part of these efforts enriched exosomes were isolated by differential ultracentrifugation from mouse bronchoalveolar lavage after poly(I:C)-induced airway inflammation, washed in PBS and stored at 4° C. and −80° C. Exosomal structure was assessed by dynamic light scattering (DLS), transmission electron microscopy (TEM) and charge density (zeta potential, $\zeta$). Protein content, as well as leaking/dissociating peri-exosomal proteins were identified by label-free LC-MS/MS.

Results

Storage Conditions Affect Exosome Size:

In our studies of BALF exosomes, we observed that freshly prepared exosomes had distinct dynamic light scattering (DLS) patterns compared to those frozen at −80° C. Intrigued that storage conditions may introduce a systematic effect, we undertook a more systematic investigation into effects of freezing on BALF exosome structure and content. For this a pool of enriched exosomes was freshly prepared from the BALF, washed in PBS, measured, aliquoted and stored at 4° C. and at −80° C.

The Z-average DLS % intensity size distribution metric was compared for the different storage conditions. Freshly prepared BALF exosomes produced an asymmetric size distribution of vesicles from 50-170 nm, with an average size of 94.5±1.7 nm. By contrast, exosomes stored at 4° C. underwent a size shift of its average size to 104±1.15 nm in three independent isolations (p<0.05, t-test). A much more dramatic change was observed for BALF exosomes stored at −80° C., where the average increased to 125±1.15 nm (p<0.001, t-test). In addition to this increase in exosome size, a Poisson like distribution and high PDI shift in the DLS profile was noted, indicating polydispersity in the samples. Multiple overlapping Gaussian size distributions results in a long tail mixture model, suggesting freezing produced a population of larger nanovesicle aggregates up to 400 nm in diameter.

To further understand the influence of storage effects on exosome ultrastructure, we subjected the exosomes to ultrastructural studies using transmission electron microscopy (TEM). Both the freshly prepared BALF exosomes and those stored at 4° C. appeared in TEM as isolated, membrane-encapsulated nanovesicles, with the characteristic artificial central depression ("cupping") ascribed to cellulose embedding. By contrast, the fraction of the BALF exosomes stored at −80° C. were larger, aggregated and showed appearance of multi-lamellar membrane layers, consistent with the results of the study using dynamic light scattering to assess changes induced in exosome by freezing and thawing of samples.

Storage Effects on Zeta Potential ($\zeta$):

We next examined the effect of storage conditions on the charge density distribution around the exosome, a parameter known as the zeta potential. Exosomes from BAL that were freshly prepared and stored at 18° C. demonstrated $\zeta$ between −34.8 and −32.4 mV. These $\zeta$ are within the potential range expected for airway exosomes due to the high distribution of negatively charged membrane phospholipids (36). It is remarkable that after thawing from −80° C., the $\zeta$ was further diminished to −16.5 mV to −9.88 mV, indicating that freezing is extremely disruptive to the structure and physical properties of the BALF exosomes. Importantly, at such $\zeta$, the exosomes possess virtually no barrier against fusion processes, providing a physicochemical explanation for the exosomal fusion in TEM and increased size by DLS.

Effect of Storage Conditions on Protein Content:

To determine whether the different storage conditions affected the exosomal protein content, we conducted unbiased label-free quantitation of the exosomes after 4° C. and −80° C. storage. Three individual replicate analyses from two independent experiments were conducted to measure changes in protein content. Unbiased proteome profiling was conducted by LC-MS/MS analysis after lipid depletion using an optimized chloroform/methanol precipitation method. A total of 848 proteins were identified at an FDR of 1% or less. This protein set was enriched in proteins important in translation/ribosomal RNA processing, vesicular transport and cytoskeletal structure (Table III), compatible with the functions and subcellular origin of exosomes. Moreover, 80 of the top 100 exosomal proteins in Exocarta were identified, establishing that this preparation was enriched in exosomes. Functional analysis showed that these proteins were significantly enriched in 39 biological pathways, including tRNA aminoacylation, glycolysis, translation, macrophage activation, proteolysis and others (Table IV).

To compare the effect of storage in exosome content, we examined a measure of differential expression (−log 10 transformed p value of two sample t-test) vs the fold change of proteins abundance in exosome (4° C. relative to −80° C.) using a volcano plot. From this analysis, 755 (89%) of proteins shown no difference in abundance in exosome as a result of the storage temperature. However, 61 proteins were more abundant in the exosomes stored at −80° C. relative to exosome stored at 4° C., by contrast, and 31 proteins were more abundant in the exosomes stored at 4° C. relative to those stored at −80° C., indicating that a small population of exosome proteins was more sensitive to the storage temperature. Consistency in the changes in protein abundance by replicate were analyzed by hierarchical clustering of the log 2-normalized abundance.

Protein Leakage and Dissociation into the Supernatant Upon Storage

To further understand the effects of storage, we used LC-MS to identify and quantify the proteins in supernatant after 4° C. and −80° C. storage. A total of 698 proteins were identified with high confidence, and functionally analyzed by GO classification. Interestingly, these proteins affect biological pathways that are functionally distinct from those identified in the exosomal preparation. For example, the supernatant proteins are enriched in carbohydrate metabolism (gluconeogenesis/glycolysis), TCA cycle and fatty acid biosynthesis pathways (Table V). We noted that expression of 554 proteins are unchanged, appearing in the supernatant independently of storage conditions. Interestingly, a smaller group of the peri-exosomal proteins appear in the supernatants dependent on the storage conditions. 67 proteins are enriched in the supernatant from the exosomes stored at −80° C., and a second set of 78 unique proteins is enriched in the exosomes stored at 4° C. ($p<0.05$).

We next analyzed the supernatant fractions for the presence of the 62 proteins depleted from the exosome preparations stored at 4° C. We found that 22 proteins depleted during 4° C. storage did not appear in the supernatant. We interpret this data to mean that these proteins were metabolized or degraded at 4° C. Conversely, 29 of the 31 proteins depleted from the exosome preparations stored at −80° C. appeared in the soluble supernatant. We interpret this finding to indicate that 93% proteins lost at −80° C. leaked into the supernatant due to membrane fusion and/or membrane disruption.

BALF exosomes undergo dynamic changes in protein (cytokines), arachidonic acid (leukotrienes) and miRNA content that could potentially regulate innate immunity, hyper-responsiveness and cellular inflammation in the airway. Although our study was not designed to examine the effect of poly(I:C) inflammation on exosomal content, our data significantly extends the number of proteins contained within BALF exosomes. Here we identify 848 high confidence proteins that are enriched in 80 of the top 100 proteins in the ExoCarta database that have previously been identified as exosomal markers. Pathway analysis indicates that the poly(I:C) induced exosomes are enriched in a number of biological processes. These enriched biological processes include tRNA aminoacylation and protein translation (Table IV), perhaps participating in the processing or activity of the miRNA content.

In summary, our studies demonstrate that freezing and subsequent thawing resulted in an increase in exosomal size, promoting aggregation and multilamellar vesicle formation. Storage at −80° C. resulted in increasing the size of exosome by more than 20% while producing $\zeta$ compatible with vesicular fusion. A total of 848 proteins were identified in the exosomes, significantly enriched in ribosomal/translation, vesicular and cytoskeletal functions mapped into 39 biological pathways. 62 inflammation and integrin signaling proteins were depleted in exosomes stored at 4° C. 31 coagulation and cellular metabolic proteins were depleted in exosomes stored at −80° C. storage. After 4° C. storage, 224 proteins appeared in the supernatant relative to that in the wash representing exosomal leakage and peri-exosomal protein dissociation. After −80° C. storage and thawing cycle, 194 proteins appeared in the supernatant vs that of the original wash, suggesting distinct protein groups leak from exosomes based on storage conditions.

CONCLUSIONS

Storage destabilizes surface characteristics and protein content of airway exosomes. For preservation of exosomal content and functional analysis, airway exosomes should be isolated and immediately analyzed.

TABLE III

Subcellular Compartment Enrichment of exosomal proteins. 848 high confidence proteins were analyzed for subcellular enrichment by GO-Slim (Panther database). Shown is fold enrichment of the pathway and p value (bonferroni correction).

| PANTHER GO-Slim Cellular Component | Enrichment | P value |
| --- | --- | --- |
| ribosome (GO:0005840) | 12.64 | 1.09E−36 |
| cytosol (GO:0005829) | 7.4 | 9.33E−40 |
| vesicle coat (GO:0030120) | 6.53 | 2.49E−03 |
| ribonucleoprotein complex (GO:0030529) | 6.16 | 7.39E−29 |
| actin cytoskeleton (GO:0015629) | 4.43 | 8.50E−10 |
| macromolecular complex (GO:0032991) | 2.7 | 2.40E−21 |
| cytoskeleton (GO:0005856) | 2.47 | 2.05E−06 |
| cytoplasm (GO:0005737) | 2.43 | 1.58E−23 |
| extracellular space (GO:0005615) | 2.26 | 4.94E−05 |
| organelle (GO:0043226) | 2.07 | 8.58E−19 |
| intracellular (GO:0005622) | 1.92 | 1.34E−23 |
| cell part (GO:0044464) | 1.89 | 2.08E−22 |
| extracellular region (GO:0005576) | 1.83 | 1.87E−03 |
| membrane (GO:0016020) | 0.36 | 9.08E−11 |
| plasma membrane (GO:0005886) | 0.32 | 2.36E−07 |
| integral to membrane (GO:0016021) | <0.2 | 4.91E−15 |

TABLE IV

Pathway enrichment of exosomal proteins. 848 high confidence proteins were analyzed for biological processes by GO-Slim (Panther database). Shown is fold enrichment of the pathway and p value (bonferroni correction).

| PANTHER GO-Slim Biological Process | Enrichment | P-Value |
| --- | --- | --- |
| tRNA aminoacylation for protein translation (GO:0006418) | 8.02 | 1.49E−05 |
| glycolysis (GO:0006096) | 6.5 | 1.03E−02 |
| translation (GO:0006412) | 6.19 | 1.07E−28 |
| protein complex assembly (GO:0006461) | 5.14 | 1.25E−09 |
| protein complex biogenesis (GO:0070271) | 5.11 | 1.43E−09 |
| protein folding (GO:0006457) | 4.8 | 9.06E−06 |
| purine nucleobase metabolic process (GO:0006144) | 4.69 | 3.61E−03 |
| chromatin organization (GO:0006325) | 4.21 | 4.20E−11 |
| cellular component biogenesis (GO:0044085) | 3.8 | 3.07E−16 |
| macrophage activation (GO:0042116) | 3.49 | 3.16E−02 |
| fatty acid metabolic process (GO:0006631) | 2.99 | 1.98E−03 |
| cellular amino acid metabolic process (GO:0006520) | 2.97 | 5.57E−04 |
| cellular component organization or biogenesis (GO:0071840) | 2.76 | 9.64E−30 |
| proteolysis (GO:0006508) | 2.58 | 1.29E−07 |
| cellular component organization (GO:0016043) | 2.5 | 3.19E−20 |
| organelle organization (GO:0006996) | 2.47 | 2.56E−08 |
| catabolic process (GO:0009056) | 2.46 | 2.20E−08 |
| protein metabolic process (GO:0019538) | 2.23 | 7.53E−20 |
| lipid metabolic process (GO:0006629) | 2.02 | 7.65E−03 |
| cellular component morphogenesis (GO:0032989) | 1.99 | 3.17E−02 |
| biosynthetic process (GO:0009058) | 1.78 | 2.68E−05 |
| protein transport (GO:0015031) | 1.77 | 5.21E−03 |
| intracellular protein transport (GO:0006886) | 1.75 | 1.06E−02 |
| vesicle-mediated transport (GO:0016192) | 1.73 | 2.48E−02 |
| primary metabolic process (GO:0044238) | 1.68 | 6.64E−24 |
| metabolic process (GO:0008152) | 1.57 | 2.82E−21 |
| transport (GO:0006810) | 1.54 | 2.67E−03 |
| localization (GO:0051179) | 1.53 | 1.14E−03 |
| cellular process (GO:0009987) | 1.32 | 1.41E−09 |
| Unclassified (UNCLASSIFIED) | 0.57 | 0.00E+00 |
| cell surface receptor signaling pathway (GO:0007166) | 0.52 | 1.08E−02 |
| system process (GO:0003008) | 0.51 | 1.07E−03 |
| single-multicellular organism process (GO:0044707) | 0.49 | 8.83E−06 |
| multicellular organismal process (GO:0032501) | 0.47 | 1.18E−06 |
| developmental process (GO:0032502) | 0.46 | 5.25E−05 |
| transcription, DNA-dependent (GO:0006351) | 0.39 | 7.53E−05 |
| transcription from RNA polymerase II promoter (GO:0006366) | 0.35 | 2.40E−04 |
| neurological system process (GO:0050877) | 0.32 | 1.08E−07 |
| regulation of transcription from RNA polymerase II promoter (GO:0006357) | 0.25 | 9.67E−05 |
| sensory perception (GO:0007600) | <0.2 | 1.79E−09 |

TABLE V

GO analysis of peri-exosomal proteins. 699 high confidence peri-exosomal proteins were analyzed for biological processes by GO-Slim (Panther database). Shown is fold enrichment of the pathway and p value (bonferroni correction).

| PANTHER GO-Slim Biological Process | Enrichment | Pvalue |
| --- | --- | --- |
| gluconeogenesis (GO:0006094) | 10.99 | 5.44E-03 |
| tricarboxylic acid cycle (GO:0006099) | 10.45 | 1.57E-03 |
| glycolysis (GO:0006096) | 9.8 | 1.28E-04 |
| fatty acid biosynthetic process (GO:0006633) | 6.3 | 1.53E-03 |
| purine nucleobase metabolic process (GO:0006144) | 6.28 | 1.90E-04 |
| protein complex assembly (GO:0006461) | 5.16 | 4.86E-07 |
| protein complex biogenesis (GO:0070271) | 5.13 | 5.40E-07 |
| blood coagulation (GO:0007596) | 4.62 | 9.15E-03 |
| monosaccharide metabolic process (GO:0005996) | 4.2 | 1.01E-02 |
| chromatin organization (GO:0006325) | 4.04 | 2.32E-07 |
| macrophage activation (GO:0042116) | 3.96 | 3.51E-02 |
| fatty acid metabolic process (GO:0006631) | 3.83 | 7.00E-05 |
| translation (GO:0006412) | 3.64 | 1.18E-06 |
| proteolysis (GO:0006508) | 3.59 | 1.14E-13 |
| cellular component biogenesis (GO:0044085) | 3.45 | 2.17E-09 |
| cellular amino acid metabolic process (GO:0006520) | 3.34 | 5.79E-04 |
| generation of precursor metabolites and energy (GO:0006091) | 3.22 | 2.96E-03 |
| catabolic process (GO:0009056) | 2.98 | 7.38E-11 |
| lipid metabolic process (GO:0006629) | 2.78 | 1.97E-06 |
| cellular component organization or biogenesis (GO:0071840) | 2.58 | 4.22E-18 |
| cellular component organization (GO:0016043) | 2.45 | 4.05E-14 |
| cellular component morphogenesis (GO:0032989) | 2.21 | 2.02E-02 |
| organelle organization (GO:0006996) | 2.15 | 1.30E-03 |
| protein metabolic process (GO:0019538) | 2.12 | 3.65E-12 |
| immune system process (GO:0002376) | 1.79 | 3.12E-03 |
| primary metabolic process ((30:0044238) | 1.69 | 2.39E-18 |
| transport (GO:0006810) | 1.61 | 3.94E-03 |
| metabolic process (GO:0008152) | 1.58 | 2.75E-16 |
| localization (GO:0051179) | 1.55 | 9.11E-03 |
| cellular process (GO:0009987) | 1.24 | 1.05E-03 |
| multicellular organismal process (GO:0032501) | 0.58 | 2.03E-02 |
| Unclassified (UNCLASSIFIED) | 0.57 | 0.00E+00 |
| RNA metabolic process (GO:0016070) | 0.53 | 1.81E-02 |
| developmental process (GO:0032502) | 0.5 | 7.71E-03 |
| cell surface receptor signaling pathway (GO:0007166) | 0.42 | 4.02E-03 |
| neurological system process (GO:0050877) | 0.34 | 4.45E-05 |
| transcription from RNA polymerase II promoter (GO:0006366) | 0.27 | 2.92E-04 |
| regulation of transcription from RNA polymerase II promoter (GO:0006357) | 0.25 | 3.13E-03 |
| sensory perception (GO:0007600) | 0.25 | 7.18E-05 |
| G-protein coupled receptor signaling pathway (GO:0007186) | 0.25 | 1.22E-02 |

The invention claimed is:

1. A method of microfluidic detection of a biological marker in a biological sample collected from a subject, the method comprising:
providing a microfluidic device, said device comprising:
a cartridge and a planar substrate retained in said cartridge, said cartridge comprising a sample inlet well formed in said cartridge above a sample application region in or on said substrate and at least one detection region in fluid communication with said sample application region via a microfluidic channel extending from said sample application region to said detection region, said microfluidic channel having a terminal end positioned distal from said inlet well, and an optional absorbent pad positioned at said terminal end, wherein said detection region comprises a first nanosensor immobilized therein or thereon;
wherein said first nanosensor comprises a central carrier particle, a first particle tethered to said carrier particle via an oligopeptide linkage, and a second particle directly attached to said carrier particle, wherein said oligopeptide linkage comprises a supramolecular recognition sequence, a protease consensus sequence, a post-translationally modifiable sequence, or a sterically hindered benzylether bond for specific interaction with a biological marker, wherein at least one of said first and second particles is a detectable particle and the other of said first and second particles is a quencher particle;

introducing a biological sample collected from said subject into said inlet well of said microfluidics device, said biological sample flowing to said terminal end along said microfluidic chamber, wherein said biological sample contacts said detection region that comprises said first nanosensor immobilized therein or thereon before reaching said terminal end;

exposing said detection region to an energy source to generate a detectable signal from said detectable particle in said first nanosensor; and detecting changes in said detectable signal based upon interaction of said biological sample with said first nanosensor.

2. The method of claim 1, wherein said biological sample comprises exosomes, said method further comprising isolating and optionally lysing said exosomes before contacting said detection region with intact exosomes or lysed exosomes.

3. The method of claim 2, said method comprising detecting biological markers selected from the group consisting of:
markers associated with infected lower airway epithelial cell infection in said lysed exosomes selected from the group consisting of CCL20, TSLP, CCL3-L1, and combinations thereof;
markers associated with inflammation-induced change in cytokine, protease, or kinase activity;
markers associated with cancer-induced changes in alkaline phosphatase, ribonucleotide reductases, or DNA/RNA helicases; and
RNA and/or metabolites, as markers of exosomal activity and function.

4. The method of claim 2, wherein said isolating comprising:
contacting said biological sample with a magnetic capture nanosensor comprising a magnetic nanoparticle attached to a supramolecular recognition sequence for an exosome surface recognition protein, said magnetic capture nanosensor binding to said exosome surface recognition protein to thereby capture said exosomes; and
separating said captured exosomes from the remainder of said biological sample.

5. The method of claim 4, wherein said contacting said biological sample with a magnetic capture nanosensor is carried out in in a second microfluidic device.

6. The method of claim 4, wherein said exosome surface recognition protein is selected from the group consisting of CD9, CD 63, CD81, and combinations thereof.

7. The method of claim 1, said substrate comprising a plurality of detection regions in fluid communication with said inlet well via respective microfluidic channels extending from said sample application region to each of said detection regions, each of said microfluidic channels having a terminal end positioned distal from said sample application region, and an absorbent pad positioned at each of said terminal ends, wherein each detection region comprises a respective nanosensor immobilized therein.

8. The method of claim 7, wherein each of said detection regions comprises a nanosensor for a different biological marker.

9. The method of claim 1, wherein said inlet well has a volume of from about 10 µL to about 5 mL.

10. The method of claim 1, wherein said detection region has a volume of from about 100 pL to about 1 µL.

11. The method of claim 1, wherein from about 10 µL to about 5 mL of said biological sample is introduced into said inlet well.

12. The method of claim 1, wherein said nanosensors have a limit of detection of from about $10^{-9}$ M to about $10^{-18}$ M.

13. The method of claim 1, wherein said detecting occurs about 1 minute to about 20 minutes after said introducing.

14. The method of claim 1, said device further comprising a thin film foil heater for heating said sample in said detection region prior to said detecting.

15. The method of claim 1, wherein said sample inlet well is configured for receiving said sample deposited into said well through an opening in said cartridge, wherein said well comprises a sidewall that extends from said opening to said sample application region, and wherein said sample application region defines a bottom wall of said inlet well.

16. The method of claim 1, said cartridge further comprising an opening above said detection region configured for viewing changes in said detection region.

17. The method of claim 1, wherein said detecting comprising imaging said detection region with a smart device optical sensor.

18. The method of claim 17, said device further comprising a permanent housing for attaching to said smart device, said substrate and cartridge being retained in said housing.

19. A microfluidic device comprising:
a cartridge and a planar substrate retained in said cartridge, said cartridge comprising a sample inlet well formed in said cartridge above a sample application region in or on said substrate and at least one detection region in fluid communication with said sample application region via a microfluidic channel extending from said sample application region to said detection region, said microfluidic channel having a terminal end positioned distal from said inlet well, and an optional absorbent pad positioned at said terminal end, wherein said detection region comprises a nanosensor immobilized therein or thereon; and
wherein said nanosensor comprises a central carrier particle, a first particle tethered to said carrier particle via an oligopeptide linkage, and a second particle directly attached to said carrier particle, wherein said oligopeptide linkage comprises a supramolecular recognition sequence, a protease consensus sequence, a post-translationally modifiable sequence, or a sterically hindered benzylether bond for specific interaction with a biological marker, wherein at least one of said first and second particles is a detectable particle and the other of said first and second particles is a quencher particle.

20. A nanosensor for detecting the presence of an active protein in a sample, said nanosensor comprising:
a central carrier particle;
a first particle connected to said central carrier particle via an oligopeptide linkage, said oligopeptide linkage comprising a supramolecular recognition sequence, said protein having specific binding to said supramolecular recognition sequence without chemical modification or enzymatic cleavage of said linkage; and
a second particle directly attached to said central carrier particle via a non-cleavable linkage;
wherein at least one of said first and second particles is a detectable particle and the other of said first and second particles is a quencher particle; and wherein said detectable particle and quencher particle are separated by a distance that enables Forster resonance energy transfer.

\* \* \* \* \*